United States Patent
Scarborough et al.

(10) Patent No.: US 6,960,580 B2
(45) Date of Patent: Nov. 1, 2005

(54) NITROGENOUS HETEROCYCLIC SUBSTITUTED QUINOLINE COMPOUNDS

(75) Inventors: Robert M. Scarborough, Half Moon Bay, CA (US); Anjali Pandey, Fremont, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 220 days.

(21) Appl. No.: 10/094,191

(22) Filed: Mar. 8, 2002

(65) Prior Publication Data

US 2003/0004158 A1 Jan. 2, 2003

Related U.S. Application Data

(60) Provisional application No. 60/273,951, filed on Mar. 8, 2001.

(51) Int. Cl.$^7$ .................... C07D 215/46; A61K 31/496; A61P 35/00
(52) U.S. Cl. .............. 514/228.2; 514/252.11; 514/253.02; 514/253.06; 544/58.2; 544/61; 544/121; 544/357; 544/363
(58) Field of Search ......................... 514/228.2, 252.11, 514/253.02, 253.06, 253.2; 544/58.2, 61, 121, 357, 363

(56) References Cited

U.S. PATENT DOCUMENTS

| | | | |
|---|---|---|---|
| 6,169,088 B1 * | 1/2001 | Matsuno et al. ....... | 514/252.16 |
| 6,207,667 B1 | 3/2001 | Matsuno et al. | |
| 2002/0068734 A1 | 6/2002 | Matsuno et al. | |

FOREIGN PATENT DOCUMENTS

| | | |
|---|---|---|
| EP | 0882717 A | 12/1998 |
| EP | 1067123 A1 | 10/2001 |
| WO | WO 02/16351 A2 | 2/2002 |
| WO | WO 02/16360 A2 | 2/2002 |
| WO | WO 02/16361 A2 | 2/2002 |
| WO | WO 02/16362 A2 | 2/2002 |
| WO | WO 02/072578 A2 | 9/2002 |

OTHER PUBLICATIONS

Agrawal, Vijal K., et al., "Antiparasitic agents. Part VI. Synthesis of 7–chloro–4–(4–substituted–phenylamino)– and 7–chloro–4–(4–substituted–piperazin–1–yl)quinolines as potential antiparasitic agents", Indian J. Chem., Sect. B, 1987, 26B(6), 550–5.

* cited by examiner

*Primary Examiner*—Bruck Kifle
(74) *Attorney, Agent, or Firm*—Townsend and Townsend and Crew LLP

(57) ABSTRACT

The present invention relates to nitrogen-containing heterocyclic quinoline compounds and pharmaceutically acceptable salts thereof which have inhibitory activity on the phosphorylation of kinases, which inhibits the activity of such kinases. The invention is also related to a method of inhibiting kinases and treating disease states in a mammal by inhibiting the phosphorylation of kinases. More particularly, the present invention provides nitrogen-containing heterocyclic compounds and pharmaceutically acceptable salts thereof which inhibit phosphorylation of a PDGF receptor to hinder abnormal cell growth and cell wandering, and a method for preventing or treating cell-proliferative diseases such as arteriosclerosis, vascular reobstruction, cancer and glomerulosclerosis.

5 Claims, No Drawings

NITROGENOUS HETEROCYCLIC SUBSTITUTED QUINOLINE COMPOUNDS

RELATED APPLICATIONS

This application claims the benefit of priority under 35 U.S.C. 119(e) to U.S. Provisional Application No. 60/273,951 filed on Mar. 8, 2001 which is herein incorporated in its entirety by reference.

FIELD OF INVENTION

The present invention relates to nitrogen-containing heterocyclic quinoline compounds and pharmaceutically acceptable salts thereof which have inhibitory activity on the phosphorylation of kinases, which inhibits the activity of such kinases. The invention is also related to a method of inhibiting kinases and treating disease states in a mammal by inhibiting the phosphorylation of kinases.

BACKGROUND OF THE INVENTION

The PDGF receptor-family of tyrosine kinases are known to act as aggravating signals for cell-proliferative diseases such as arteriosclerosis, vascular reobstruction after percutaneous coronary angioplasty and bypass operation, cancer, glomerulonephritis, glomerulosclerosis, psoriasis and articular rheumatism. See *Cell,* 46: 155–169 (1986); *Science,* 253:1129–1132 (1991); Nippon Rinsho (*Japanese J. of Clinical Medicine*), 50: 3038–3045 (1992); *Nephrol Dial Transplant,* 10: 787–795 (1995); *Kidney International,* 43 (Suppl. 39): 86–89 (1993); *Journal of Rheumatology,* 21: 1507–1511 (1994); *Scandinavian Journal of Immunology,* 27: 285–294 (1988), *Journal of Clinical Oncology,* 29–47 (1999), etc.

Certain 3-cyanoquinolines are known to be inhibitors of protein tyrosine kinases and are described in U.S. Pat. No. 6,002,008. More specifically, certain 3-cyanoquinolines are inhibitors of MEK (MAPKK), as described in *Bioorg. & Med. Chem. Lett.,* 10: 2825–2828 (2000) and WO 0068201; as src tyrosine kinase inhibitors as described in *Bioorg. & Med. Chem. Lett.,* 10: 2477–2480 (2000); and as EGF-receptor kinase inhibitors as described in *J. Med. Chem.,* 43: 3244–3256 (2000).

Quinoline derivatives having benzodiazepin receptor agonist activity are described in *Pharmacology Biochemistry and Behavior,* 53: 87–97 (1996) and *European Journal of Medicinal Chemistry,* 31: 417–425 (1996), and quinoline derivatives which are useful as anti-parasite agents are described in *Indian Journal of Chemistry,* 26B: 550–555 (1987).

Inhibitors of phosphorylation of PDGF receptor-family tyrosine kinases so far known include bismono- and bicyclic aryl compounds and heteroaryl compounds (WO 92/20642), quinoxaline derivatives. *Cancer Research,* 54: 6106 (1994), pyrimidine derivatives (Japanese Published Unexamined Patent Application No. 87834/94), phenylaminopyrimidine derivatives (EP-0564409-A1, WO-09509847 and U.S. Pat. No. 5,521,184) and dimethoxyquinoline derivatives. Abstracts of the 16th Annual Meeting of the Pharmaceutical Society of Japan (Kanazawa) (1996), 2, p. 275, 29(C2) 15–2.

SUMMARY OF THE INVENTION

The invention is directed to nitrogen-containing heterocyclic compounds and pharmaceutically acceptable salts thereof which have inhibitory activity on the phosphorylation of kinases, which inhibits the activity of the kinases. More particularly, important kinase inhibition according to the invention is of receptor tyrosine kinases including platelet-derived growth factor (PDGF) receptor, Flt3, CSF-1R, c-kit, epidermal growth factor receptor (EGRF), fibroblast growth factor (FGF), vascular endothelial growth factor receptor (VEGFR) and others. Another class of kinase inhibition according to the invention is inhibitory activity nonreceptor tyrosine kinases including src and abl, and the like. A third class of kinase inhibition according to the invention is inhibitory activity toward serine/threonine kinases, including such kinases as MAPK, MEK and cyclin dependent kinases (CDKs) that mediate cell prolifetation, AKT and CDK such that mediate cell survival and NIK that regulate inflammatory responses. Inhibition of such kinases can be used to treat diseases involving cell survival, proliferation and migration, including cardiovascular disease, such as arteriosclerosis and vascular reobstruction, cancer, glomerulosclerosis fibrotic diseases and inflammation, as well as the general treatment of cell-proliferative diseases.

Another aspect of the present invention relates to compounds and pharmaceutically acceptable salts thereof which inhibit or prevent phosphorylation of at least one PDGF receptor-family member. Such PDGF receptor-family kinase inhibitors can hinder abnormal cell growth and cell wandering, and thus such compounds are useful for the prevention or treatment of cell-proliferative diseases such as arteriosclerosis, vascular reobstruction, cancer and glomerulosclerosis.

Another aspect of the invention relates to nitrogen-containing heterocyclic quinoline compounds represented by general formula (I):

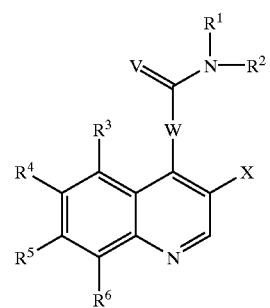

wherein:

V is a member selected from the group consisting of an oxygen atom, a sulfur atom and =N—CN;

W is 1,4-piperazinediyl or 1,4-homopiperazinedlyl in which carbons on the ring may be optionally substituted by 0 to 4 $C_1$ to $C_{16}$ alkyl groups which may be the same or different and each alkyl group my be independently substituted by 0–4 $R^a$ groups;

wherein $R^a$ is a member selected from the group consisting of halo, haloalkyl, —CN, —CN($R^b$, $R^c$),—N($R^b$, $R^c$), —C(=O)—N($R^b$, $R^c$), —NO$_2$, —SO$_2$N($R^b$, $R^c$), —SO$_2R^b$, —(CH$_2$)$_m$NR$^b$R$^c$, —(CH$_2$)$_m$—C(=NR$^b$)—R$^c$, —(CH$_2$)$_m$—C(=NR$^b$)—N (R$^b$,R$^c$), —(CH$_2$)$_m$—N (R$^b$)—C(=NR$^b$)—N(R$^b$,R$^c$), —(CH$_2$)$_m$, —NR$^b$—C$_{3-6}$ heterocyclics, —C$_{1-4}$alkyl, —C$_{2-6}$alkenyl, —C$_{2-6}$ alkynyl, —C$_{3-8}$cycloalkyl, —C$_{0-4}$alkylC$_{3-8}$cycloalkyl, —CF$_3$, —OR$^b$, and a 5–6 membered heterocyclic system containing from 1–4 heteroatoms selected from N, O and S, wherein from 1–4 hydrogen atoms on the heterocyclic system may be independently replaced with a member selected from the group consisting of halo, haloalkyl, —CN, CN($R^b$, $R^c$),—N($R^b$, $R^c$), —$C_{1-4}$ alkyl, —$C_{2-6}$alkenyl, —$C_{2-6}$alkynyl, —$C_{3-8}$ cycloalkyl, —$C_{0-4}$alkyl$C_{3-8}$cycloalkyl and —$NO_2$; wherein m is 0 to 2, $R^b$ and $R^c$ are each independently a member selected from the group consisting of —H, —$OR^d$, —N(—$R^d$, —$R^e$), —$C_{1-4}$alkyl —$C_{2-6}$alkenyl, —$C_{2-6}$ alkynyl, —$C_{3-8}$cycloalkyl, —$C_{0-4}$alkyl$C_{3-8}$ cycloalkyl, —$C_{0-4}$alkylphenyl and —$C_{0-4}$ alkylnaphthyl, wherein from the ring atoms of the phenyl and naphthyl moieties may be independently replaced with a member selected from the group consisting of halo, haloalkyl, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —$NO_2$, and $R^d$ and $R^e$ are each independently a member selected from the group consisting of —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl;

or $R^b$ and $R^c$ taken together with a carbon atom or nitrogen atom to which they are attached can form a 3–8 membered cycloalkyl or a heterocyclic ring system, wherein the heterocyclic ring system may have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, haloalkyl, —CN, —CN($R^b$, $R^c$), —N($R^b$, $R^c$), —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

X is a member selected from the group consisting of: H, T—Z, F and Cl; wherein Z is OH, CN or CHO;

$R^1$ is a member selected from the group consisting of:

a hydrogen atom, a $C_1$ to $C_{16}$ alkyl group which may be optionally substituted by 0 to 4 $R^{1a}$ groups, a $C_2$ to $C_{16}$ alkenyl group which may be optionally substituted by 0 to 4 $R^{1a}$ groups, a $C_2$ to $C_{16}$ cycloalkyl group which may be optionally substituted by 0 to 4 $R^{1a}$ groups, a partially or fully saturated monocyclic or bicyclic heterocyclic ring system having 5 to 10 ring atoms and 1 to 4 of the ring atoms is a member selected from the group consisting of O, S, and N, wherein the heterocylic ring system may be optionally substituted by 0 to 4 $R^{1a}$ groups, a heteroaryl ring system having 5 to 10 ring atoms and 1 to 4 of the ring atoms is a member selected from the group consisting of O, S, and N, wherein the heterocylic ring system may be optionally substituted by 0 to 4 $R^{1a}$ groups, and a heteroarylalkyl group having from 5 to 10 ring atoms and 1 to 16 carbon atoms in the alkyl portion, and 1 to 4 of the ring atoms is a member selected from the group consisting of O, S, and N, wherein the heteroaryl ring may be optionally substituted by 0 to 4 $R^{1a}$ groups, wherein $R^{1a}$ is a member selected from the group consisting of halo, haloalkyl, —CN, —CN($R^b$, $R^c$),—N($R^b$, $R^c$), —C(=O)—N($R^{1b}$, $R^{1c}$), —$NO_2$, —$SO_2$N($R^{1b}$, $R^{1c}$), —$SO_2R^{1b}$, —$(CH_2)_n NR^{1b}R^{1c}$, —$(CH_2)_n$—C(=$NR^{1b}$)—$R^{1c}$, —$(CH_2)_n$—C(=$NR^{1b}$)—N($R^{1b}$,$R^{1c}$), —$(CH_2)_n$—N($R^{1b}$)—C(=$NR^{1b}$)—N($R^{1b}$, $R^{1c}$), —$(CH_2)_n$—$NR^{1b}$—$C_{3-6}$heterocyclics, —$C_{1-4}$alkyl, —$C_{2-6}$alkenyl, —$C_{2-6}$alkynyl, —$C_{3-8}$cycloalkyl, —$C_{0-4}$ alkyl$C_{3-8}$cycloalkyl, —$CF_3$,—$OR^{1b}$, and a 5–6 membered heterocyclic system containing from 1–4 heteroatoms selected from N, O and S, wherein from 1–4 hydrogen atoms on the heterocyclic system may be independently replaced with a member selected from the group consisting of halo, haloalkyl, —CN, —N($R^b$, $R^c$),—N($R^b$, $R^c$), —$C_{1-4}$alkyl, —$C_{2-6}$alkenyl, —$C_{2-6}$ alkynyl, —$C_{3-8}$cycloalkyl, —$C_{0-4}$alkyl$C_{3-8}$cycloalkyl and —$NO_2$;

wherein n is 0 to 2, $R^{1b}$ and $R^{1c}$ are each independently a member selected from the group consisting of —H, —$OR^{1d}$, —N(—$R^{1d}$, —$R^{1e}$), —$C_{1-4}$alkyl, —$C_{2-6}$alkenyl, —$C_{2-6}$ alkynyl, —$C_{3-8}$cycloalkyl, —$C_{0-4}$alkyl$C_{3-8}$ cycloalkyl, —$C_{0-4}$alkylphenyl and —$C_{0-4}$ alkylnaphthyl, wherein from 1–4 hydrogen atoms on the ring atoms of the phenyl and naphthyl moieties may be independently replaced with a member selected from the group consisting of halo, haloalkyl, —$C_{1-4}$alkyl, —$C_{2-6}$alkenyl, —$C_{2-6}$alkynyl, —$C_{3-8}$ cycloalkyl, —$C_{0-4}$alkyl$C_{3-8}$cycloalkyl, —CN, and —$NO_2$, and $R^{1d}$ and $R^{1e}$ are each independently a member selected from the group consisting of —$C_{1-4}$ alkyl, —$C_{2-6}$alkenyl, —$C_{2-6}$alkynyl, —$C_{3-8}$ cycloalkyl, —$C_{0-4}$alkyl$C_{3-8}$cycloalkyl;

or $R^b$ and $R^c$ taken together with a carbon atom or nitrogen atom to which they are attached can form a 3–8 membered cycloalkyl or a heterocyclic ring system, wherein the heterocyclic ring system may optionally have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, haloalkyl, —CN, —CN($R^b$, $R^c$),—N($R^b$, $R^c$), —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

$R^2$ is a member selected from the group consisting of:

(a) a hydrogen atom, a $C_1$ to $C_{16}$ alkyl group which may be by 0 to 4 $R^{2a}$ groups, a $C_2$ to $C_{16}$ alkenyl group which may be by 0 to 4 $R^{2a}$ groups, a $C_2$ to $C_{16}$ cycloalkyl group which may be by 0 to 4 $R^{2a}$ groups, wherein $R^{2a}$ is a member selected rom the group consisting of halo, haloalkyl, —CN($R^b$, $R^c$), —CN($R^b$, $R^c$), —C(=O)—N($R^{2b}$, $R^{2c}$), —$NO_2$, —$SO_2$N($R^{2b}$, $R^{2c}$), —$SO_2R^{2b}$, —$(CH_2)_p NR^{2b}R^{2c}$, —$(CH_2)_p$—C(=$NR^{2b}$)—$R^{2c}$, —$(CH_2)_p$—C(=$NR^{2b}$)—N($R^{2b}$,$R^{2c}$), —$(CH_2)_p$—N($R^{2b}$)—C(=$NR^{2b}$)—N($R^{2b}$, $R^{2c}$), —$(CH_2)_p$—$NR^{2b}$—$C_{3-6}$heterocyclics, —$C_{1-4}$alkyl, —$C_{2-6}$alkenyl, —$C_{2-6}$alkynyl, —$C_{3-8}$cycloalkyl, —$C_{0-4}$ alkyl$C_{3-8}$cloalkyl, —$CF_3$, —$OR^{1b}$, and a 5–6 membered heterocyclic system containing from 1–4 heteroatoms selected from N, O and S, wherein from 1–4 hydrogen atoms on the heterocyclic system may be independently replaced with a member selected from the group consisting of halo, —CN, —$C_{1-4}$alkyl, —$C_{2-6}$ alkenyl, —$C_{2-6}$alkynyl, —$C_{3-8}$cycloalkyl, —$C_{0-4}$ alkyl$C_{3-8}$cycloalkyl and —$NO_2$;

wherein p is 0 to 2, $R^{2b}$ and $R^{2c}$ are each independently a member selected from the group consisting of —H, —$OR^{2d}$, —N(—$R^{2d}$, —$R^{2e}$), —$C_{1-4}$alkyl, —$C_{2-6}$alkenyl, —$C_{2-6}$ alkynyl, —$C_{3-8}$cycloalkyl, —$CO_4$alkyl$C_{3-8}$ cycloalkyl, —$CO_4$alkylphenyl and —$CO_4$alkylnaphthyl, wherein from 1–4 hydrogen atoms on the ring atoms of the phenyl and naphthyl moieties may be independently replaced with a member selected from the group consisting of halo, haloalkyl, —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl, —CN, and —NO$_2$, and $R^{2d}$ and $R^{2e}$ are each independently a member selected from the group consisting of —$C_{1-4}$alkyl, —$C_{2-6}$ alkenyl, —$C_{2-6}$alkynyl, —$C_{3-8}$cycloalkyl, —$C_{0-4}$ alkyl$C_{3-8}$cycloalkyl;

or $R^{2b}$ and $R^{2c}$ taken together with a carbon atom or nitrogen atom to which they are attached can form a 3–8 membered cycloalkyl or a heterocyclic ring system, wherein the heterocyclic ring system may optionally have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, haloalkyl, —CN, —CN($R^b$, $R^c$),—N($R^b$, $R^c$), —$C_{1-4}$alkyl, —$C_{2-6}$alkenyl, —$C_{2-6}$alkynyl, —$C_{3-8}$cycloalkyl, —$CO_4$alkyl$C_{3-8}$cycloalkyl and —NO$_2$;

(b) phenyl, which is independently substituted with 0–2 $R^{2a}$ substituents as defined above;

(c) naphthyl, which is independently substituted with 0–2 $R^{2a}$ substituents as defined above; and (d) a monocyclic or fused bicyclic heterocyclic ring system having from 5 to 10 ring atoms, wherein 1–4 ring atoms of the ring system are selected from N, O and S, and wherein the ring system may be optionally substituted with 0–2 $R^{2a}$ substituents as defined above;

(e) —C(=O)—$R^{10}$, wherein $R^{10}$ is independently a member defined the same as $R^1$ above;

(f) —S(=O)$_{1-2}$—$R^{11}$, wherein $R^{11}$ is independently a member defined the same as $R^1$ above, except that $R^{11}$ is other than hydrogen;

$R^3$, $R^4$, $R^5$ and $R^6$ are each independently a member selected from the group consisting of:

(a) a hydrogen atom, a halogen atom, an optionally substituted alkyl group, a nitro group, a cyano group, (b) —O—$R^{12}$, wherein $R^{12}$ is independently a member selected from the group as defined above for $R^{10}$;

(c) —C(=O)—$R^{13}$, wherein $R^{13}$ is independently a member selected from the group as defined above for $R^{10}$;

(d) —SO$_2R^{14}$, wherein $R^{14}$ is independently a member selected from the group as defined above for $R^{10}$;

(e) —N(—$R^{15}$, —$R^{16}$), wherein each of $R^{15}$ and $R^{16}$ are independently a member selected from the group as defined above for $R^{10}$, or $R^{15}$ and $R^{16}$ are combined together with the adjoining nitrogen atom to represent an optionally substituted nitrogen-containing heterocyclic ring system having from 5 to 10 ring atoms, wherein 1–4 ring atoms of the ring system are selected from N, O and S, and wherein the ring system may be optionally substituted with 0–2 substituents as defined above for $R^{2a}$;

(f) —SO$_2R^{17}$, wherein $R^{17}$ is independently a member selected from the group as defined above for $R^{10}$;

(g) a radical of the formula:

wherein
$X^1$ represents an oxygen atom or a sulfur atom;
$R^{18}$ is a member selected from the group consisting of
  (a) a member selected independently from the group as defined above for $R^{10}$;
  (b) —O—$R^{19}$, wherein $R^{19}$ is a member selected independently from the group as defined above for $R^{10}$; or
  (c) —N(—$R^{20}$, —$R^{21}$), wherein each of $R^{20}$ and $R^{21}$ is independently a member selected independently from the group as defined above for $R^{10}$, or $R^{20}$ and $R^{21}$ are combined together with the adjoining nitrogen atom to represent an optionally substituted nitrogen-containing heterocyclic ring system having from 5 to 10 ring atoms, wherein 1–4 ring atoms of the ring system are selected from N, O and S, and wherein the ring system may be optionally substituted with 0–2 substituents as defined above for $R^{2a}$;

(h) a radical of the formula:

wherein z is an integer from 0 to 2;
when z is 0,
  $R^{22}$ is a member selected independently from the group as defined above for $R^{10}$;
when z is 1,
  $R^{22}$ is a member selected independently from the group as defined above for $R^{11}$;
when z is 2,
  $R^{22}$ is a member selected from the group consisting of:
  (a) a member selected independently from the group as defined above for $R^{11}$;
  (b) —O—$R^{23}$, wherein $R^{23}$ is a a member selected independently from the group as defined above for $R^{10}$;
  (c) —N(—$R^{24}$, $R^{25}$), wherein $R^{24}$ and $R^{25}$ are each independently a member selected independently from the group as defined above for $R^{10}$, or $R^{24}$ and $R^{24}$ are combined together with the adjoining nitrogen atom to represent an optionally substituted nitrogen-containing heterocyclic ring system having from 5 to 10 ring atoms, wherein 1–4 ring atoms of the ring system are selected from N, O and S, and wherein the ring system may be optionally substituted with 0–2 substituents as defined above for $R^{2a}$;
  (d) —C(=O)—$R^{26}$, wherein $R^{26}$ is a member selected independently from the group as defined above for $R^{10}$, or $R^{26}$ is the group —O—$R^{27}$, wherein $R^{27}$ is a member selected independently from the group as defined above for $R^{10}$, or $R^{27}$ is the group —N(—$R^{28}$, —$R^{29}$), wherein $R^{28}$ and $R^{29}$ are each independently a member selected independently from the group as defined above for $R^{10}$ or, or $R^{28}$ and $R^{29}$ are combined together with the adjoining nitrogen atom to represent an optionally susbtituted nitrogen-containing heterocyclic ring system having from 5 to 10 ring atoms, wherein 1–4 ring atoms of the ring system are selected from N, O and S, and wherein the ring system may be optionally substituted with 0–2 substituents as defined above for $R^{2a}$; and wherein any two of $R^3$, $R^4$, $R^5$ and $R^6$ attached to adjoining carbons taken together with the carbon atom to which they are attached form a ring structure which is a member selected from the following:

(a) a 5 to 6 membered saturated heterocyclic ring having two oxygen ring atoms interrupted by one or two carbons, respectively;

(b) a or unsubstuted phenyl group; and (c) a heterocyclic ring which is a member selected from the following group:

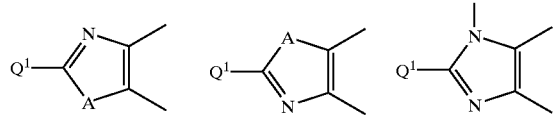

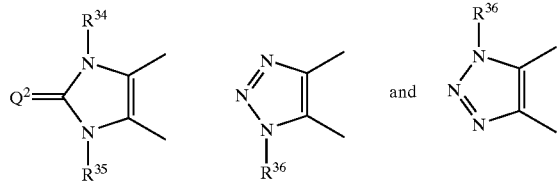

wherein:

A is an oxygen atom or a sulfur atom;

$Q^1$ is a member selected from the group consisting of:
(a) the group as defined above for $R^{10}$; or
(b) —N(—$R^{31}$, —$R^{32}$), wherein $R^{31}$ and $R^{32}$ are each independently a member selected independently from the group as defined above for $R^{10}$;
—O—$R^{33}$ or —S—$R^{33}$, wherein $R^{33}$ is a member selected independently from the group as defined above for $R^{10}$;

$Q^2$ is a member selected from the group consisting of =O, =S, or =N—CN; and $R^{30}$, $R^{34}$, $R^{35}$ and $R^{36}$ are each independently a member selected from the group as defined above for $R^{10}$; and and all pharmaceutically acceptable isomers, salts, hydrates, solvates and prodrug derivatives thereof.

In another aspect, the invention provides nitrogen-containing heterocyclic quinoline compounds represented by general formula (1):

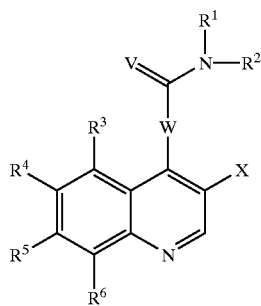

wherein:

V is a member selected from the group consisting of an oxygen atom, a sulfur atom and =N—CN;

W is 1,4-piperazinediyl or 1,4-homopiperazinediyl;

X is a member selected from the group consisting of: (—CH$_2$)$_{0-8}$—CH$_2$—OH, (—CH$_2$)$_{1-8}$—C(=O)—O(—CH$_2$)$_{0-8}$—CH$_3$, (—CH$_2$)$_{1-8}$—C(=O)—H, (—CH$_2$)$_{0-8}$—CN, F and Cl;

$R^1$ is a member selected from the group consisting of:
a hydrogen atom, a $C_1$ to $C_{16}$ alkyl group which may be optionally substituted by 0 to 4 $R^{1a}$ groups, a $C_2$ to $C_{16}$ alkenyl group which may be optionally substituted by 0 to 4 $R^{1a}$ groups, a $C_2$ to $C_{16}$ cycloalkyl group which may be optionally substituted by 0 to 4 $R^{1a}$ groups, a partially or fully saturated monocyclic or bicyclic heterocyclic ring system having 5 to 10 ring atoms and 1 to 4 of the ring atoms is a member selected from the group consisting of O, S, and N, wherein the heterocylic ring system may be optionally substituted by 0 to 4 $R^{1a}$ groups, a heteroaryl ring system having 5 to 10 ring atoms and 1 to 4 of the ring atoms is a member selected from the group consisting of O, S, and N, wherein the heterocylic ring system may be optionally substituted by 0 to 4 $R^{1a}$ groups, and a heteroarylalkyl group having from 5 to 10 ring atoms and 1 to 16 carbon atoms in the alkyl portion, and 1 to 4 of the ring atoms is a member selected from the group consisting of O, S, and N, wherein the heteroaryl ring is by 0 to 4 $R^{1a}$ groups, wherein $R^{1a}$ is a member selected from the group consisting of halo, haloalkyl, —CN, —CN ($R^b$, $R^c$),—N($R^b$, $R^c$), —C(=O)—N($R^{1b}$, $R^{1c}$), —NO$_2$, —SO$_2$N($R^{1b}$, $R^{1c}$), —SO$_2R^{1b}$, —(CH$_2$)$_n$NR$^{1b}$R$^{1c}$, —(CH$_2$)$_n$—C(=NR$^{1b}$)—R$^{1c}$, —(CH$_2$)$_n$—C(=NR$^{1b}$)—N($R^{1b}$, $R^{1c}$), —(CH$_2$)$_n$—N($R^{1b}$)—C(=NR$^{1b}$)—N($R^{1b}$, $R^{1c}$), —(CH$_2$)$_n$—NR$^{1b}$—C$_{3-6}$ heterocyclics, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CF$_3$, —OR$^{1b}$, and a 5–6 membered heterocyclic system containing from 1–4 heteroatoms selected from N, O and S, wherein from 1–4 hydrogen atoms on the heterocyclic system may be independently replaced with a member selected from the group consisting of halo, haloalkyl, —CN, —CN($R^b$, $R^c$),—N($R^b$, $R^c$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

wherein
n is 0 to 2,
$R^{1b}$ and $R^{1c}$ are each independently a member selected from the group consisting of —H, —OR$^{1d}$, —N(—

$R^{1d}$, —$R^{1e}$), —$C_{1-4}$alkyl, —$C_{2-6}$alkenyl, —$C_{2-6}$ alkynyl, —$C_{3-8}$cycloalkyl, —$C_{0-4}$alkyl$C_{3-8}$ cycloalkyl, —$C_{0-4}$alkylphenyl and —$C_{0-4}$ alkylnaphthyl, wherein from 1–4 hydrogen atoms on the ring atoms of the phenyl and naphthyl moieties may be independently replaced with a member selected from the group consisting of halo, —$C_{1-4}$ alkyl, —$C_{2-6}$alkenyl, —$C_{2-6}$alkynyl, —$C_{3-8}$ cycloalkyl, —$C_{0-4}$alkyl$C_{3-8}$cycloalkyl, —CN, and —$NO_2$, and $R^{1d}$ and $R^{1e}$ are each independently a member selected from the group consisting of —$C_{1-4}$ alkyl, —$C_{2-6}$alkenyl, —$C_{2-6}$alkynyl, —$C_{3-8}$ cycloalkyl, —$C_{0-4}$alkyl$C_{3-8}$cycloalkyl;

or $R^b$ and $R^c$ taken together with a carbon atom or nitrogen atom to which they are attached can form a 3–8 membered cycloalkyl or a heterocyclic ring system, wherein the heterocyclic ring system may optionally have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, haloalkyl, —CN, —CN($R^b$, $R^c$), —N($R^b$, $R^c$), —$C_{1-4}$alkyl, —$C_{2-6}$alkenyl, —$C_{2-6}$alkylnyl, —$C_{3-8}$cycloalkyl, —$C_{0-4}$alkyl$C_{3-8}$cycloalkyl and —$NO_2$;

$R^2$ is a member selected from the group consisting of:
(a) a hydrogen atom, a $C_1$ to $C_{16}$ alkyl group which may be optionally substituted by 0 to 4 $R^{2a}$ groups, a $C_2$ to $C_{16}$ alkenyl group which may be by 0 to 4 $R^{2a}$ groups, a $C_2$ to $C_{16}$ cycloalkyl group which may be optionally substituted by 0 to 4 $R^{2a}$ groups, wherein $R^{2a}$ is a member selected rom the group consisting of halo, haloalkyl, —CN, —CN($R^b$, $R^c$), —N($R^b$, $R^c$), —C(=O)—N($R^{2b}$, $R^{2c}$), —$NO_2$, —$SO_2$N($R^{2b}$, $R^{2c}$), —$SO_2R^{2b}$, —$(CH_2)_pNR^{2b}R^{2c}$, —$(CH_2)_p$—C(=$NR^{2b}$)—$R^{2c}$, —$(CH_2)_p$—C(=$NR^{2b}$)—N($R^{2b}$,$R^{2c}$), —$(CH_2)_p$—N($R^{2b}$)—C(=$NR^{2b}$)—N($R^{2b}$,$R^{2c}$), $(CH_2)_p$—$NR^{2b}$—$C_{3-6}$heterocyclics, —$C_{1-4}$alkyl, —$C_{2-6}$ alkenyl, —$C_{2-6}$alkynyl, —$C_{3-8}$cycloalkyl, —$C^{0-4}$ alkyl$C_{3-8}$cycloalkyl, —$CF_3$, —$OR^{1b}$, and a 5–6 membered heterocyclic system containing from 1–4 heteroatoms selected from N, O and S, wherein from 1–4 hydrogen atoms on the heterocyclic system may be independently replaced with a member selected from the group consisting of halo, haloalkyl, —CN, —CN($R^b$, $R^c$), —N($R^b$, $R^c$), —$C_{1-4}$alkyl, —$C_{2-6}$alkenyl, —$C_{2-6}$alkynyl, —$C_{3-8}$cycloalkyl, —$C_{0-4}$alkyl$C_{3-8}$ cycloalkyl and —$NO_2$;

wherein
p is 0 to 2,
$R^{2b}$ and $R^{2c}$ are each independently a member selected from the group consisting of —H, —$OR^{2d}$, —N(—$R^{2d}$, —$R^{2e}$), —$C_{1-4}$alkyl, —$C_{2-6}$ alkenyl, —$C_{2-6}$alkynyl, —$C_{3-8}$cycloalkyl, —$C_{0-4}$ alkyl$C_{3-8}$cycloalkyl, —$C_{0-4}$alkylphenyl and —$C_{0-4}$ alkylnaphthyl, wherein from 1–4 hydrogen atoms on the ring atoms of the phenyl and naphthyl moieties may be independently replaced with a member selected from the group consisting of halo, haloalkyl, —$C_{1-4}$alkyl, —$C_{2-6}$alkenyl, —$C_{2-6}$ alkynyl, —$C_{3-8}$cycloalkyl, —$C_{0-4}$ alkyl$C_{3-8}$ cycloalkyl, —CN, and —$NO_2$, and $R^{2d}$ and $R^{2e}$ are each independently a member selected from the group consisting of —$C_{1-4}$alkyl, —$C_{2-6}$ alkenyl, —$C_{2-6}$alkynyl, —$C_{3-8}$cycloalkyl, —$C_{0-4}$ alkyl$C_{3-8}$cycloalkyl;

or $R^{2b}$ and $R^{2c}$ taken together with a carbon atom or nitrogen atom to which they are attached can form a 3–8 membered cycloalkyl or a heterocyclic ring system, wherein the heterocyclic ring system may optionally have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, haloalkyl, —CN, —CN($R^b$, $R^c$),—N($R^b$, $R^c$), —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

(b) phenyl, which is independently substituted with 0–2 $R^{2a}$ substituents as defined above;
(c) naphthyl, which is independently substituted with 0–2 $R^{2a}$ substituents as defined above; and
(d) a monocyclic or fused bicyclic heterocyclic ring system having from 5 to 10 ring atoms, wherein 1–4 ring atoms of the ring system are selected from N, O and S, and wherein the ring system may be optionally substituted with 0–2 $R^{2a}$ substituents as defined above;
(e) —C(=O)—$R^{10}$, wherein $R^{10}$ is independently a member defined the same as $R^1$ above;
(f) —S(=O)$_{1-2}$—$R^{11}$, wherein $R^{11}$ is independently a member defined the same as $R^1$ above, except that $R^{11}$ is other than hydrogen;

$R^3$, $R^4$, $R^5$ and $R^6$ are each independently a member selected from the group consisting of:
(a) a hydrogen atom, a halogen atom, an optionally substituted alkyl group, a nitro group, a cyano group, and
(b) —O—$R^{12}$, wherein $R^{12}$ is independently a member selected from the group as defined above for $R^{10}$;
and all pharmaceutically acceptable isomers, salts, hydrates, solvates and prodrug derivatives thereof.

In another aspect, the present invention provides compound as described above for formula I, represented by formula Ia as follows:

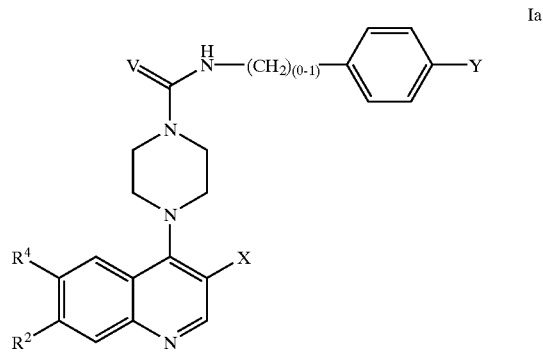

Ia wherein
V is a member selected from the group consisting of an oxygen atom or a sulfur atom; and =N—CN
X is a member selected from the group consisting of:
—$(CH_2)_{1-2}$—OH, —$CH_2$—C(=O)—O(—$CH_2$)$_{0-8}$—$CH_3$, —$CH_2$—C(=O)—H, and $(CH_2)_{0-1}$—CN, F, Cl
Y is a member selected from the group consisting of:
—CN, —Br, —$CF_3$, —O—$C_{1-8}$ alkyl that is independently straight or branched chained, —O-phenyl, —O-naphthyl, —O-indolyl and —O-isoquinolinyl;

$R^2$ and $R^4$ are each independently a member selected from the group consisting of:

—O—CH$_3$, —O(—CH$_2$)—CH$_3$, —O—CH$_2$—CH=CH$_2$, —O—CH$_2$—C≡CH and —O(CH$_2$)$_{2-3}$—R$^{2a}$;

$R^{2a}$ is a member selected from the group consisting of:
—OH, —O—CH$_3$, —O—CH$_2$—CH$_3$, —NH$_2$, —N(—CH$_3$)$_2$, —NH(—CH$_2$-phenyl), —NH(-Phenyl), —CN and all pharmaceutically acceptable isomers, salts, hydrates, solvates and prodrug derivatives thereof.

In another aspect, the present invention provides compound as described above for formula I, represented by formula Ia as follows:

Ia wherein

V is a member selected from the group consisting of an oxygen atom or a sulfur atom;

X is a member selected from the group consisting of:
—CN, CO$_2$Et, CHO, CH$_2$OH, F, Cl;

Y is a member selected from the group consisting of:
—CN, —O—C$_{1-8}$ alkyl that is independently straight or branched chained, —O-phenyl, —O-naphthyl, —O-indolyl and —O-isoquinolinyl;

$R^2$ and $R^4$ are each different and independently a member selected from the group consisting of:
—O—(CH$_2$—)$_{0-1}$—CH$_3$ and —O(—CH$_2$)$_{2-3}$—R$^{2a}$;

$R^{2a}$ is a member selected from the group consisting of:

and all pharmaceutically acceptable isomers, salts, hydrates, solvates and prodrug derivatives thereof.

Another aspect of the invention relates to pharmaceutically acceptable salts of the compounds according to formula (I) include pharmaceutically acceptable acid addition salts, metal salts, ammonium salts, organic amine addition salts, amino acid addition salts, etc.

Other aspects, objects, features and advantages of the present invention would be apparent to one of ordinary skill in the art from the following detailed description illustrating the preferred embodiments of the invention.

DETAILED DESCRIPTION OF THE INVENTION

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "C$_{3-16}$ carbocyclic mono, bicyclic or tricyclic ring structure" or the like are each intended to mean stable ring structures having only carbon atoms as ring atoms wherein the ring structure is a or un member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term " " as used in conjunction with carbocyclic ring structures means that hydrogen atoms attached to the ring carbon atoms of ring structures described herein may be by one or more of the substituents indicated for that structure if such substitution(s) would result in a stable compound.

The term "aryl" which is included with the term "carbocyclic ring structure" refers to an un or aromatic ring, with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally. Preferred aryl groups include phenyl, halophenyl, loweralkylphenyl, naphthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally.

As used herein, the term "heterocyclic ring" or "heterocyclic ring system" is intended to mean a or un member selected from the group consisting of stable monocyclic ring having from 5–7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be substituted by one or more of the indicated substituents if such replacement(s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocyclic and bicyclic heterocyclic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocyclic ring structures.

As used herein, the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom may be optionally substituted by a Cl, Br, F or I atom, including mixtures of different halo atoms. Trihaloalkyl includes trifluoromethyl and the like as preferred radicals, for example.

The term "methylene" refers to —$CH_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, amines including naturally occurring amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, pulines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

The "therapeutically effective amount" of a compound of the present invention will depend on the route of administration, the type of warm-blooded animal being treated, and the physical characteristics of the specific animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which as noted hose skilled in the medical arts will recognize.

The invention relates to nitrogen-containing heterocyclic quinoline compounds represented by general formula (I):

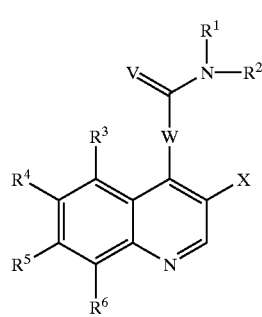

I wherein:

V is a member selected from the group consisting of an oxygen atom, a sulfur atom and =N—CN;

W is 1,4-piperazinediyl or 1,4-homopiperazinediyl in which carbons on the ring may be by 0 to 4 $C_1$ to $C_{16}$ alkyl groups which may be the same or different and each alkyl group my be independently substitituted by 0–4 $R^a$ groups;

wherein $R^a$ is a member selected from the group consisting of halo, haloalkyl, —CN, —CN($R^b$, $R^c$),—N($R^b$, $R^c$), —C(=O)—N($R^b$, $R^c$), —NO$_2$, —SO$_2$N($R^b$, $R^c$), —SO$_2R^b$, —(CH$_2$)$_m$NR$^b$R$^c$, —(CH$_2$)$_m$—C(=NR$^b$)—R$^c$, —(CH$_2$)$_m$—C(=NR$^b$)—N(R$^b$,R$^c$), —(CH$_2$)$_m$—N(R$^b$)—C(=NR$^b$)—N(R$^b$,R$^c$), —(CH$_2$)$_m$—NR$^b$—C$_{3-6}$ heterocyclics, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CF$_3$, —OR$^b$, and a 5–6 membered heterocyclic system containing from 1–4 heteroatoms selected from N, O and S, wherein from 1–4 hydrogen atoms on the heterocyclic system may be independently replaced with a member selected from the group consisting of halo, —CN, —C$_{1-4}$alkyl, —C$_{2-6}$alkenyl, —C$_{2-6}$alkynyl, —C$^{3-8}$cycloalkyl, —C$_{0-4}$alkylC$_{3-8}$cycloalkyl and —NO$_2$;

wherein
m is 0 to 2,
$R^b$ and $R^c$ are each independently a member selected from the group consisting of —H, —OR$^d$, —N(—R$^d$, —R$^e$), —C$_{1-4}$alkyl, —C$_{2-6}$alkenyl, —C$_{2-6}$alkynyl, —C$_{3-8}$cycloalkyl, -CO$_4$alkylC$_{3-8}$cycloalkyl, —C$_{0-4}$alkylphenyl and —C$_{0-4}$alkylnaphthyl, wherein from 1–4 hydrogen atoms on the ring atoms of the phenyl and naphthyl moieties may be independently replaced with a member selected from the group consisting of halo, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN, and —NO$_2$, and $R^d$ and $R^e$ are each independently a member selected from the group consisting of —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl;

or $R^b$ and $R^c$ taken together with a carbon atom or nitrogen atom to which they are attached can form a 3–8 membered cycloalkyl or a heterocyclic ring system, wherein the heterocyclic ring system may optionally have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, haloalkyl, —CN, —CN(R$^b$, R$^c$),—N(R$^b$, R$^c$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

X is a member selected from the group consisting of:
H, T—Z, F and Cl; wherein Z is OH, CN or CHO; T is $C_{1-16}$ alkylidene chain optionally interrupted by O , S, —C(=O)O, —OC(=O)—, —C=O;

$R^1$ is a member selected from the group consisting of:
a hydrogen atom, a $C_1$ to $C_{16}$ alkyl group which may be optionally substituted by 0 to 4 $R^{1a}$ groups, a $C_2$ to $C_{16}$ alkenyl group which may be optionally substituted by 0 to 4 $R^{1a}$ groups, a $C_2$ to $C_{16}$ cycloalkyl group which may be optionally substituted by 0 to 4 $R^{1a}$ groups, a partially or fully saturated monocyclic or bicyclic heterocyclic ring system having 5 to 10 ring atoms and 1 to 4 of the ring atoms is a member selected from the group consisting of O, S, and N, wherein the heterocylic ring system is by 0 to 4 $R^{1a}$ groups, a heteroaryl ring system having 5 to 10 ring atoms and 1 to 4 of the ring atoms is a member selected from the group consisting of O, S, and N, wherein the heterocylic ring system may be optionally substituted by 0 to 4 $R^{1a}$ groups, and a heteroarylalkyl group having from 5 to 10 ring atoms and 1 to 16 carbon atoms in the alkyl portion, and 1 to 4 of the ring atoms is a member selected from the group consisting of O, S, and N, wherein the heteroaryl ring may be optionally substituted by 0 to 4 $R^{1a}$ groups, wherein $R^{1a}$ is a member selected from the group consisting of halo, haloalkyl, —CN, —CN($R^b$, $R^c$),—N($R^b$, $R^c$), —C(=O)—N($R^{1b}$, $R^{1c}$), —NO$_2$, —SO$_2$N($R^{1b}$, $R^{1c}$), —SO$_2R^{1b}$, —(CH$_2$)$_n$NR$^{1b}$R$^{1c}$, —(CH$_2$)$_n$—C(=NR$^{1b}$)—R$^{1c}$, —(CH$_2$)$_n$—C(=NR$^{1b}$)—N(R$^{1b}$,R$^{1c}$), —(CH$_2$)$_n$—N(R$^{1b}$)—C(=NR$^{1b}$)—N(R$^{1b}$,R$^{1c}$), —(CH$_2$)$_n$—NR$^{1b}$—C$_{3-6}$ heterocyclics, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CF$_3$,—OR$^{1b}$, and a 5–6 membered heterocyclic system containing from 1–4 heteroatoms selected from N, O and S, wherein from 1–4 hydrogen atoms on the heterocyclic system may be independently replaced with a member selected from the group consisting of halo, haloalkyl, —CN, —CN($R^b$, $R^c$),—N($R^b$, $R^c$), —C$^{1-4}$alkyl, —C$_{2-6}$alkenyl, —C$_{2-6}$alkynyl, —C$_{3-8}$cycloalkyl, —C$_{0-4}$alkylC$_3$gcycloalkyl and —NO$_2$;

wherein n is 0 to 2, $R^{1b}$ and $R^{1c}$ are each independently a member selected from the group consisting of —H, —OR$^{1d}$, —N(—R$^{1d}$, —R$^{1e}$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —C$_{0-4}$alkylphenyl and —C$_{0-4}$alkylnaphthyl, wherein from 1–4 hydrogen atoms on the ring atoms of the phenyl and naphthyl moieties may be independently replaced with a member selected from the group consisting of halo, haloalkyl, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN, and —NO$_2$, and $R^{1d}$ and $R^{1e}$ are each independently a member selected from the group consisting of —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl;

or $R^b$ and $R^c$ taken together with a carbon atom or nitrogen atom to which they are attached can form a 3–8 membered cycloalkyl or a heterocyclic ring system, wherein the heterocyclic ring system may optionally have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, haloalkyl, —CN, —CN($R^b$, $R^c$),—N($R^b$, $R^c$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

$R^2$ is a member selected from the group consisting of:

(g) a hydrogen atom, a $C_1$ to $C_{16}$ alkyl group which may be optionally substituted by 0 to 4 $R^{2a}$ groups; a $C_2$ to $C_{16}$ alkenyl group which may be optionally substituted by 0 to 4 $R^{2a}$ groups, a $C_2$ to $C_{16}$ cycloalkyl group which may be optionally substituted by 0 to 4 $R^{2a}$ groups, wherein $R^{2a}$ is a member selected rom the group consisting of halo, haloalkyl, —CN, —CN($R^b$, $R^c$),—N($R^b$, $R^c$), —C(=O)—N($R^{2b}$, $R^{2c}$), —NO$_2$, —SO$_2$N($R^{2b}$, $R^{2c}$), —SO$_2R^{2b}$, —(CH$_2$)$_p$NR$^{2b}$R$^{2c}$, —(CH$_2$)$_p$—C(=NR$^{2b}$)—R$^{2c}$, —(CH$_2$)$_p$—C(=NR$^{2b}$)—N(R$^{2b}$,R$^{2c}$), —(CH$_2$)$_p$—N(R$^{2b}$)—C(=NR$^{2b}$)—N(R$^{2b}$,R$^{2c}$), —(CH$_2$)$_p$—NR$^{2b}$—C$_{3-6}$ heterocyclics, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CF$_3$, —OR$^{1b}$, and a 5–6 membered heterocyclic system containing from 1–4 heteroatoms selected from N, O and S, wherein from 1–4 hydrogen atoms on the heterocyclic system may be independently replaced with a member selected from the group consisting of halo, haloalkyl, —CN, —CN($R^b$, $R^c$),—N($R^b$, $R^c$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

wherein p is 0 to 2, $R^{2b}$ and $R^{2c}$ are each independently a member selected from the group consisting of —H, —OR$^{2d}$, —N(—R$^{2d}$, —R$^{2e}$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —C$_{0-4}$alkylphenyl and —C$_{0-4}$ alkylnaphthyl, wherein from 1–4 hydrogen atoms on the ring atoms of the phenyl and naphthyl moieties may be independently replaced with a member selected from the group consisting of halo, haloalkyl, —C$_{1-4}$alkyl, —C$_{2-6}$alkenyl, —C$_{2-6}$ alkynyl, —C$_{3-8}$cycloalkyl, —C$_{0-4}$alkylC$_{3-8}$ cycloalkyl, —CN, and —NO$_2$, and $R^{2d}$ and $R^{2e}$ are each independently a member selected from the group consisting of —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl;

or $R^{2b}$ and $R^{2c}$ taken together with a carbon atom or nitrogen atom to which they are attached can form a 3–8 membered cycloalkyl or a heterocyclic ring system, wherein the heterocyclic ring system may optionally have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, haloalkyl, —CN, —CN($R^b$, $R^c$),—N($R^b$, $R^c$),—C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;

(h) phenyl, which is independently substituted with 0–2 $R^{2a}$ substituents as defined above;

(i) naphthyl, which is independently substituted with 0–2 $R^{2a}$ substituents as defined above; and (j) a monocyclic or fused bicyclic heterocyclic ring system having from 5 to 10 ring atoms, wherein 1–4 ring atoms of the ring system are selected from N, O and S, and wherein the ring system may be optionally substituted with 0–2 $R^{2a}$ substituents as defined above;

(k) —C(=O)—R$^{10}$, wherein R$^{10}$ is independently a member defined the same as $R^1$ above;

(l) —S(=O)$_{1-2}$—R$^{11}$, wherein R$^{11}$ is independently a member defined the same as $R^1$ above, except that R$^{11}$ is other than hydrogen;

$R^3$, $R^4$, $R^5$ and $R^6$ are each independently a member selected from the group consisting of:

(a) a hydrogen atom, a halogen atom, an optionally substituted alkyl group, a nitro group, a cyano group, (b) —O—R$^{12}$, wherein R$^{12}$ is independently a member selected from the group as defined above for R$^{10}$;

(c) —C(=O)—$R^{13}$, wherein $R^{13}$ is independently a member selected from the group as defined above for $R^{10}$;

(d) —$SO_2R^{14}$, wherein $R^{14}$ is independently a member selected from the group as defined above for $R^{10}$;

(e) —N(—$R^{15}$, —$R^{16}$), wherein each of $R^{15}$ and $R^{16}$ are independently a member selected from the group as defined above for $R^{10}$, or $R^{15}$ and $R^{16}$ are combined together with the adjoining nitrogen atom to represent an optionally substituted nitrogen-containing heterocyclic ring system having from 5 to 10 ring atoms, wherein 1–4 ring atoms of the ring system are selected from N, O and S, and wherein the ring system may be optionally substituted with 0–2 substituents as defined above for $R^{2a}$;

(f) —$SO_2R^{17}$, wherein $R^{17}$ is independently a member selected from the group as defined above for $R^{10}$;

(g) a radical of the formula:

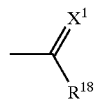

wherein
$X^1$ represents an oxygen atom or a sulfur atom;
$R^{18}$ is a member selected from the group consisting of
(a) a member selected independently from the group as defined above for $R^{10}$;
(b) —O—$R^{19}$, wherein $R^{19}$ is a member selected independently from the group as defined above for $R_{10}$; or
(c) —N(—$R^{20}$, —$R^{21}$), wherein each of $R^{20}$ and $R^{21}$ is independently a member selected independently from the group as defined above for $R^{10}$, or $R^{20}$ and $R^{21}$ are combined together with the adjoining nitrogen atom to represent an optionally substituted nitrogen-containing heterocyclic ring system having from 5 to 10 ring atoms, wherein 1–4 ring atoms of the ring system are selected from N, O and S, and wherein the ring system may be optionally substituted with 0–2 substituents as defined above for $R^{2a}$;

(h) a radical of the formula:

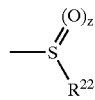

wherein z is an integer from 0 to 2;
when z is 0,
$R^{22}$ is a member selected independently from the group as defined above for $R^{10}$;
when z is 1,
$R^{22}$ is a member selected independently from the group as defined above for $R^{11}$;
when z is 2,
$R^{22}$ is a member selected from the group consisting of:
(e) a member selected independently from the group as defined above for $R^{11}$;
(f) —O—$R^{23}$, wherein $R^{23}$ is a a member selected independently from the group as defined above for $R^{10}$;
(g) —N(—$R^{24}$, $R^{25}$), wherein $R^{24}$ and $R^{25}$ are each independently a member selected independently from the group as defined above for $R^{10}$, or $R^{24}$ and $R^{24}$ are combined together with the adjoining nitrogen atom to represent an optionally substituted nitrogen-containing heterocyclic ring system having from 5 to 10 ring atoms, wherein 1–4 ring atoms of the ring system are selected from N, O and S, and wherein the ring system may be optionally substituted with 0–2 substituents as defined above for $R^{2a}$;

(h) —C(=O)—$R^{26}$, wherein $R^{26}$ is a member selected independently from the group as defined above for $R^{10}$, or $R^{26}$ is the group —O—$R^{27}$, wherein $R^{27}$ is a member selected independently from the group as defined above for $R^{10}$, or $R^{27}$ is the group —N(—$R^{28}$, —$R^{29}$), wherein $R^{28}$ and $R^{29}$ are each independently a member selected independently from the group as defined above for $R^{10}$ or, or $R^{28}$ and $R^{29}$ are combined together with the adjoining nitrogen atom to represent an optionally substituted nitrogen-containing heterocyclic ring system having from 5 to 10 ring atoms, wherein 1–4 ring atoms of the ring system are selected from N, O and S, and wherein the ring system may be optionally substituted with 0–2 substituents as defined above for $R^{2a}$; and wherein any two of $R^3$, $R^4$, $R^5$ and $R^6$ attached to adjoining carbons taken together with the carbon atom to which they are attached form a ring structure which is a member selected from the following:

(d) a 5 to 6 membered saturated heterocyclic ring having two oxygen ring atoms interrupted by one or two carbons, respectively;
(e) an optionally substituted phenyl group; and
(f) a heterocyclic ring which is a member selected from the following group:

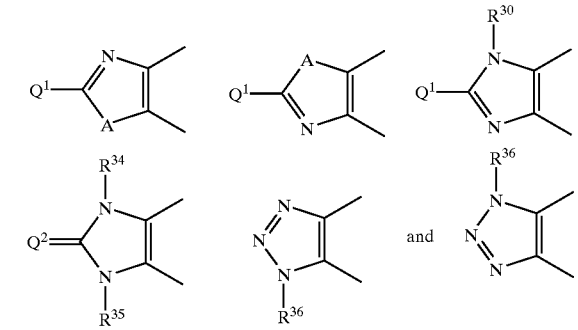

wherein:
A is an oxygen atom or a sulfur atom;
$Q^1$ is a member selected from the group consisting of:
(a) the group as defined above for $R^{10}$; or
(b) —N(—$R^{31}$, —$R^{32}$), wherein $R^{31}$ and $R^{32}$ are each independently a member selected independently from the group as defined above for $R^{10}$;
—O—$R^{33}$ or —S—$R^{33}$, wherein $R^{33}$ is a member selected independently from the group as defined above for $R^{10}$;
$Q^2$ is a member selected from the group consisting of =O, =S, =N—CN; and
$R^{30}$, $R^{34}$, $R^{35}$ and $R^{36}$ are each independently a member selected from the group as defined above for $R^{10}$; and and all pharmaceutically acceptable isomers, salts, hydrates, solvates and prodrug derivatives thereof.

Another embodiment of the invention provides nitrogen-containing heterocyclic quinoline compounds represented by general formula (I):

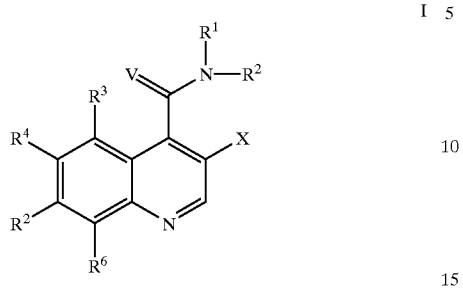

wherein:
V is a member selected from the group consisting of an oxygen atom, a sulfur atom and =N—CN;
W is 1,4-piperazinediyl or 1,4-homopiperazinediyl;
X is a member selected from the group consisting of:
(—CH$_2$)$_{0-8}$—CH$_2$—OH,
(—CH$_2$)$_{1-8}$—C(=O)—O(—CH$_2$)$_{0-8}$—CH$_3$, (—CH$_2$)$_{1-8}$—C(=O)—H, (—CH$_2$)$_{0-8}$—CN, F and Cl;
R$^1$ is a member selected from the group consisting of:
a hydrogen atom, a C$_1$ to C$_{16}$ alkyl group which may be optionally substituted by 0 to 4 R$^{1a}$ groups, a C$_2$ to C$_{16}$ alkenyl group which may be optionally substituted by 0 to 4 R$^{1a}$ groups, a C$_2$ to C$_{16}$ cycloalkyl group which may be optionally substituted by 0 to 4 R$^{1a}$ groups, a partially or fully saturated monocyclic or bicyclic heterocyclic ring system having 5 to 10 ring atoms and 1 to 4 of the ring atoms is a member selected from the group consisting of O, S, and N, wherein the heterocylic ring system may be optionally substituted by 0 to 4 R$^{1a}$ groups, a heteroaryl ring system having 5 to 10 ring atoms and 1 to 4 of the ring atoms is a member selected from the group consisting of O, S, and N, wherein the heterocyclic ring system may be optionally substituted by 0 to 4 R$^{1a}$ groups, and a heteroarylalkyl group having from 5 to 10 ring atoms and 1 to 16 carbon atoms in the alkyl portion, and 1 to 4 of the ring atoms is a member selected from the group consisting of O, S, and N, wherein the heteroaryl ring may be optionally substituted by 0 to 4 R$^{1a}$ groups, wherein R$^{1a}$ is a member selected from the group consisting of halo, haloalkyl, —CN, —CN(R$^b$, R$^c$),—N(R$^b$, R$^c$), —C(=O)—N(R$^{1b}$, R$^{1c}$), —NO$_2$, —SO$_2$N(R$^{1b}$, R$^{1c}$), —SO$_2$R$^{1b}$, —(CH$_2$)$_n$NR$^{1b}$R$^{1c}$, —(CH$_2$)$_n$—C(=NR$^{1b}$)—R$^{1c}$, —(CH$_2$)$_n$—C(=NR$^{1b}$)—N(R$^{1b}$,R$^{1c}$), —(CH$_2$)$_n$—N(R$^{1b}$)—C(=NR$^{1b}$)—N(R$^{1b}$,R$^{1c}$), —(CH$_2$)$_n$—NR$^{1b}$—C$_{3-6}$ heterocyclics, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CF$_3$, —OR$^{1b}$, and a 5–6 membered heterocyclic system containing from 1–4 heteroatoms selected from N, O and S, wherein from 1–4 hydrogen atoms on the heterocyclic system may be independently replaced with a member selected from the group consisting of halo, haloalkyl, —CN, —CN(R$^b$, R$^c$),—N(R$^b$, R$^c$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;
wherein
n is 0 to 2,
R$^{1b}$ and R$^{1c}$ are each independently a member selected from the group consisting of —H, —OR$^{1d}$, —N(—R$^{1d}$, R$^{1e}$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —C$_{0-4}$alkylphenyl and —C$_{0-4}$alkylnaphthyl, wherein from 1–4 hydrogen atoms on the ring atoms of the phenyl and naphthyl moieties may be independently replaced with a member selected from the group consisting of halo, haloalkyl, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN, and —NO$_2$, and R$^{1d}$ and R$^{1e}$ are each independently a member selected from the group consisting of —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl;
or R$^b$ and R$^c$ taken together with a carbon atom or nitrogen atom to which they are attached can form a 3–8 membered cycloalkyl or a heterocyclic ring system, wherein the heterocyclic ring system may optionally have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, haloalkyl, —CN, —CN(R$^b$, R$^c$),—N(R$^b$, R$^c$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;
R$^2$ is a member selected from the group consisting of:
(g) a hydrogen atom, a C$_1$ to C$_{16}$ alkyl group which may be optionally substituted by 0 to 4 R$^{2a}$ groups, a C$_2$ to C$_{16}$ alkenyl group which may be optionally substituted by 0 to 4 R$^{2a}$ groups, a C$_2$ to C$_{16}$ cycloalkyl group which may be optionally substituted by 0 to 4 R$^{2a}$ groups, wherein R$^2$, is a member selected rom the group consisting of halo, haloalkyl, —CN, —CN(R$^b$, R$^c$),—N(R$^b$, R$^c$), —C(=O)—N(R$^{2b}$, R$^{2c}$), —NO$_2$, —SO$_2$N(R$^{2b}$, R$^{2c}$), —SO$_2$R$^{2b}$, —(CH$_2$)$_p$NR$^{2b}$R$^{2c}$, —(CH$_2$)$_p$—C(=NR$^{2b}$)—R$^{2c}$, —(CH$_2$)$_p$—C(=NR$^{2b}$)—N(R$^{2b}$,R$^{2c}$), —(CH$_2$)$_p$—N(R$^{2b}$)—C(=NR$^{2b}$)—N(R$^{2b}$,R$^{2c}$), —(CH$_2$)$_p$—NR$^{2b}$—C$_{3-6}$ heterocyclics, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CF$_3$, —OR$^{1b}$, and a 5–6 membered heterocyclic system containing from 1–4 heteroatoms selected from N, O and S, wherein from 1–4 hydrogen atoms on the heterocyclic system may be independently replaced with a member selected from the group consisting of halo, haloalkyl, —CN, —CN(R$^b$, R$^c$),—N(R$^b$, R$^c$), —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl and —NO$_2$;
wherein
p is 0 to 2,
R$^{2b}$ and R$^{2c}$ are each independently a member selected from the group consisting of —H, —OR$^{2d}$, —N(—R$^{2d}$, R$^{2e}$), C$_{1-4}$alkyl, —C$_{2-6}$alkenyl, —C$_{2-6}$alkynyl, —C$_{3-8}$cycloalkyl, -C$_{0-4}$alkylC$_{3-8}$cycloalkyl, —C$_{0-4}$alkylphenyl and —C$_{0-4}$ alkylnaphthyl, wherein from 1–4 hydrogen atoms on the ring atoms of the phenyl and naphthyl moieties may be independently replaced with a member selected from the group consisting of halo, haloalkyl, —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl, —CN, and —NO$_2$, and R$^{2d}$ and R$^{2e}$ are each independently a member selected from the group consisting of —C$_{1-4}$alkyl, —C$_{2-6}$alkenyl, —C$_{2-6}$alkynyl, —C$_{3-8}$cycloalkyl, —C$_{0-4}$alkylC$_{3-8}$cycloalkyl;
or R$^{2b}$ and R$^{2c}$ taken together with a carbon atom or nitrogen atom to which they are attached can form a 3–8 membered cycloalkyl or a heterocyclic ring system, wherein the heterocyclic ring system may optionally have from 3 to 10 ring atoms, with 1 to 2 rings being in the ring system and contain from 1–4 heteroatoms selected from N, O and S, wherein from 1–4 hydrogen atoms on the heterocyclic ring system may be independently replaced with a member selected from the group consisting of halo, haloalkyl, —CN, —CN($R^b$, $R^c$),—N($R^b$, $R^c$), —$C_{1-4}$alkyl, —$C_{2-6}$alkenyl, —$C_{2-6}$alkynyl, —$C_{3-8}$cycloalkyl, —$C_{0-4}$alkyl$C_{3-8}$cycloalkyl and —$NO_2$;

(h) phenyl, which is independently substituted with 0–2 $R^{2a}$ substituents as defined above;
(i) naphthyl, which is independently substituted with 0–2 $R^{2a}$ substituents as defined above; and
a monocyclic or fused bicyclic heterocyclic ring system having from 5 to 10 ring atoms, wherein 1–4 ring atoms of the ring system are selected from N, O and S, and wherein the ring system may be optionally substituted with 0–2 $R^{2a}$ substituents as defined above;
(k) —C(=O)—$R^{10}$, wherein $R^{10}$ is independently a member defined the same as $R^1$ above;
(l) —S(=O)$_{1-2}$—$R^{11}$, wherein $R^{11}$ is independently a member defined the same as $R^1$ above, except that $R^{11}$ is other than hydrogen;

$R^3$, $R^4$, $R^5$ and $R^6$ are each independently a member selected from the group consisting of:
(a) a hydrogen atom, a halogen atom, an optionally substituted alkyl group, a nitro group, a cyano group, and
(b) —O—$R^{12}$, wherein $R^{12}$ is independently a member selected from the group as defined above for $R^{10}$;

and all pharmaceutically acceptable isomers, salts, hydrates, solvates and prodrug derivatives thereof.

Another embodiment of the invention provides nitrogen-containing heterocyclic quinoline compounds represented by general formula (I): (—$CH_2$)$_{0-1}$—$CH_2$—OH, (—$CH_2$)$_{1-2}$—C(=O)—O(—$CH_2$)$_{0-8}$—$CH_3$, (—$CH_2$)$_{1-2}$—C(=O)—H, (—$CH_2$)$_{0-1}$—CN, F and Cl;

In a preferred embodiment, the present invention provides compound as described above for formula I, represented by formula Ia as follows:

Ia wherein

V is a member selected from the group consisting of an oxygen atom, a sulfur atom and =N—CN
X is a member selected from the group consisting of:
—(CH$_2$)$_{1-2}$—OH, —CH$_2$—C(=O)—O(—CH$_2$)$_{0-8}$—CH$_3$, —CH$_2$—C(=O)—H, and (—CH$_2$)$_{0-1}$—CN, F, Cl;
Y is a member selected from the group consisting of:
—CN, —Br, —CF$_3$, —O—$C_{1-8}$ alkyl that is independently straight or branched chained, —O-phenyl, —O-naphthyl, —O-indolyl and —O-isoquinolinyl;

$R^2$ and $R^4$ are each independently a member selected from the group consisting of:
—O—CH$_3$, —O(—CH$_2$)—CH$_3$, —O—CH$_2$—CH=CH$_2$, —O—CH$_2$—C≡CH and —O(—CH$_2$)$_{2-3}$—R$^{2a}$;
$R^{2a}$ is a member selected from the group consisting of:
—OH, —O—CH$_3$, —O—CH$_2$—CH$_3$, —NH$_2$, —N(—CH$_3$)$_2$, —NH(—CH$_2$-phenyl), —NH(-Phenyl), —CN, and all pharmaceutically acceptable isomers, salts, hydrates, solvates and prodrug derivatives thereof.

In another embodiment, the present invention provides compound as described above for formula I, represented by formula Ia as follows:

Ia wherein

V is a member selected from the group consisting of an oxygen atom and a sulfur atom;
X is a member selected from the group consisting of:
—CN, CO$_2$Et, CHO, CH$_2$OH, F, and Cl;
Y is a member selected from the group consisting of:
—CN, —O—C$_{1-8}$ alkyl that is independently straight or branched chained, —O-phenyl, —O-naphthyl, —O-indolyl and —O-isoquinolinyl;
$R^2$ and $R^4$ are each different and independently a member selected from the group consisting of:
—O—(CH$_2$—)$_{0-1}$—CH$_3$ and —O(—CH$_2$)$_{2-3}$—R$^{2a}$;

$R^{2a}$ is a member selected from the group consisting of:

and all pharmaceutically acceptable isomers, salts, hydrates, solvates and prodrug derivatives thereof.

Another embodiment of the invention relates to pharmaceutically acceptable salts of the compounds according to formula (I) include pharmaceutically acceptable acid addition salts, metal salts, ammonium salts, organic amine addition salts, amino acid addition salts, etc.

Examples of the pharmaceutically acceptable acid addition salts of the compounds of formula (I) are inorganic acid addition salts such as hydrochloride, sulfate and phosphate, and organic acid addition salts such as acetate, maleate, fumarate, tartrate, citrate and methanesulfonate.

Examples of the pharmaceutically acceptable metal salts are alkali metal salts such as sodium salt and potassium salt, alkaline earth metal salts such as magnesium salt and calcium salt, aluminum salt and zinc salt. Examples of the pharmaceutically acceptable ammonium salts are ammonium salt and tetramethyl ammonium salt. Examples of the pharmaceutically acceptable organic amine addition salts include heterocyclic amine salts such as morpholine and piperidine salts. Examples of the pharmaceutically acceptable amino acid addition salts are salts with lysine, glycine and phenylalanine.

In a preferred embodiment the invention provides compounds according to formula II(a) and formula II(b) as follows:

Formula II(a)

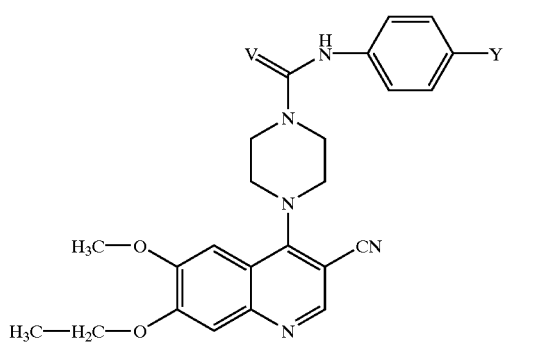

Formula II(b)

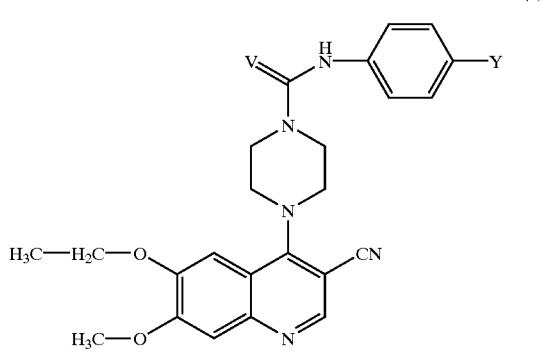

wherein:
V is an oxygen atom, a sulfur atom and =N—CN;
Y is a member selected from the group consisting of:
—CN, —Br, —CF$_3$, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy;

and all pharmaceutically acceptable isomers, salts, hydrates, solvates and prodrug derivatives thereof.

In another preferred embodiment the invention provides compounds according to formula (IIc) and formula (IId) as follows:

Formula II(c)

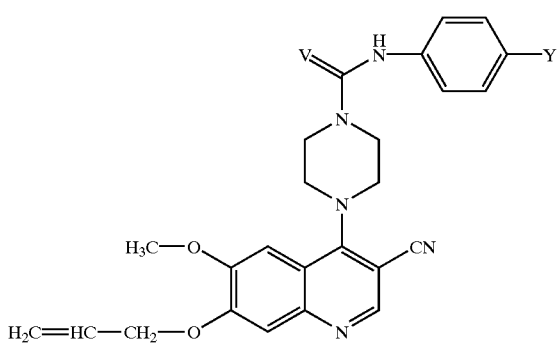

Formula II(d)

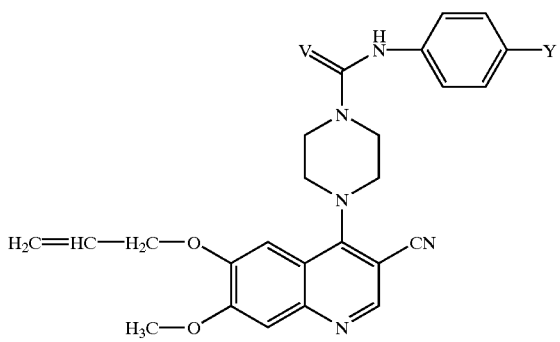

wherein
V is an oxygen atom or a sulfur atom; and
Y is a member selected from the group consisting of:
—CN, —Br, —CF$_3$, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy;

and all pharmaceutically acceptable isomers, salts, hydrates, solvates and prodrug derivatives thereof.

In still another preferred embodiment the invention provides compounds according to formula II(e) and formula II(f) as follows:

Formula II(e)

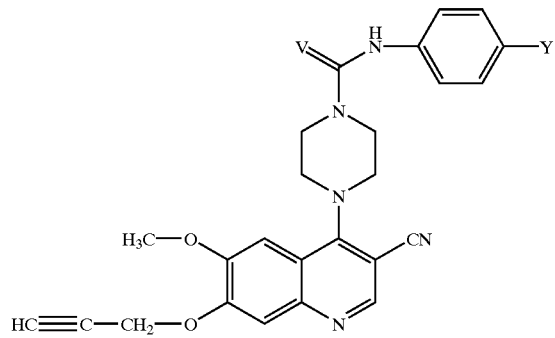

Formula II(f)

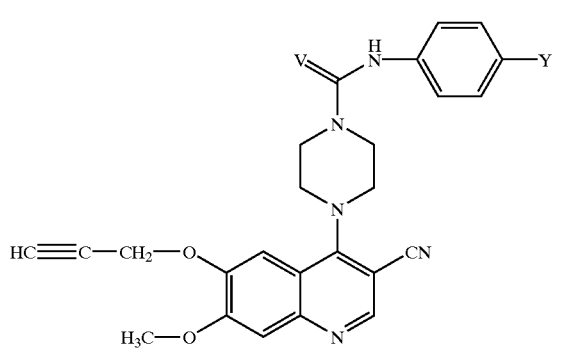

wherein
V is an oxygen atom or a sulfur atom; and
Y is a member selected from the group consisting of:
—CN, —Br, —CF$_3$, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy;
and all pharmaceutically acceptable isomers, salts, hydrates, solvates and prodrug derivatives thereof.

In yet another preferred embodiment the invention provides compounds according to formula II(g) and formula II(h) as follows:

Formula II(g)

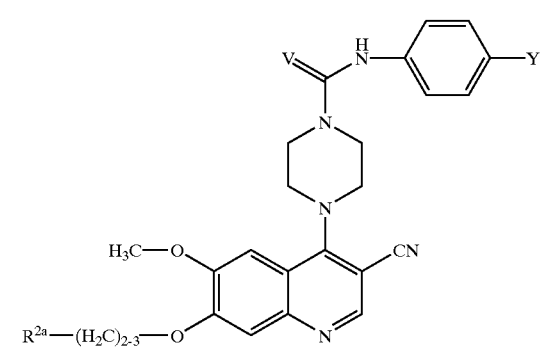

Formula II(h)

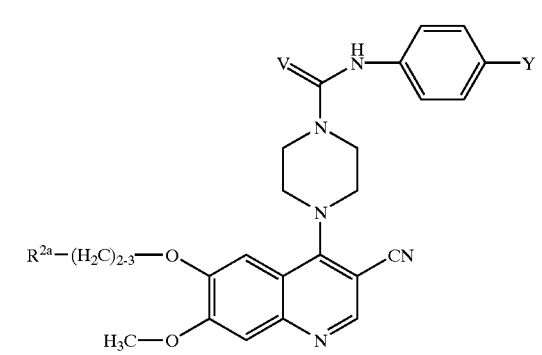

wherein
V is an oxygen atom or a sulfur atom;
Y is a member selected from the group consisting of:
—CN, —Br, —CF$_3$, —O-methyl, —O-ethyl, —O-propyl, —O-isopropyl, —O-butyl, —O-t-butyl, —O-isoamyl, 1-naphthyloxy, 2-naphthyloxy, 4-indolyloxy, 5-indolyloxy, 5-isoquinolyloxy;

$R^{2a}$ is a member selected from the group consisting of:
—OH, —O—CH$_3$, —O—CH$_2$—CH$_3$, —NH$_2$, —N(—CH$_3$)$_2$, —NH(—CH$_2$-phenyl), —NH(-Phenyl), —CN, and all pharmaceutically acceptable isomers, salts, hydrates, solvates and prodrug derivatives thereof.

The pharmaceutically acceptable salts of the compounds according to the above formulae include pharmaceutically acceptable acid addition salts, metal salts, ammonium salts, organic amine addition salts, amino acid addition salts, etc.

The present invention is not limited by the above listed compounds. Analogs of the bicyclic compounds are contemplated.

Further, an especially preferred embodiment of the present invention provides a compound as described above, which is selected from the group consisting of:

N-(4-indol-5-yloxyphenyl){4-[3-cyano-6-methoxy-7-(2-methoxyethoxy)quinolin-4-yl]piperazinyl}carboxamide

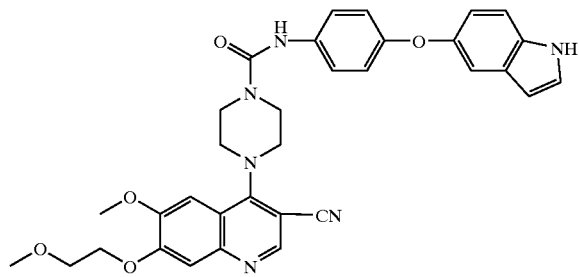

N-(4-indol-4-yloxyphenyl){4-[3-cyano-6-methoxy-7-(2-methoxyethoxy)quinolin-4-yl]piperazinyl}carboxamide

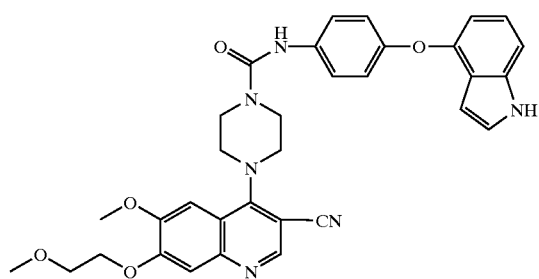

{4-[3-cyano-6-methoxy-7-(2-methoxyethoxy)quinolin-4-yl]piperazinyl}-N-(4-phenoxyphenyl)carboxamide

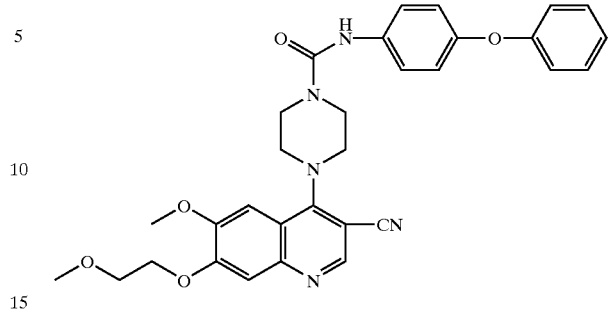

{4-[3-cyano-6-methoxy-7-(2-methoxyethoxy)quinazolin-4-yl]piperazinyl}-N-(4-naphthyloxyphenyl)carboxamide

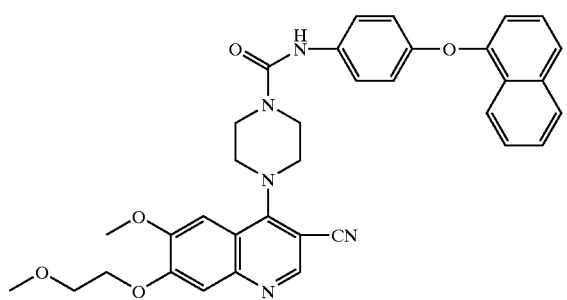

{4-[3-cyano-6-methoxy-7-(2-methoxyethoxy)quinolin-4-yl]piperazinyl}-N-[4-(methylethoxy)phenyl]carboxamide

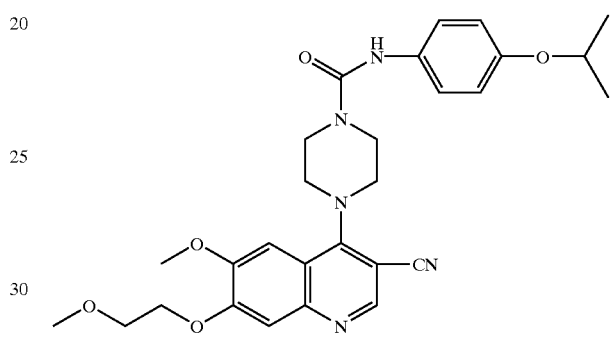

{4-[3-cyano-6-methoxy-7-(2-methoxyethoxy)quinolin-4-yl]piperazinyl}-N-(4-(2-naphthyloxy)phenyl)carboxamide

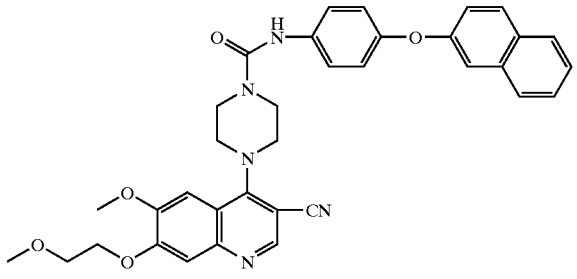

N-(4-cyanophenyl){4-[3-cyano-6-methoxy-7-(2-methoxyethoxy)quinolin-4-yl]piperazinyl}carboxamide

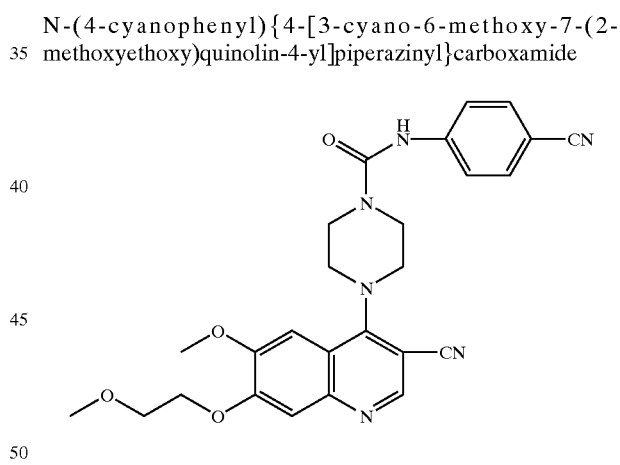

N-(4-(5-isoquinolyloxy)phenyl){4-[3-cyano-6-methoxy-7-(2-methoxyethoxy) quinolin-4-yl]piperazinyl}carboxamide

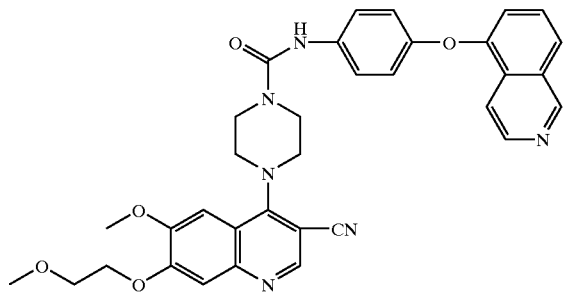

{4-[3-cyano-6-methoxyl)quinolin-4-yl]piperazinyl}-N-[4-(methylethoxy)phenyl]carboxamide

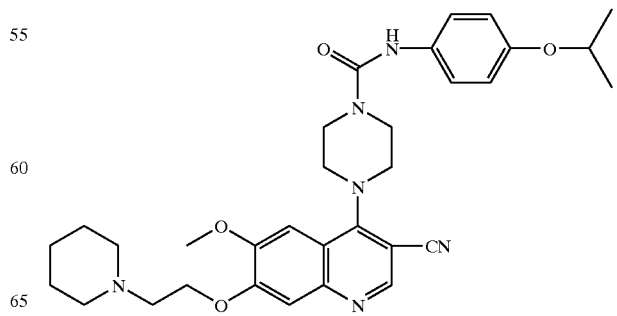

| 31 | 32 |
|---|---|
| N-(4-cyanophenyl){4-[3-cyano-6-methoxy-7-(2-piperidylethoxy)quinolin-4-yl]piperazinyl}carboxamide | N-(4-cyanophenyl){4-[3-cyano-6-methoxy-7-(3-morpholin-4-ylpropoxy)quinolin-4-yl]piperazinyl}carboxamide |

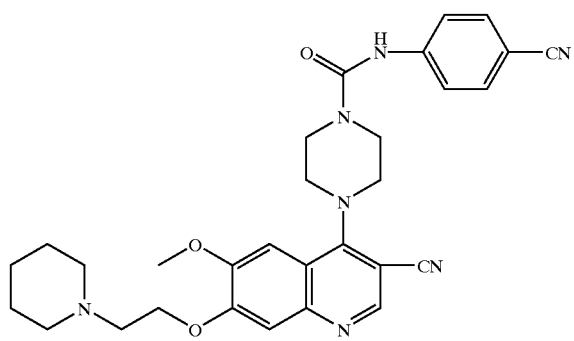

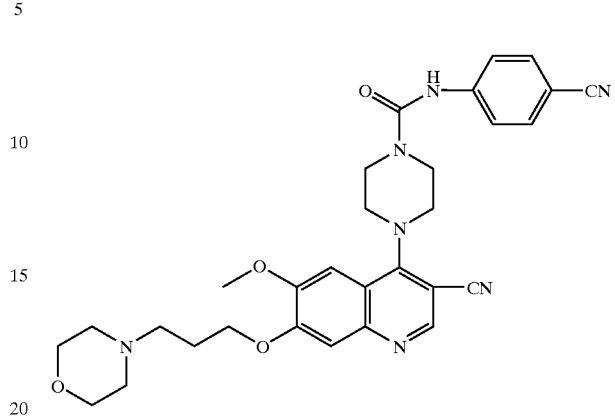

{4-[3-cyano-6-methoxy-7-(3-piperidylpropoxy)quinolin-4-yl]piperazinyl}-N-[4-(methylethoxy)phenyl]carboxamide {4-[3-cyano-6-methoxy-7-(3-pyrrolidinylpropoxy)quinolin-4-yl]piperazinyl}-N-[4-(methylethoxy)phenyl]carboxamide

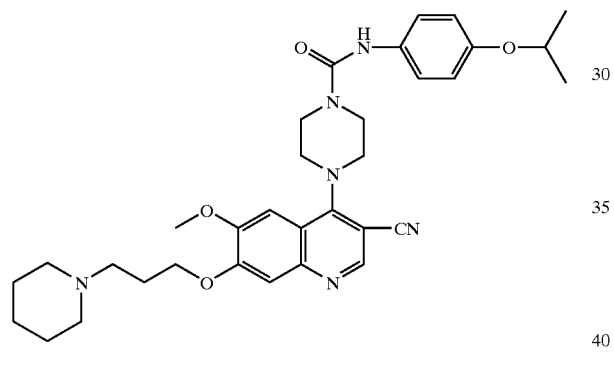

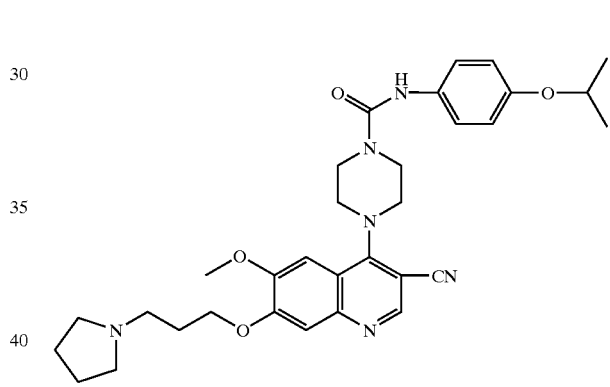

{4-[3-cyano-6-methoxy-7-(3-morpholin-4-ylpropoxy)quinolin-4-yl]piperazinyl}-N-[4-(methylethoxy)phenyl]carboxamide N-(4-cyanophenyl){4-[3-cyano-6-methoxy-7-(2-(1,2,3,4-tetraazol-2-yl)ethoxy)quinolin-4-yl]piperazinyl}carboxamide

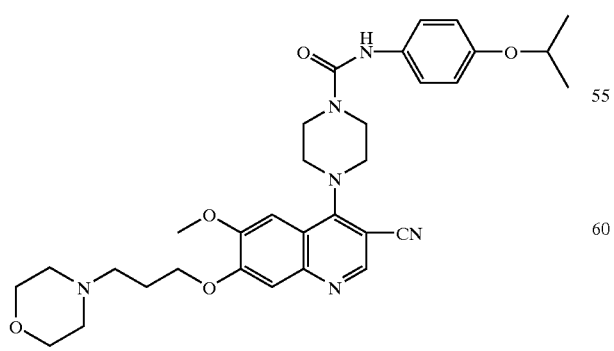

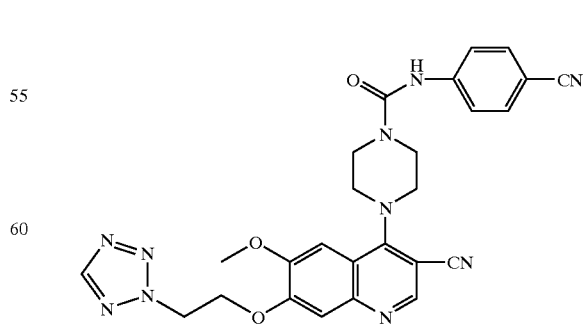

| 33 | 34 |
|---|---|
| N-(4-cyanophenyl){4-[3-cyano-6-methoxy-7-(2-(1,2,3,4-tetraazolyl)ethoxy)quinolin-4-yl]piperazinyl}carboxamide | {4-[3-cyano-6-methoxy-7-(2-(1,2,3,4-tetraazol-2-yl)ethoxy)quinolin-4-yl]piperazinyl}-N-[4-(methylethoxy)phenyl]carboxamide |

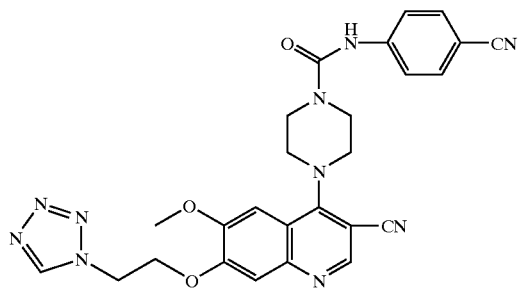

{4-[3-cyano-6-methoxy-7-(2-(1,2,3,4-tetraazolyl)ethoxy)quinolin-4-yl]piperazinyl}-N-[4-(methylethoxy)phenyl]carboxamide

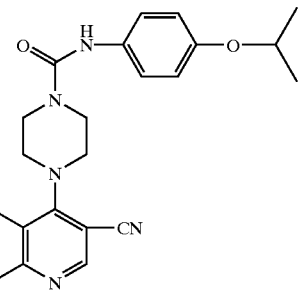

(4-{3-cyano-7-[3-(4,4-difluoropiperidyl)propoxy]-6-methoxyquinolin-4-yl}piperazinyl)-N-[4-(methylethoxy)phenyl]carboxamide

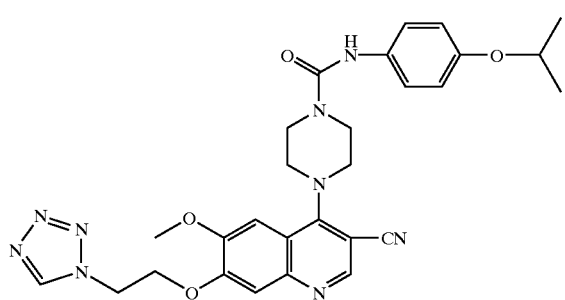

{4-[3-cyano-6-methoxy-7-(3-piperazinylpropoxy)quinolin-4-yl]piperazinyl}-N-[4-(methylethoxy)phenyl]carboxamide N-(4-cyanophenyl)(4-{3-cyano-6-methoxy-7-[3-(4-methylpiperazinyl)propoxy]quinolin-4-yl}piperazinyl)carboxamide

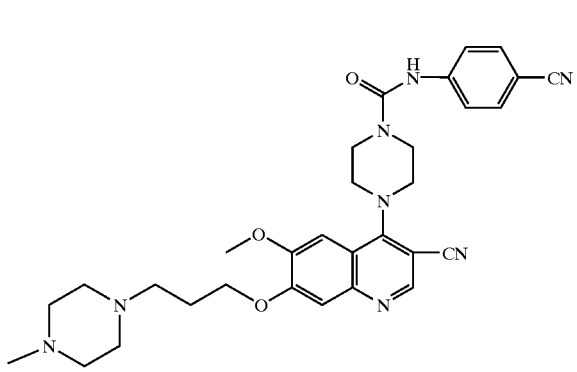

N-(4-cyanophenyl){4-[3-cyano-6-methoxy-7-(3-(1,4-thiazaperhydroin-4-yl)propoxy) quinolin-4-yl]piperazinyl}carboxamide

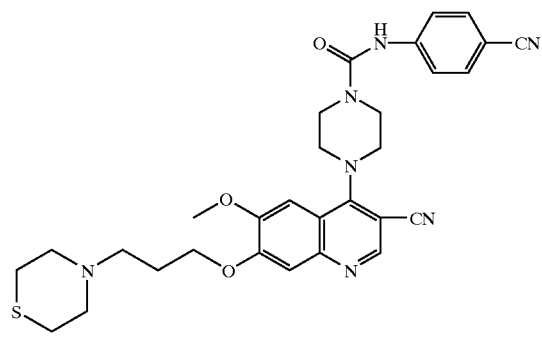

(4-{3-cyano-7-[3-(1,1-dioxo(1,4-thiazaperhydroin-4-yl))propoxy]-6-methoxy quinolin-4-yl}piperazinyl)—N-(4-cyanophenyl)carboxamide

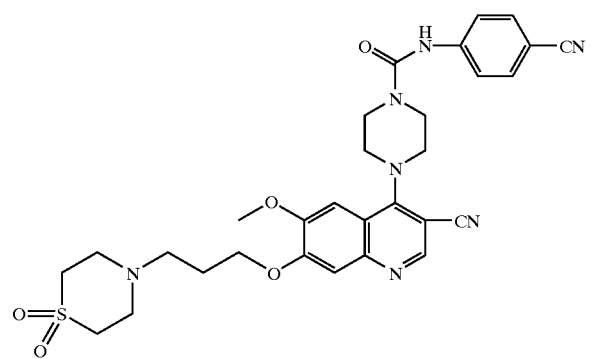

N-(4-cyanophenyl)[4-(3-cyano-7-ethoxy-6-methoxyquinolin-4-yl)piperazinyl]carboxamide

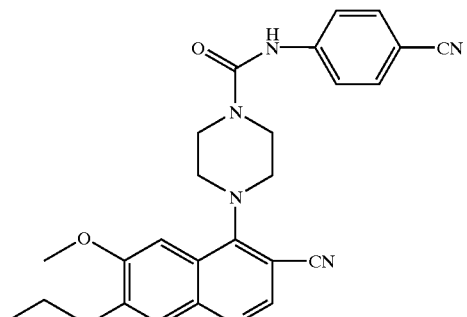

[4-(3-cyano-7-ethoxy-6-methoxyquinolin-4-yl)piperazinyl]-N-[4-(methylethoxy)phenyl]carboxamide

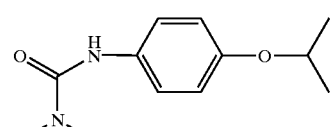
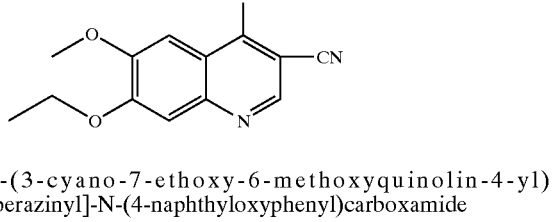

[4-(3-cyano-7-ethoxy-6-methoxyquinolin-4-yl)piperazinyl]-N-(4-naphthyloxyphenyl)carboxamide

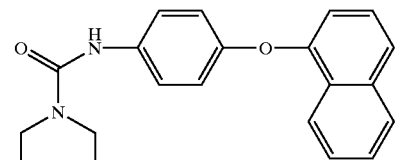
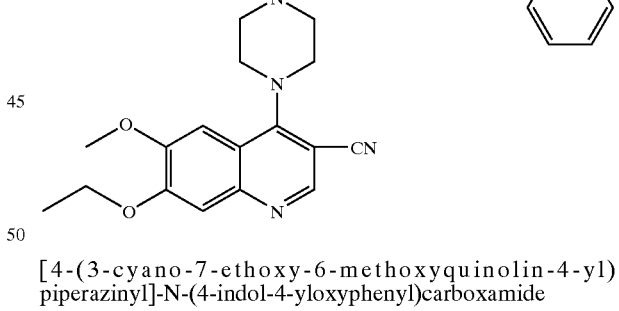

[4-(3-cyano-7-ethoxy-6-methoxyquinolin-4-yl)piperazinyl]-N-(4-indol-4-yloxyphenyl)carboxamide

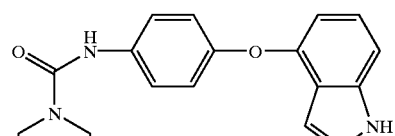

37

[4–3-cyano-(7-ethoxy-6-methoxyquinolin-4-yl)piperazinyl]-N-(4-phenoxyphenyl)carboxamide

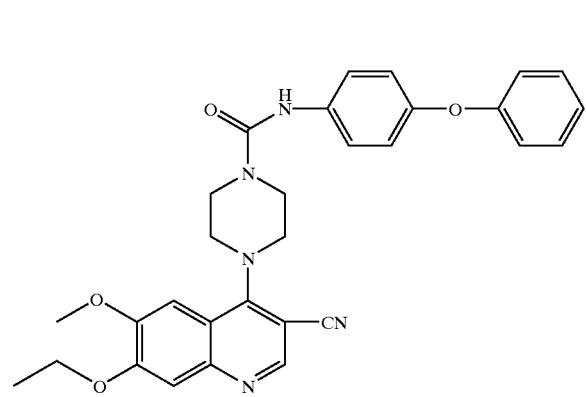

N-(4-cyanophenyl)[4-(3-cyano-6-methoxy-7-prop-2-enyloxyquinolin-4-yl)piperazinyl]carboxamide

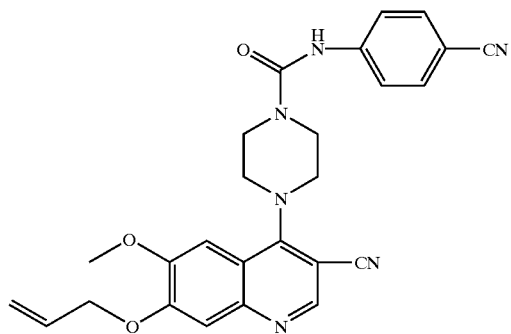

[4-(3-cyano-6-methoxy-7-prop-2-enyloxyquinolin-4-yl)piperazinyl]-N-[4-(methylethoxy)phenyl]carboxamide

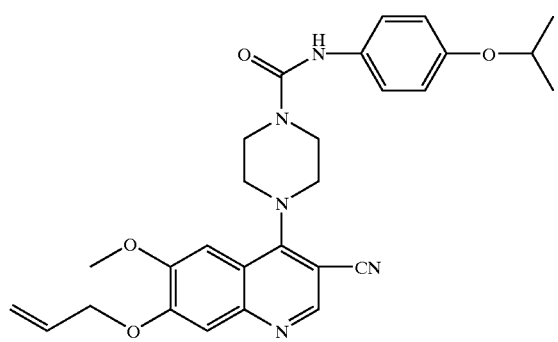

38

[4-(3-cyano-6-methoxy-7-prop-2-enyloxyquinolin-4-yl)piperazinyl]-N -(4-naphthyloxyphenyl)carboxamide

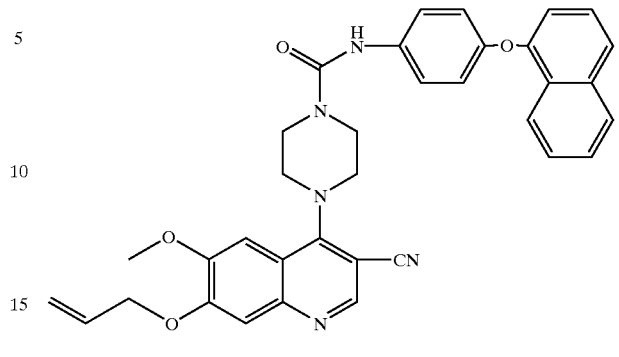

N-(4-indol-4-yloxyphenyl)[4-(3-cyano-6-methoxy-7-prop-2-enyloxyquinolin-4-yl)piperazinyl]carboxamide

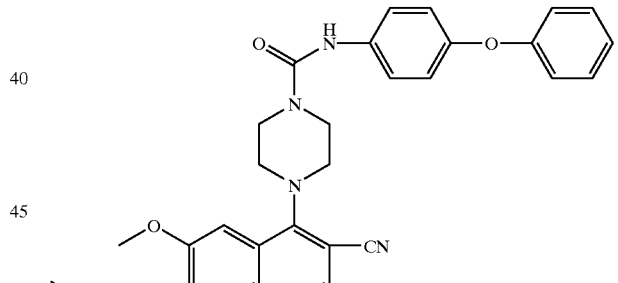

[4-(3-cyano-6-methoxy-7-prop-2-enyloxyquinolin-4-yl)piperazinyl]-N-(4-phenoxyphenyl)carboxamide N-(4-cyanophenyl)[4-(3-cyano-6-methoxy-7-prop-2-ynyloxyquinolin-4-yl)piperazinyl]carboxamide

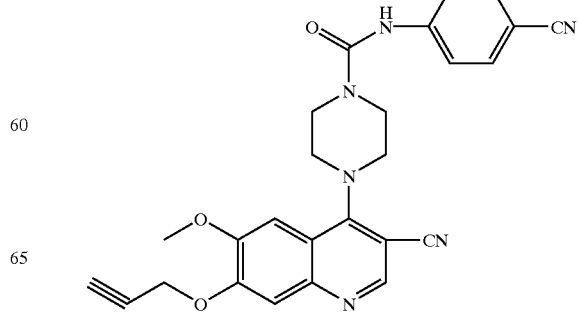

[4-(3-cyano-6-methoxy-7-prop-2-ynyloxyquinolin-4-yl)
piperazinyl]-N-[4-(methylethoxy)phenyl]carboxamide

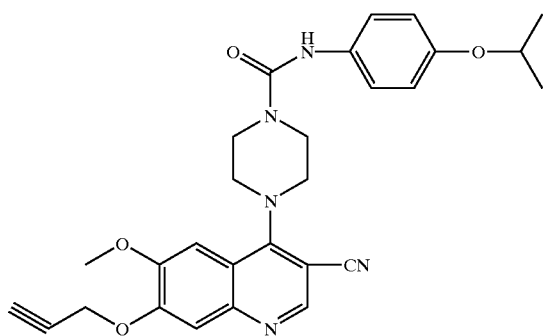

[4-(3-cyano-6-methoxy-7-prop-2-ynyloxyquinolin-4-yl)
piperazinyl]-N-(4-naphthyloxyphenyl)carboxamide

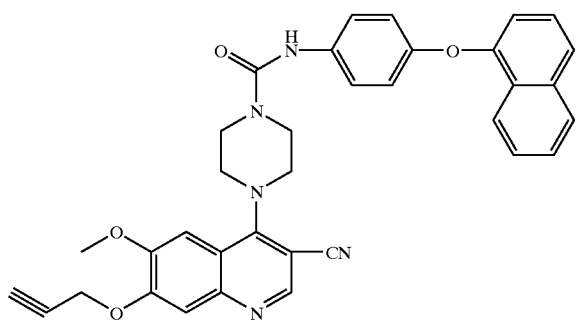

N-(4idol-4yloxyphenyl)[4-(3-cyano-6-methoxy-7-prop-2-
ynyloxyquinolin-4-yl)piperazinyl]carboxamide

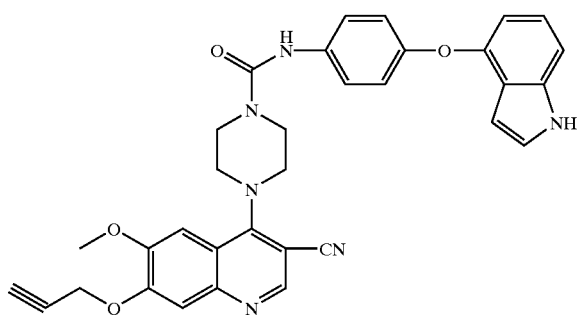

[4-(3-cyano-6-methoxy-7-prop-2-ynyloxyquinolin-4-yl)
piperazinyl]-N-(4-phenoxyphenyl)carboxamide

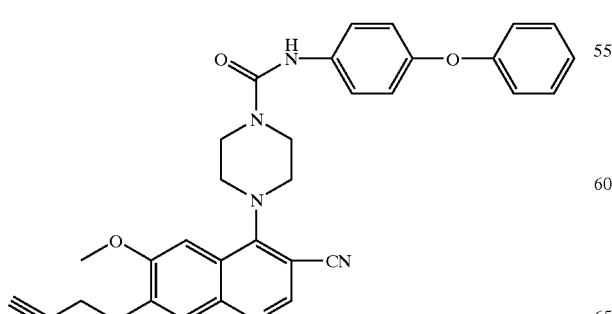

ethyl-6-methoxy-4-(4-{N-[4-(methylethoxy)phenyl]
carbamoyl}piperazinyl)-7-(3-piperidylpropoxy)quinoline-
3-carboxylate

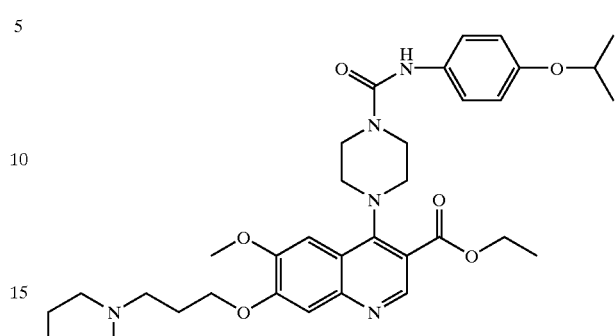

ethyl6-methoxy-4-(4-{N-[4-(methylethoxy)phenyl]
carbamoyl}piperazinyl)-7-(3-morpholin-4-ylpropoxy)
quinoline -3-carboxylate

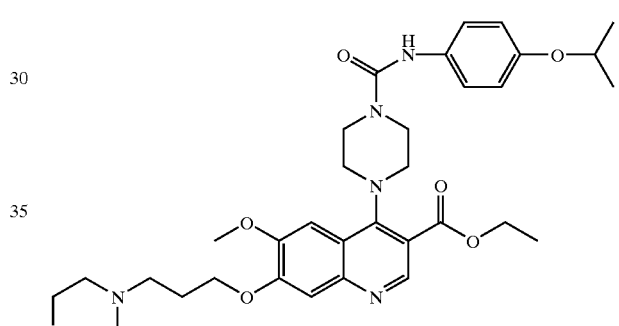

ethyl6-methoxy-4-(4-{N-[4-(methylethoxy)phenyl]
carbamoyl}piperazinyl)-7-(3-(1,2,3-triazolyl)propoxy)
quinoline-3-carboxylate

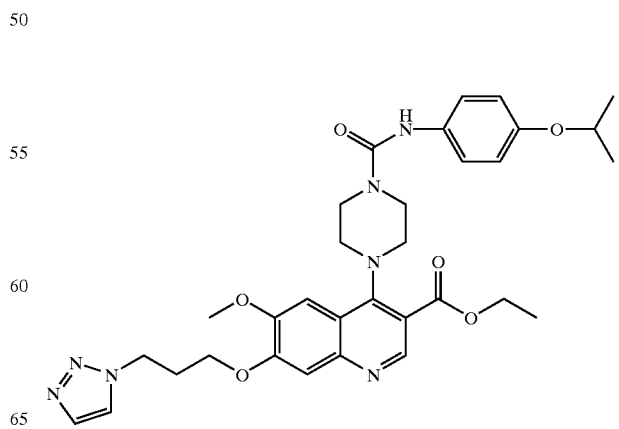

41

6-methoxy-4-(4-(N-[4-(methylethoxy)phenyl]carbamoyl)piperazinyl)-7-(3-(1,2,3-triazol-2-yl)propoxy)quinoline-3-carboxylic Acid

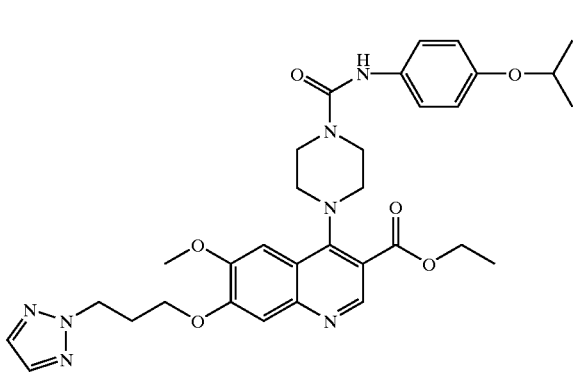

ethyl 4-{4-[N-(4-cyanophenyl)carbamoyl]piperazinyl}-6-methoxy-7-(3-piperidylpropoxy)quinoline-3-carboxylate

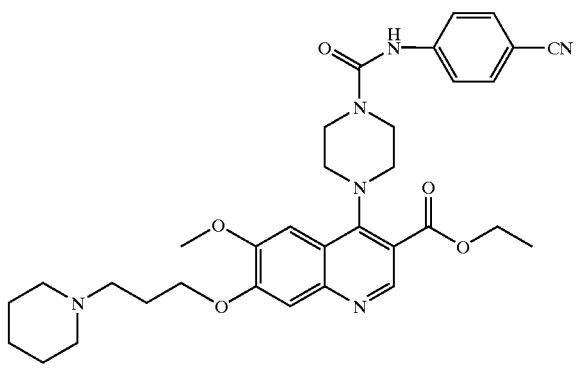

ethyl 4-{4-[N-(4-cyanophenyl)carbamoyl]piperazinyl}-6-methoxy-7-(3-morpholin-4-ylpropoxy)quinoline-3-carboxylate

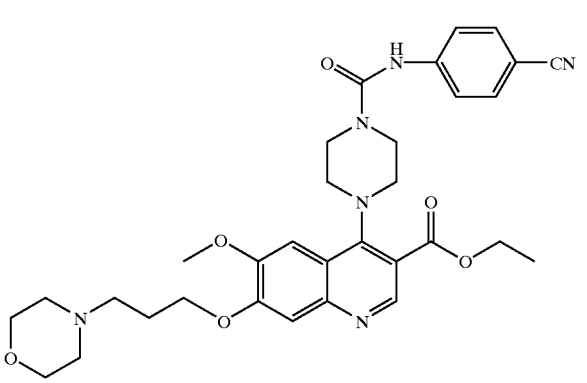

42 ethyl 4-{4-[N-(4-cyanophenyl)carbamoyl]piperazinyl)-6-methoxy-7-(3-pyrrolidinylpropoxy)quinoline-3-carboxylate

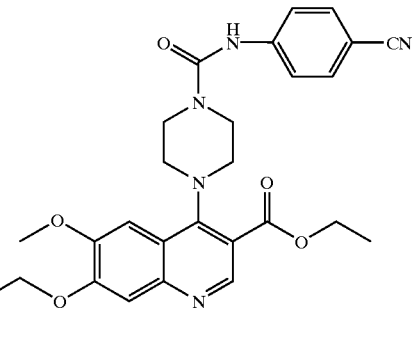

ethyl 4-{4-[N-(4-cyanophenyl)carbamoyl]piperazinyl)-6-methoxy-7-(3-(1,2,3-triazolyl)propoxy)quinoline-3-carboxylate

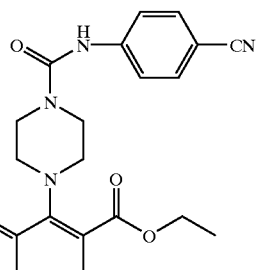

ethyl 4-{4-[N-(4-cyanophenyl)carbamoyl]piperazinyl}-6-methoxy-7-(3-(1,2,3-triazol-2-yl)propoxy)quinoline-3-carboxylate

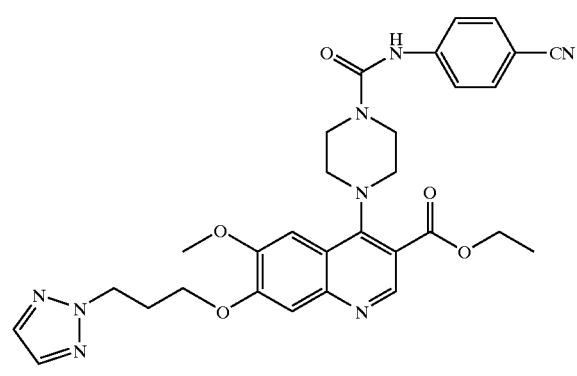

ethyl 4-{4-[N-(4-cyanophenyl)carbamoyl]piperazinyl}-6-methoxy-7-(3-(1,2,3,4-tetraazol-2-yl)propoxy)quinoline-3-carboxylate

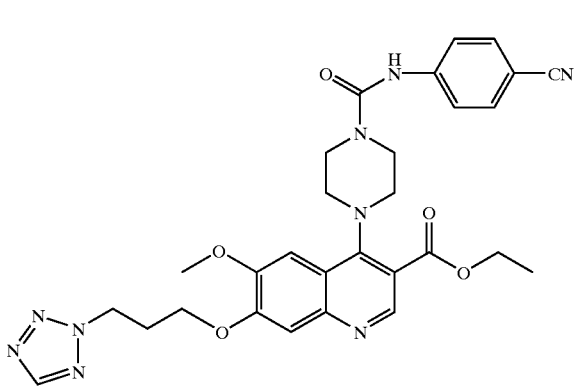

ethyl 4-{4-[N-(4-cyanophenyl)carbamoyl]piperazinyl}-6-methoxy-7-(3-(1,2,3,4-tetraazolyl)propoxy)quinoline-3-carboxylate

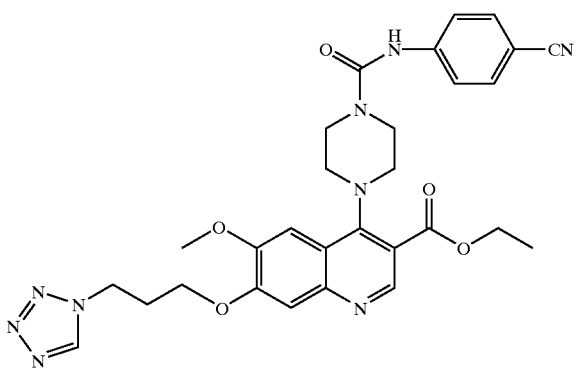

ethyl 7-[3-(1,1-dioxo(1,4-thiazaperhydroin-4-yl))propoxy]-4-{4-[N-(4-cyanophenyl)carbamoyl]piperazinyl}-6-methoxyquinoline-3-carboxylate

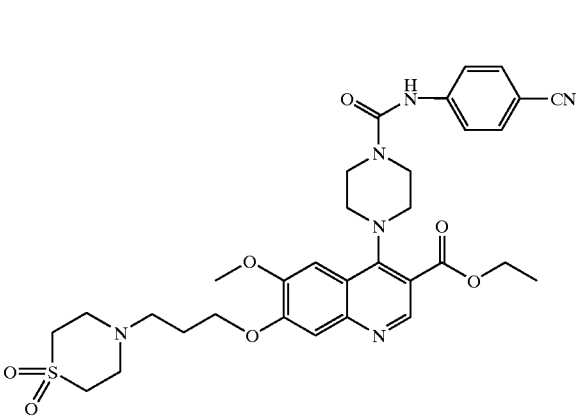

ethyl 4-{4-[N-(4-cyanophenyl)carbamoyl]piperazinyl}-6-methoxy-7-(3-piperazinylpropoxy)quinoline-3-carboxylate

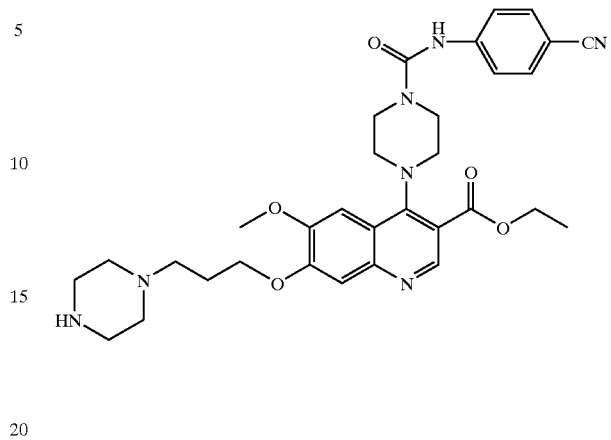

ethyl 4-{4-[N-(4-cyanophenyl)carbamoyl]piperazinyl}-6-methoxy-7-(2-methoxyethoxy)quinoline-3-carboxylate

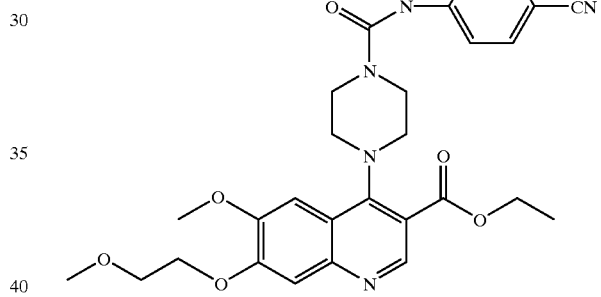

ethyl 6-methoxy-7-(2-methoxyethoxy)-4-4-{N-[4-(methylethoxy)phenyl]-carbamoyl}piperazinyl)quinoline-3-carboxylate

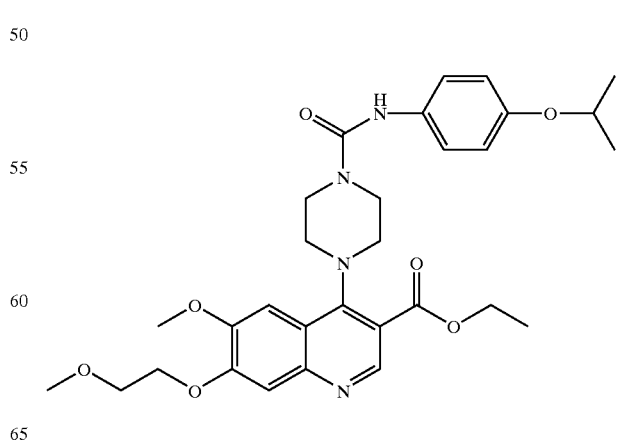

ethyl 4-{4-[N-(4-cyanophenyl)carbamoyl]piperazinyl}-6-methoxy-7-[3-(4-methylpiperazinylpropoxy]quinoline-3-carboxylate (4-{7-[3-(1,1-dioxo(1,4-thiazaperhydroin-4-yl))propoxy]-3-carbonyl-6-methoxy(4-quinolyl)}piperazinyl)—N-[4-(methylethoxy)phenyl]carboxamide

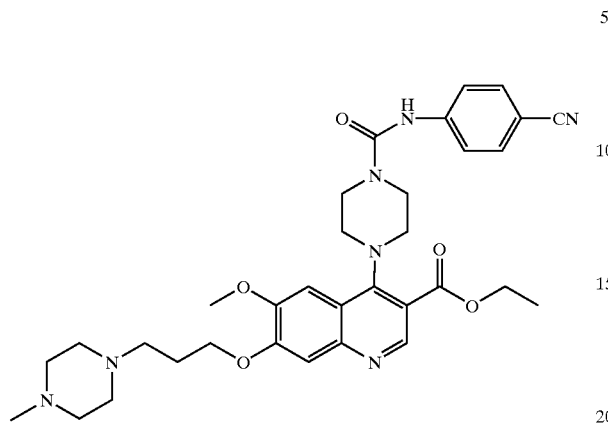

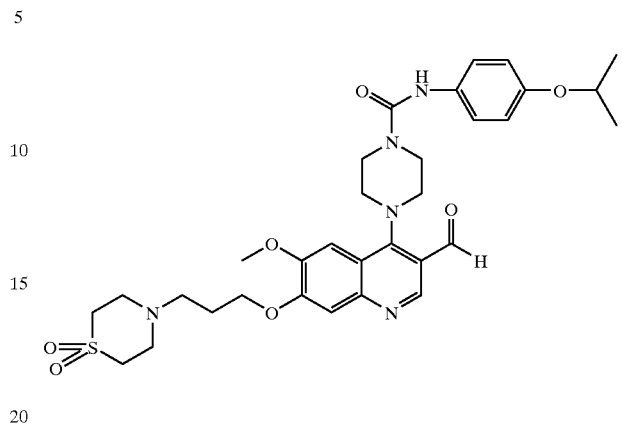

{4-[3-carbonyl-6-methoxy-7-(3-piperidylpropoxy)(4-quinolyl)]piperazinyl}-N-[4-(methylethoxy)phenyl]carboxamide {4-[3-carbonyl-6-methoxy-7-(3-pyrrolidinylpropoxy)(4-quinolyl)]piperazinyl}-N-[4-(methylethoxy)phenyl]carboxamide

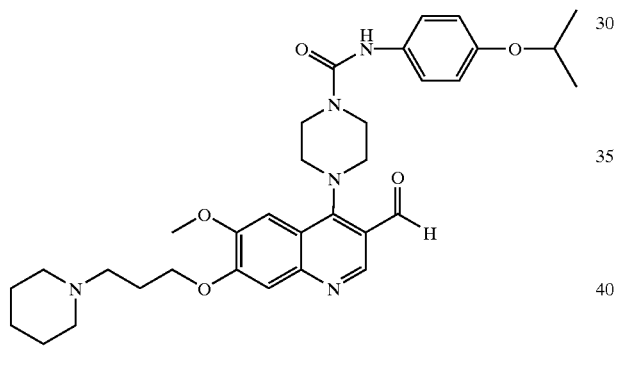

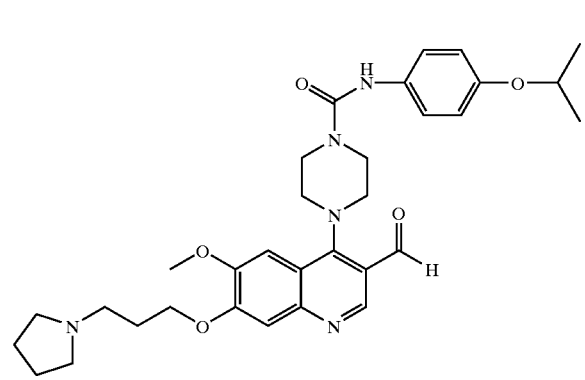

{4-[3-carbonyl-6-methoxy-7-(3-morpholin-4-ylpropoxy)(4-quinolyl)]piperazinyl}-N-[4-(methylethoxy)phenyl]carboxamide {4-[3-carbonyl-6-methoxy-7-(3-piperidylpropoxy)(4-quinolyl)]piperazinyl}-N-(4-cyanophenyl)carboxamide

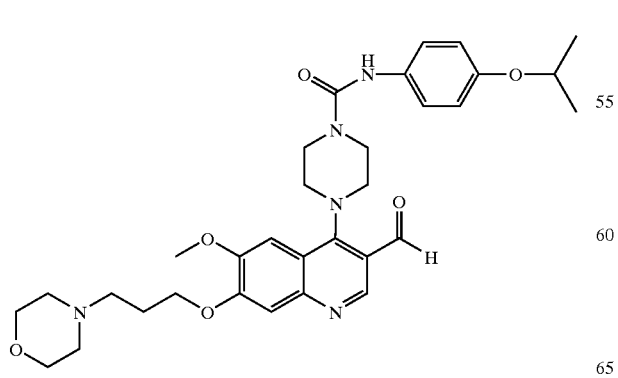

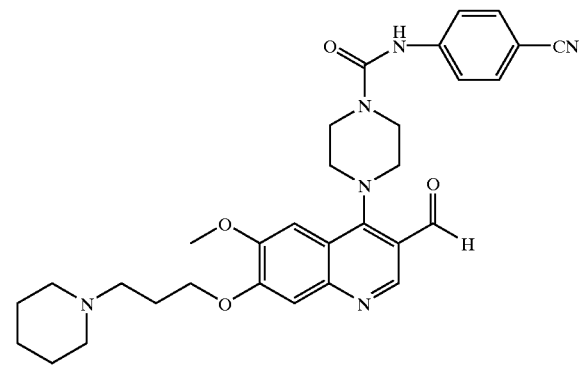

| 47 | 48 |
|---|---|
| {4-[3-carbonyl-6-methoxy-7-(3-morpholin-4-ylpropoxy)(4-quinolyl)]piperazinyl}-N-(4-cyanophenyl)carboxamide | {4-[3-carbonyl-6-methoxy-7-(3-(1,2,3-triazol-2-yl)propoxy)(4-quinolyl)]piperazinyl}-N-(4-cyanophenyl)carboxamide |

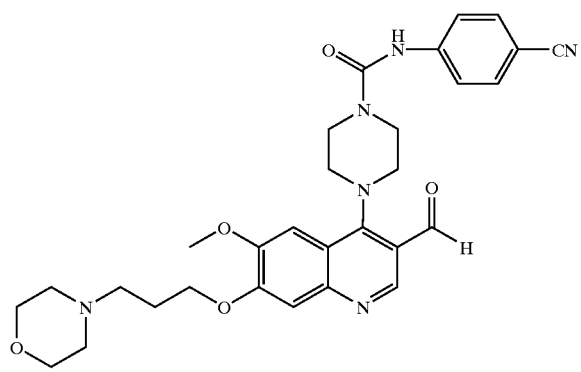 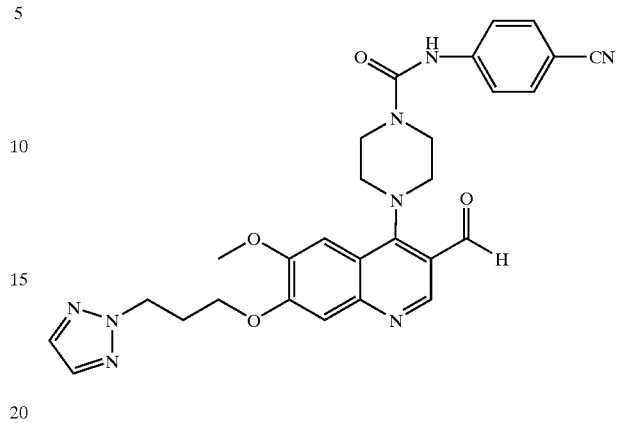

{4-[3-carbonyl-6-methoxy-7-(3-myrpolinylpropoxy)(4-quinoyl)]piperazinyl}-N-(4-cyanophenyl)carboxamide N-(4-cyanophenyl){4-[3-(hydroxymethyl)-6-methoxy-7-(3-piperidylpropoxy)(4-quinolyl)]piperazinyl}carboxamide

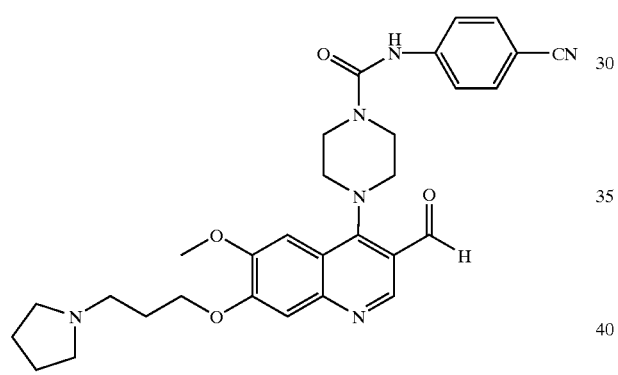 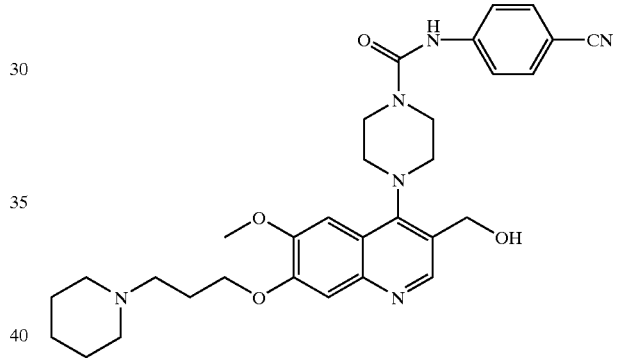

{4-[3-carbonyl-6-methoxy-7-(3-(1,2,3-trinazolyl)propoxy)(4-quinolyl)]piperazinyl}-N-(4-cyanophenyl)carboxamide N-(4-cyanophenyl){4-[3-(hydroxymethyl)-6-methoxy-7-(3-morpholin-4-ylpropoxy) (4-quinolyl)]piperazinyl}carboxamide

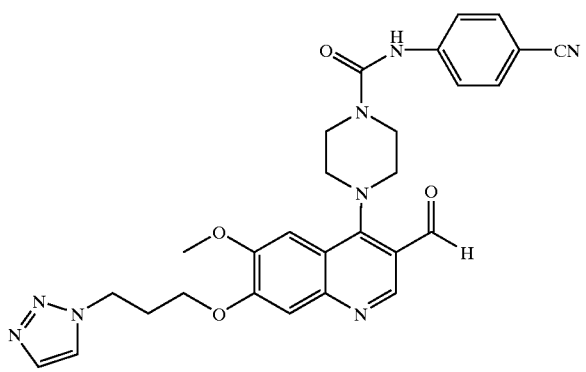 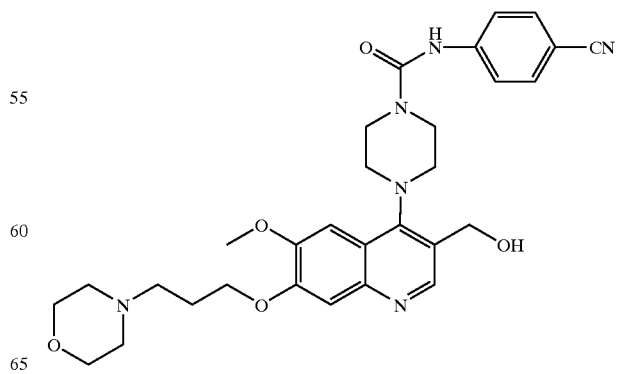

| 49 | 50 |
|---|---|
| N-(4-cyanophenyl){4-[3-(hydroxymethyl)-6-methoxy-7-(3-pyrrolidinylpropoxy)(4-quinolyl)]piperazinyl}carboxamide | (4-{7-[3-(1,1-dioxo(1,4-thiazaperhydroin-4-yl))propoxy]-3-(hydroxymethyl)-6-methoxy(4-quinolyl)}piperazinyl)-N-[4-(methylethoxy)phenyl]carboxamide |

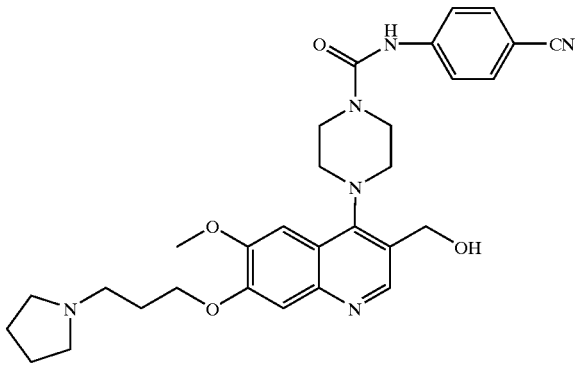

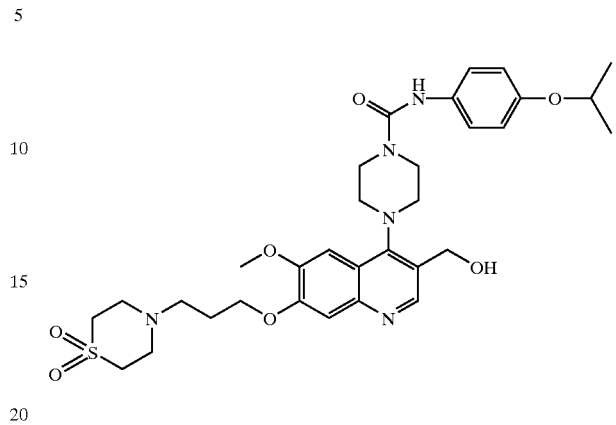

{4-[3-(hydroxymethyl)-6-methoxy-7-(3-piperidylpropoxy)(4-quinolyl)]piperazinyl}-N-[4-(methylethoxy)phenyl]carboxamide {4-[3-(hydroxymethyl)-6-methoxy-7-(3-pyrrolidinylpropoxy)(4-quinolyl)]piperazinyl}-N-[4-(methylethoxy)phenyl]carboxamide

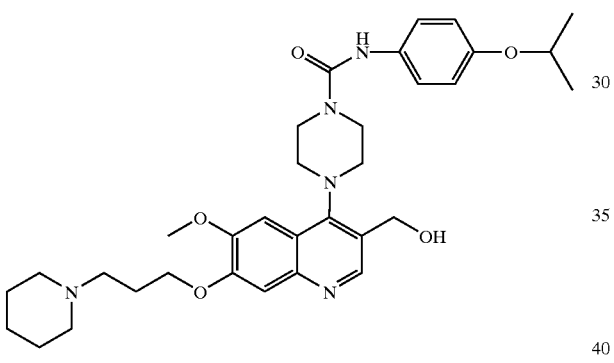

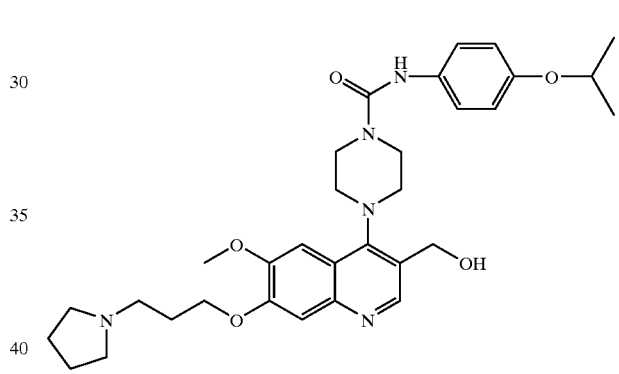

{4-[3-(hydroxymethyl)-6-methoxy-7-(3-morpholin-4-ylpropoxy)(4-quinolyl)]piperazinyl}-N-[4-(methylethoxy)phenyl]carboxamide 4-[3-Aminomethyl-6-methoxy-7-(3-piperidin-1-yl-propoxy)-quinolin-4-yl]-piperazine-1-carboxylic Acid (4-cyano-phenyl)-amide

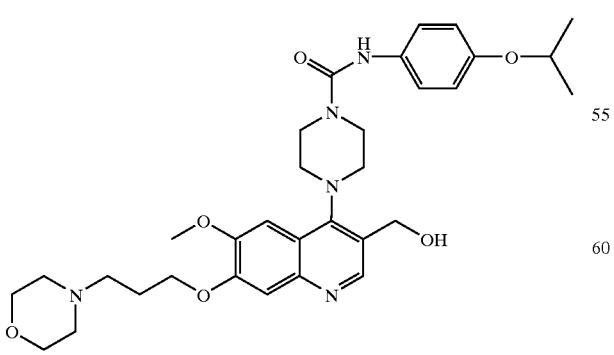

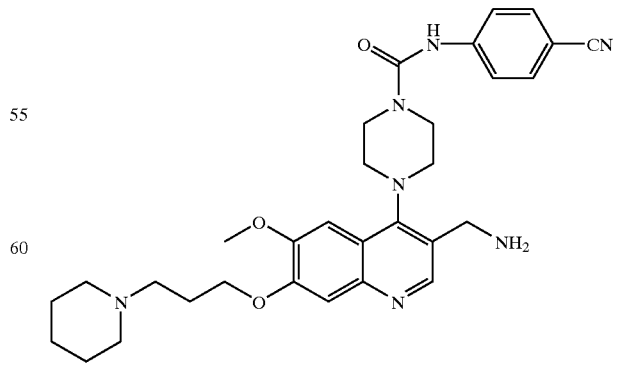

51

4-[3-Aminomethyl-6-methoxy-7-(3-piperidin-1-yl-propoxy)-quinolin-4-yl]-piperazine-1-carboxylic Acid(4-isopropoxy-phenyl)-amide

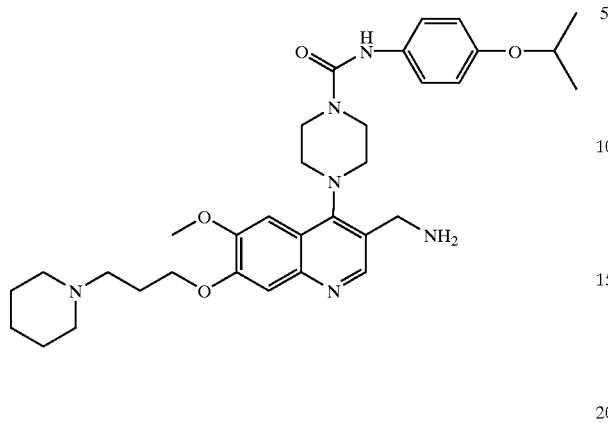

4-[3-Aminomethyl-6-methoxy-7-(3-morpholin-4-yl-propoxy)-quinolin-4-yl]-piperazine-1-carboxylic Acid(4-cyano-phenyl)-amide

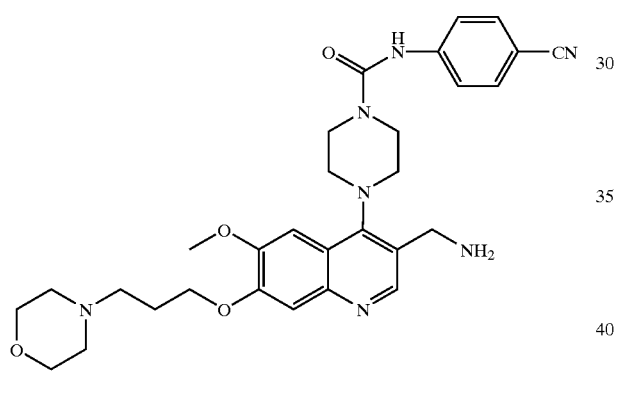

4-[3-Aminomethyl-6-methoxy-7-(3-morpholin-4-yl-propoxy)-quinolin-4-yl]-piperazine-1-carboxylic Acid (4-isopropoxy-phenyl)-amide

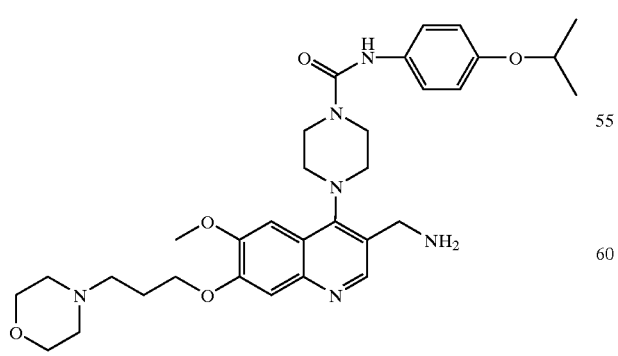

52

4-[3-Cyano-6-methoxy-7-(3-pyrrolidin-1-yl-propoxy)-quinolin-4-yl]-piperazine-1-carboxylic Acid (4-cyano-phenyl)-amide

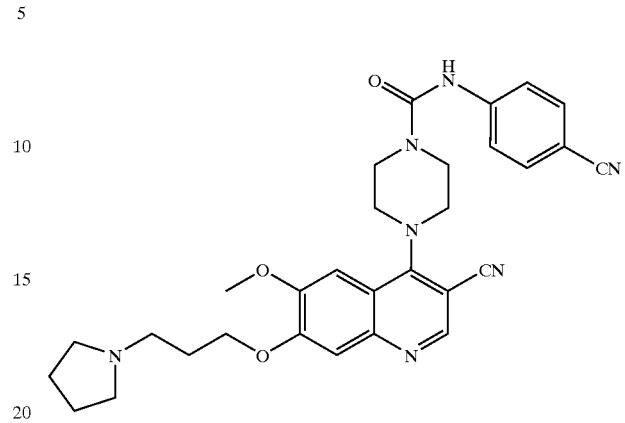

4-[3-Cyano-6-methoxy-7-(3-pyrrolidin-1-yl -propoxy)-quinolin-4-yl]-piperazine-1-carboxylic Acid (4-bromo-phenyl)-amide

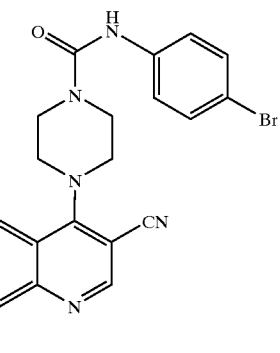

4-[3-Cyano-6-methoxy-7-(3-pyrrolidin-1-yl-propoxy)-quinolin-4-yl]-piperazine-1-carboxylic Acid (4-isopropoxy-phenyl)-amide

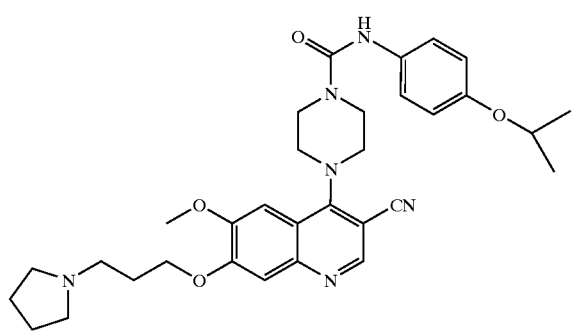

53

4-({4-[3-Cyano-6-methoxy-7-(3-pyrrolidin-1-yl-propoxy)-quinolin-4-yl]-piperazine-1-carbonyl})-amino)-benzoic Acid Methyl Ester

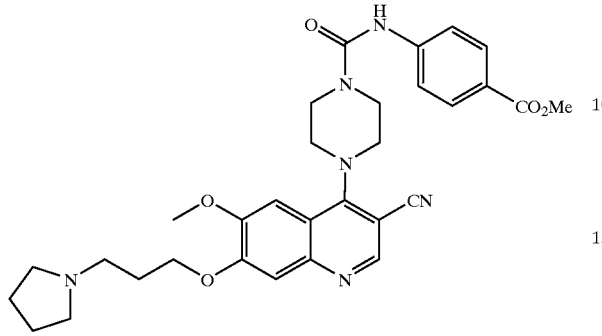

4-((4-[3-Cyano-6-methoxy-7-(3-piperidin-1-yl-propoxy)-quinolin-4-yl]-piperazine-1-carbonyl)-amino)-benzoic Acid Methyl Ester

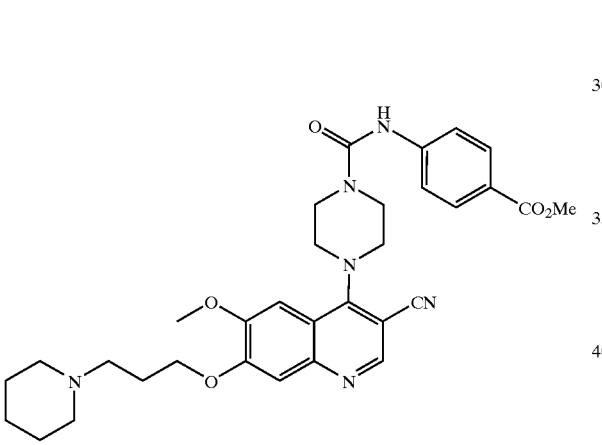

4-[3-Cyano-6-methoxy-7-(3-piperidin-1-yl-propoxy)-quinolin-4-yl]-piperazine-1-carboxylic Acid (4-bromo-phenyl)-amide

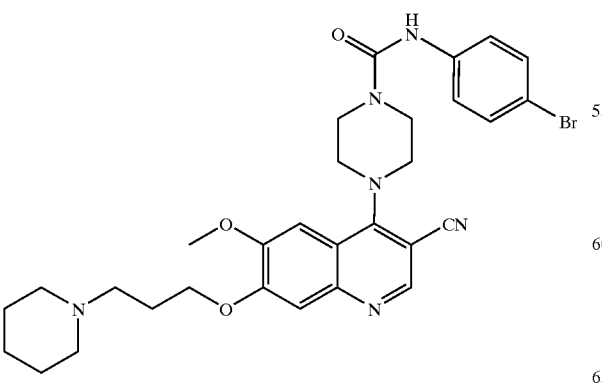

54

4-[3-Cyano-6-methoxy-7-(3-piperidin-1-yl-propoxy)-quilolin-4-yl]-piperazine-1-carboxylic Acid (4-trifluoromethyl-phenyl)-amide

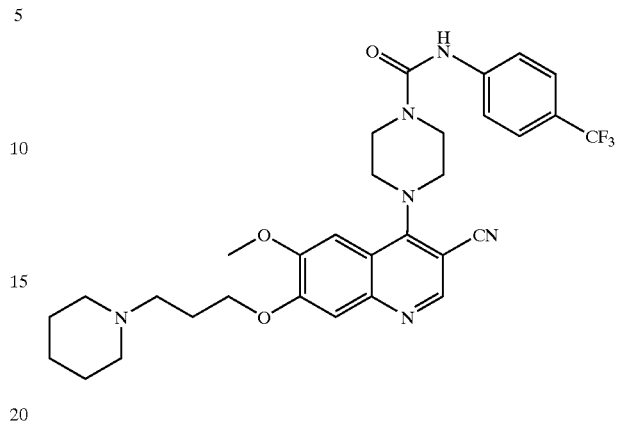

4-[3-Cyano-6-methoxy-7-(3-piperidin-1-yl-propoxy)-quinolin-4-yl]-piperazine-1-carboxylic Acid (4-fluoro-phenyl)-amide

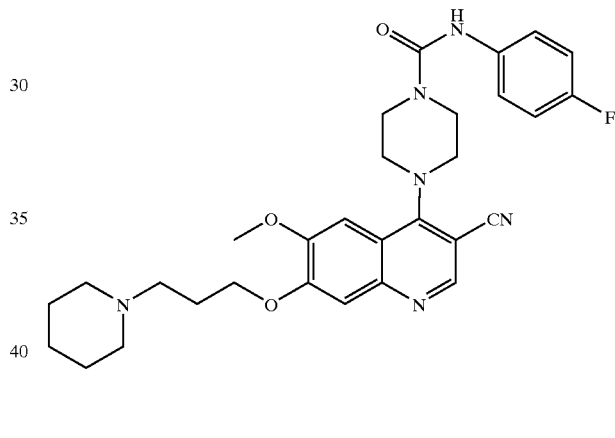

4-[3-Fluoro-6-methoxy-7-(3-piperidin-1-yl-propoxy)-quinolin-4-yl]-piperazine-1-carboxylic Acid (4-cyano-phenyl)-amide

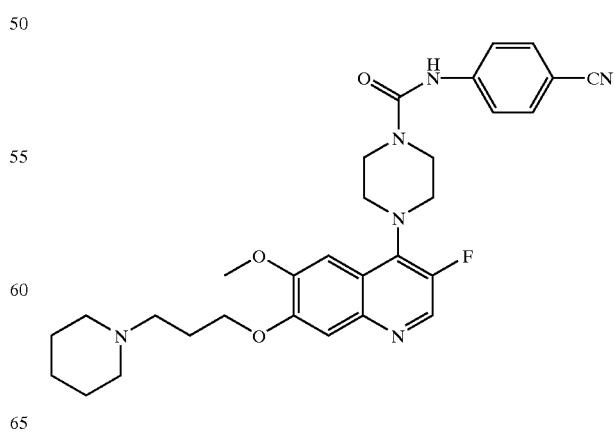

4-[3-Fluoro-6-methoxy-7-(3-piperidin-1-yl-propoxy)-quinolin-4-yl]-piperazine-1-carboxylic Acid (4-isopropoxy-phenyl)-amide 4-[3-Fluoro-6-methoxy-7-(3-pyrrolidin-1-yl-propoxy)-quinolin-4-yl]-piperazine-1-carboxylic Acid (4-cyano-phenyl)-amide

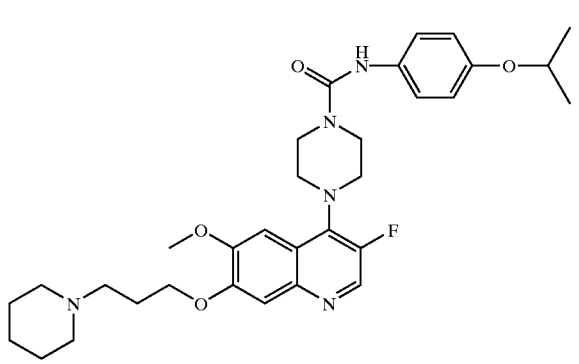
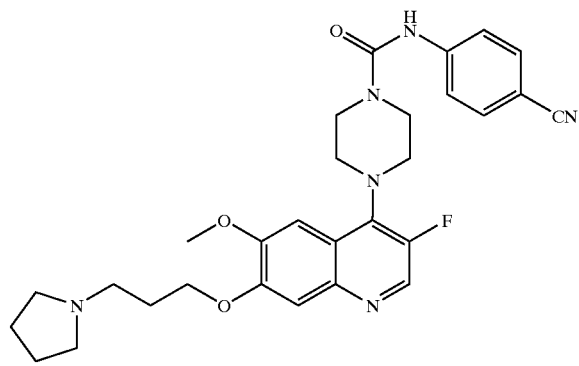

4-[3-Fluoro-6-methoxy-7-(3-morpholin-4-yl-propoxy)-quinolin-4-yl]-piperazine-1-carboxylic Acid (4-cyano-phenyl)-amide 4-[3-Fluoro-6-methoxy-7-(3-pyrrolidin-1-yl-propoxy)-quinolin-4-yl]-piperazine-1-carboxylic Acid (4-bromo-phenyl)-amide

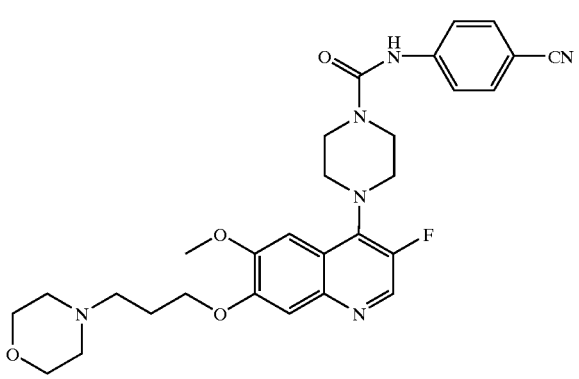

4-[3-Fluoro-6-methoxy-7-(3-morpholin-4-yl-propoxy)-quinolin-4-yl]-piperazine-1-carboxylic acid (4-isopropoxy-phenyl)-amide 4-[3-Fluoro-6-methoxy-7-(3-pyrrolidin-1-yl-propoxy)-quinolin-4-yl]-piperazine-1-carboxylic Acid (4-isopropoxy-phenyl)-amide

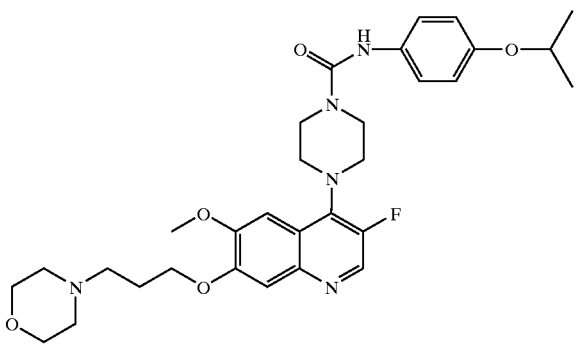
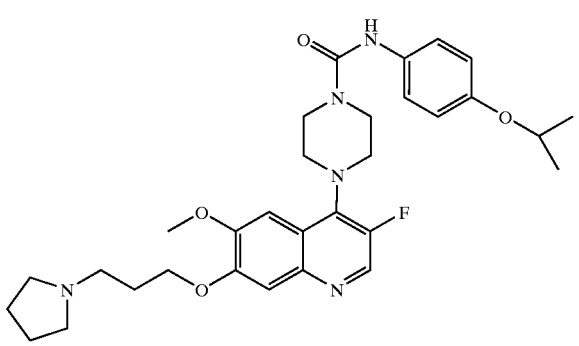

4-({4-[3-Fluoro-6-methoxy-7-(3-pyrrolidin-1-yl-propoxy)-quinolin-4-yl]-piperazine-1-carbonyl}-amino)-benzoic Acid Methyl Ester

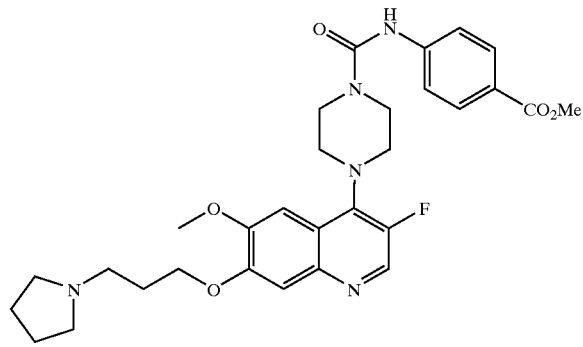

and all pharmaceutically acceptable isomers, salts, hydrates, solvates and prodrug derivatives thereof.

Preparation of Compounds

The compounds may be prepared using methods and procedures as generally described in WO 98/14431 published Sep. 12, 1998, which is incorporated herein by reference. Intermediates can also be made using methods and procedures described in U.S. Pat. No. 6,002,008; Bioorg. & Med. Chem. Lett., 10: 2825–2828 (2000); WO 0068201; Bioorg. & Med. Chem. Lett., 10: 2477–2485, and in J. Med. Chem. ,43: 3244–3256 (2000). Starting materials may be made or obtained as described therein as well. Leaving groups such as halogen, lower alkoxy, lower alkylthio, lower alkylsulfonyloxy, arylsulfonyloxy, etc, may be utilized when necessary except for the reaction point, followed by deprotection. Suitable amino protective groups are, for example, those described in T. W. Greene, Protective Groups in Organic Synthesis, John Wiley & Sons Inc. (1981), etc., such as ethoxycarbonyl, t-butoxycarbonyl, acetyl and benzyl. The protective groups can be introduced and eliminated according to conventional methods used in organic synthetic chemistry, e.g., T. W. Greene, Protective Groups in Organic Synthesis, John Wiley & Sons Inc. (1981).

In such processes, if the defined groups change under the conditions of the working method or are not appropriate for carrying out the method, the desired compound can be obtained by using the methods for introducing and eliminating protective groups which are conventionally used in organic synthetic chemistry, e.g., T. W. Greene, Protective Groups in Organic Synthesis, John Wiley & Sons Inc. (1981), etc. Conversion of functional groups contained in the substituents can be carried out by known methods, e.g., R. C. Larock, Comprehensive Organic Transformations (1989) in addition to the above-described processes, and some of the active compounds of formula I may be utilized as intermediates for further synthesizing novel derivatives according to formula I.

The intermediates and the desired compounds in the processes described above can be isolated and purified by purification methods conventionally used in organic synthetic chemistry, for example, neutralization, filtration, extraction, washing, drying, concentration, recrystallization, and various kinds of chromatography. The intermediates may be subjected to the subsequent reaction without purification.

There may be tautomers for some formulae set forth as embodiments of the invention, and the present invention covers all possible isomers including tautomers and mixtures thereof. Where chiral carbons lend themselves to two different enantiomers, both enantiomers are contemplated as well as procedures for separating the two enantiomers.

In the case where a salt of a compound of the above formulae is desired and the compound is produced in the form of the desired salt, it can be subjected to purification as such. In the case where a compound of formula I is produced in the free state and its salt is desired, the compound of formula I is dissolved or suspended in a suitable organic solvent, followed by addition of an acid or a base to form a salt.

The following non-limiting reaction Schemes I and II illustrate preferred embodiments of the invention with respect to making compounds according to the invention.

Scheme I

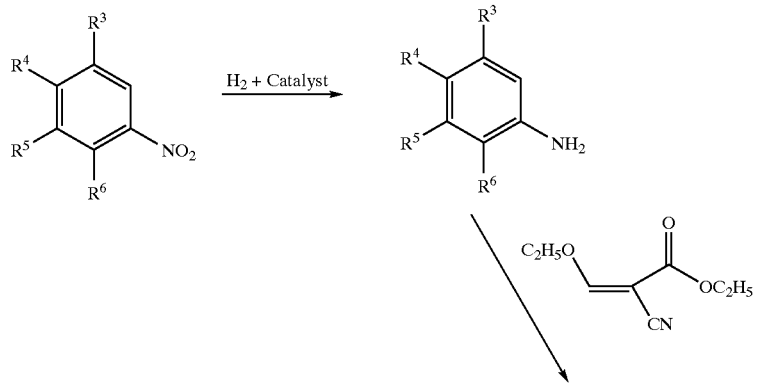

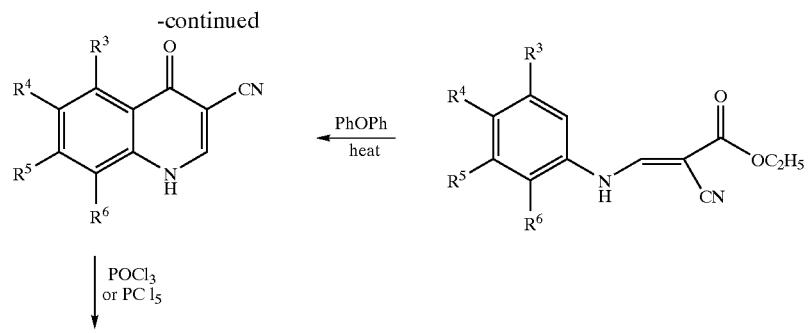

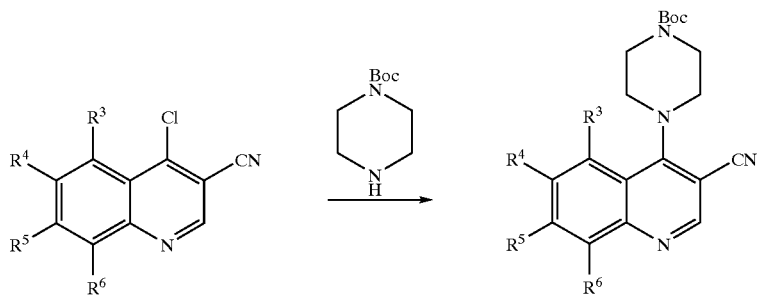

This synthesis of a tert-butyl-4-[3-cyano-6-methoxy-7-(phenylmethoxy)quinolin-4-yl]-piperazine carboxylate compound, provides an intermediate that can be utilized in the synthesis of various compounds (the scheme can be adapted to produce bicyclic position isomers) as described above for formula I. The nitro functionality is reduced with a reducing agent such as tin chloride, hydrogen in the presence of palladium on carbon, hydrogen in the presence of raney nickel, and the like, followed by addition of the alkylenenitrile derivative and cyclization to afford quinolinone. The synthesis of 3-cyano-4-Cl-quinoline is effected by treating 3-cyano-quinolinone with halogenating reagents such as thionyl chloride, oxalyl chloride and phosphorous oxychloride, or phosphorous pentachloride in presence of solvent such as toluene, or carbon tetrachloride. This intermediate is obtained by treating 3-cyano-4-chloro-quinoline with Boc-piperazine in an appropriate solvent, such as isopropanol, acetonitrile, or THF at room or reflux temperature for 1–6 h in presence of base triethylamine or pyridine.

Scheme II

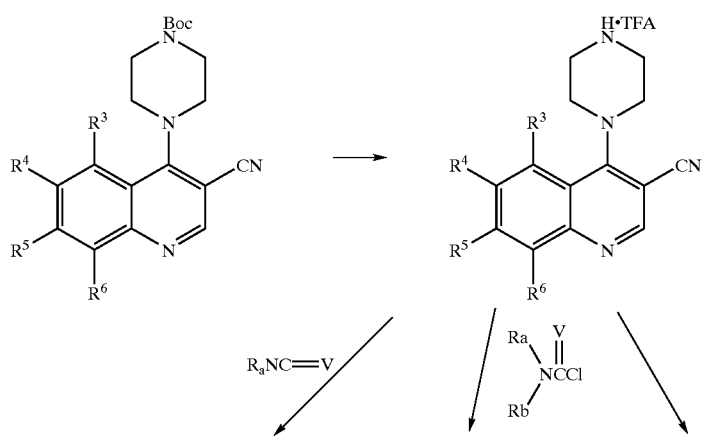

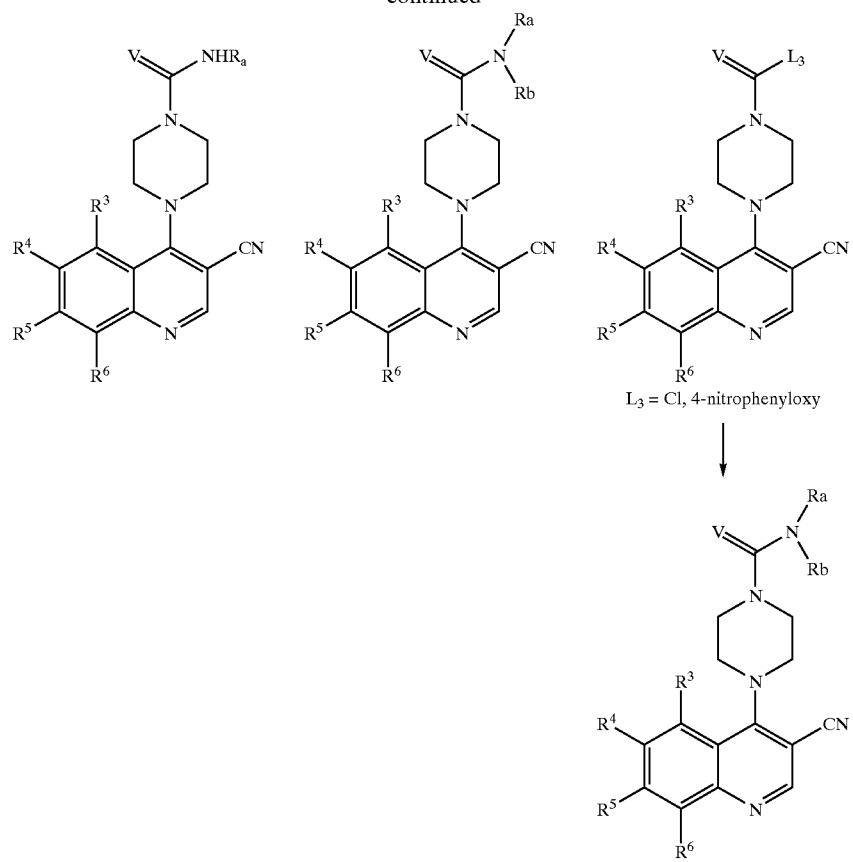

This illustrated Scheme II provides the synthesis of various urea or thio urea intermediates from the intermediate obtained in Scheme I, or by other procedures. The intermediate form Scheme I (or its bicyclic position isomer) is debenzylated under hydrogenation conditions followed by alkylation with various alkyl halides. Deprotection of Boc group is effected by trifluoroacetic acid followed by treatment with various isocyanates or thioisocyanates to afford the final urea or thiourea compounds. In cases where the isocyanates are not commercially available, the piperazine intermediate may be treated with phosgene to give a carbamoyl chloride intermediate followed by reaction with various anilines. The piperazine intermediate can also be treated with p-nitrophenyl chloroformate to afford a nitrophenyl carbamate intermediate that can be treated with various anilines to afford the desired ureas. If the urea compound has a terminal $NH_2$ group (or one or more of the hydrogen atoms on this amino group is substituted by a displaceable substituent), then this compound may be utilized an intermediate compound with which to produce a urea compound terminated with a —NH-phenyl-Y groups. Alternatively, if a different Y group is desired on the phenyl group, a replaceable para position leaving group phenyl substituent may be displaced after coupling to provide the particular Y substituent as described for formula Ia, above.

Scheme III

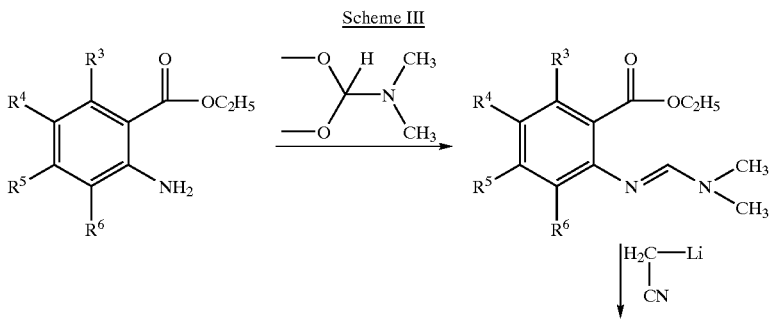

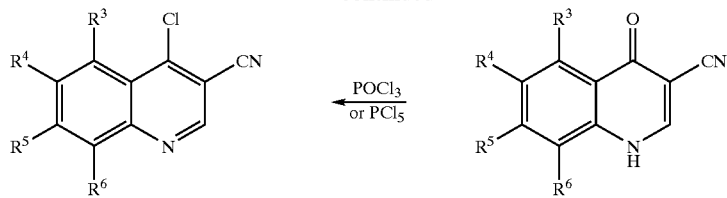

Scheme III illustrates a preferred embodiment for producing the 4-halo-3-cyanoquinoline derivatives of step 4 in Scheme I. The orthoamino ester is treated with dimethylformamide-dimethyl acetal to afford dimethylamidine intermediate. This intermediate is treated at low temperature with the anion of acetonitrile to afford the 3-cyano-4-quinolinone derivatives. The synthesis of 3-cyano-4-chloro-quinoline is effected by treating the 3-cyanoquinolinone with halogenating reagents such as thionyl chloride, oxalyl chloride and phosphorous oxychloride, or phosphorous pentachloride in presence of solvent such as toluene, or carbon tetrachloride. The piperazine products of Scheme I can be produced from the final Scheme III product by repeating step 5 of Scheme I, above.

Scheme IV

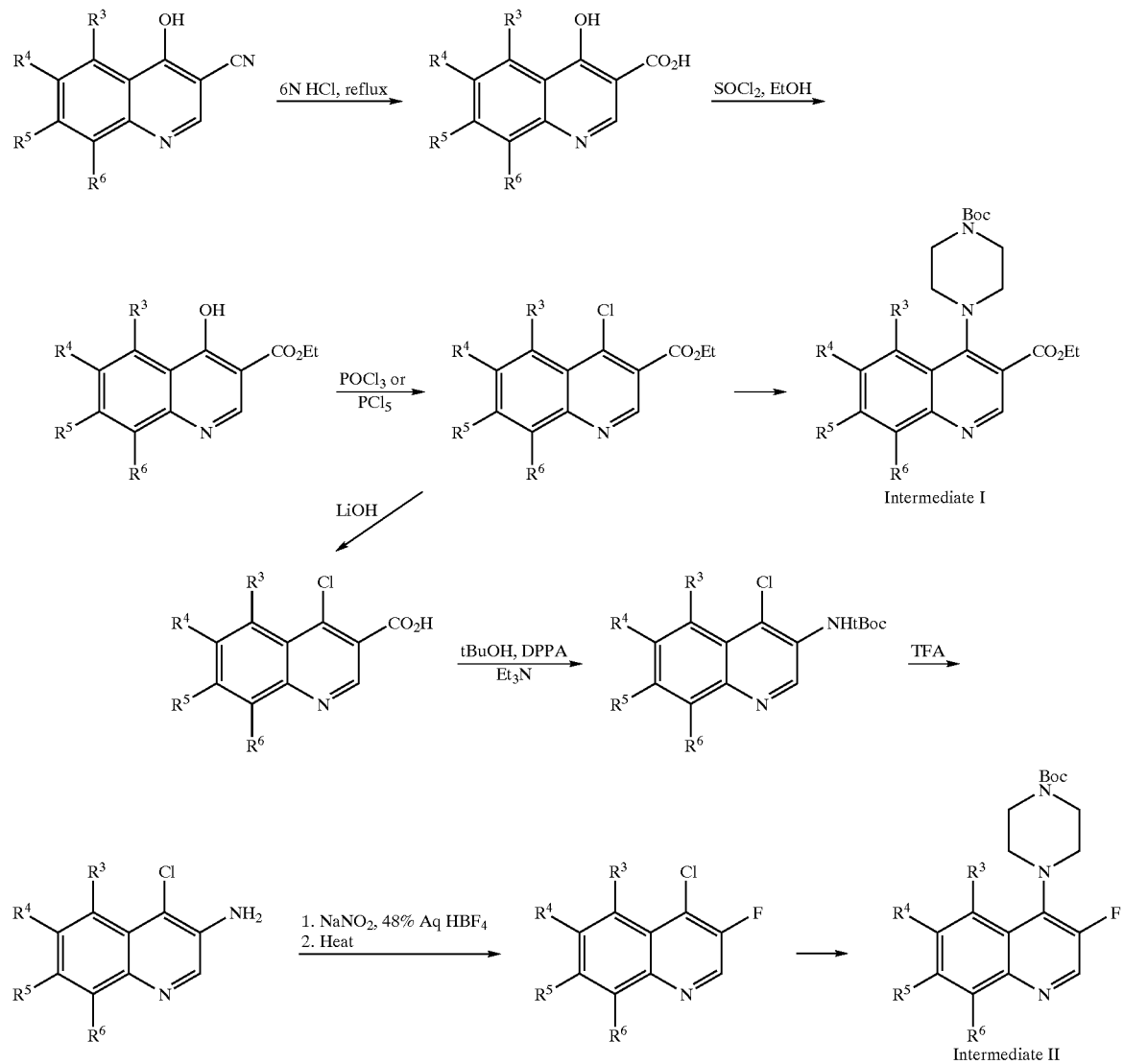

Scheme IV illustrates the synthesis of a tert-butyl-4-[3-Ethylcarboxylate-6-methoxy-7-(phenylmethoxy)quinolin-4-yl]-piperazine carboxylate and tert-butyl-4-[3-Fluoro-6-methoxy-7-(phenylmethoxy)quinolin-4-yl]-piperazine carboxylate compounds, provides an intermediate that can be utilized in the synthesis of various compounds (the scheme can be adapted to produce bicyclic position isomers) as described above for formula I. The cyano functionality of 3-cyano-4-quinolone is hydrolyzed under basic or acidic conditions to afford 3-carboxylic acid intermediate, which is then esterified to afford 3-ethylcarboxylate-4-quinolone intermediate. The synthesis of 3-ethylcarboxylate-4-Cl-quinoline is effected by treating 3-cyano-quinolinone with halogenating reagents such as thionyl chloride, oxalyl chloride and phosphorous oxychloride, or phosphorous pentachloride in presence of solvent such as toluene, or carbon tetrachloride. This intermediate is obtained by treating 3-ethylcarboxylate-4-chloro-quinoline with Boc-piperazine in an appropriate solvent, such as isopropanol, acetonitrile, or THF at room or reflux temperature for 1–6h in presence of base triethylamine or pyridine. The 3-fluoro-4-chloroquinoline is synthesized via 4-chloro-3-carboxylic acid quinolone by curtius rearrangement with diphenyphosphorylazide in presence of t-BuOH to afford 3-Boc-amino intermediate. After removal of Boc functionality under acidic condition, amino group is diazotized with sodium nitrate and the added aqueos fluoboric acid to precipitate diazonium terafluoroborate. This was heated to afford the 3-fluoro-4-chloroquinoline intermediate. The intermediates I and II were converted to various ureas or thioureas as shown in Scheme II. The intermediate form Scheme IV (or its bicyclic position isomer) is debenzylated under hydrogenation conditions followed by alkylation with various alkyl halides. Deprotection of Boc group is effected by trifluoroacetic acid followed by treatment with various isocyanates or thioisocyanates to afford the final urea or thiourea compounds as shown in Scheme II. In cases where the isocyanates are not commercially available, the piperazine intermediate may be treated with phosgene to give a carbamoyl chloride intermediate followed by reaction with various anilines. The piperazine intermediate can also be treated with p-nitrophenyl chloroformate to afford a nitrophenyl carbamate intermediate that can be treated with various anilines to afford the desired ureas.

Such procedures for producing the claimed compounds are merely an illustration of a preferred aspect of the invention. Other procedures and adaptations will be apparent to one of ordinary skill in the art upon views these reaction schemes and the structures of the compounds according to the invention. Such procedures are deemed to be within the scope of the present invention.

Also, the compounds of formula I or Ia and pharmaceutically acceptable salts thereof may exist in the form of adducts with water (hydrates) or various solvents, which are also within the scope of the present invention.

The following non-limiting examples are provided to better illustrate the present invention.

EXAMPLE 1

Preparation of {4-[3-cyano-6-methoxy-7-(3-pipetidylpropoxy)quinolin-4-yl)piperazinyl}-N-[4-(methylethoxy)phenyl]carboxamide

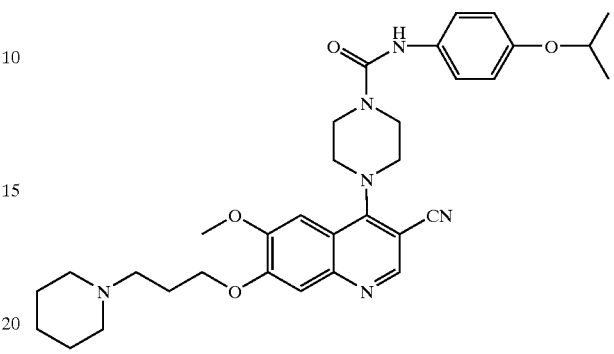

The starting material was prepared as follows:

Step A: Preparation of 4-chloro-6-methoxy-7-(3-pipendylpropoxy)quinoline-3-carbonitrile

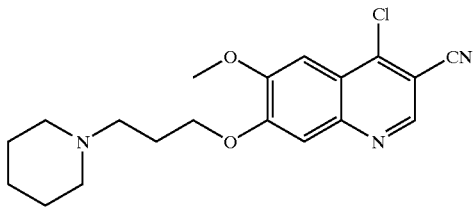

A solution of ethyl 2-amino-5-methoxy-4-(3-piperidylpropoxy)benzoate (1.0 g, 2.98 mmol) and dimethylformamide dimethylacetal (0.84 mL, 5.95 mmol) in 3 mL of DMF was heated at reflux for 3 h. Volatile material was removed and the residue was azeotroped twice with toluene and dried in vacuo.

To a chilled (−78° C.) solution of 2.50 mL n-BuLi (6.22 mmol) in 2.30 mL THF was added THF solution (2 mL) of CH3CN (0.341 mL, 6.53 mmol) dropwise under argon. After 20 min at −78° C. added formamidine product from step 1 in THF (2.5 mL) dropwise over 10 min. The reaction was stirred at −78° C. for 1 h and then quenched with 0.81 mL of glacial acetic acid. The mixture was warmed to RT and the solvent evaporated. The residue was purified by reverse phase HPLC to afford 0.425 g of 4-hydroxy-6-methoxy-7-(3-piperidylpropoxy)quinoline-3-carbonitrile as white solid. MS(ES) 342 (M+H)

A slurry of 4-hydroxyquinoline (0.700 g, 1.45 mmol) in SOCl 2 (5 mL) was treated with 0.400 mL of DMF. This mixture was heated at 90° C. for 30 min during that time all the starting material was consumed by HPLC. The solvent was evaporated in vacuo and then azetroped with toluene to remove excess thionyl chloride. The residue was suspended in H2O/CH2Cl2 (1:1) to this added 20% K2CO3 at −10° C. till pH ~9 and then the organic layer was separated. The organic layer was dried, filtered and evaporated to afford 4-chloro-6-methoxy-7-(3-piperidylpropoxy)quinoline-3-carbonitrile as a tan solid (0.377 g, 73%). MS(ES) 360.1 (M+H)

Step B: Preparation of {4-[3-cyano-6-methoxy-7-(3-piperidylpropoxy)quinolin-4-yl)piperazinyl}-N-[4-(methylethoxy)phenyl]carboxamide To the DMF solution (3 mL) of the 4-chloroquinoline (0.175 g, 0.487 mmol) from step A added K2CO3 (0.155 g, 1.10 mmol) followed by N-[4-(methylethoxy)phenyl]piperazinylcarboxamide hydrochloride (0.169 g, 0.535 mmol). The reaction mixture was heated to 40° C. overnight, during that period starting materials were consumed. After cooling diluted with EtOAc/water and the layers were separated. The organic layer was dried, filtered and evaporated to afford desired product as a crude residue. The crude residue was purified by RP-HPLC to afford {4-[3-cyano-6-methoxy-7-(3-piperidylpropoxy)quinolin-4-yl)piperazinyl}-N-[4-(methylethoxy)phenyl]carboxamide as the desired product (0.195 g, 69%). MS(ES) 587.3 (M+H)

EXAMPLE 2

Preparation of N-(4-cyanophenyl)[4-[3-cyano-6-methoxy-7-(3-piperidypropoxy)quinolin-4-yl]piperazinyl}carboxamide

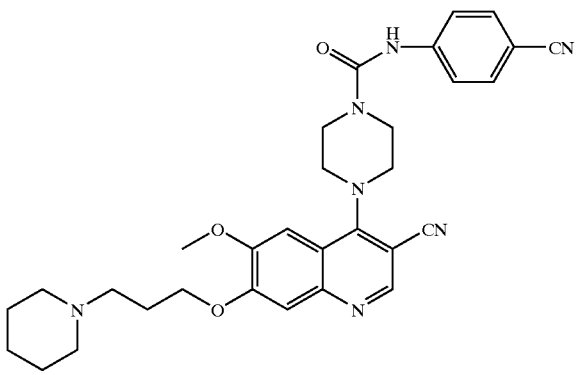

To the DMF solution (2 mL) of 4-chloro-6-methoxy-7-(3-piperidylpropoxy)quinoline-3-carbonitrile (0.125 g, 0.348 mmol) added K2CO3 (0.144 g, 1.04 mmol) followed by N-[4-cyanophenyl]piperazinylcarboxamide (0.11 g, 0.415 mmol) and the reaction was heated at 65° C. overnight. The solvent was evaporated and the residue purified by RP-HPLC to afford desired product N-(4-cyanophenyl)[4-[3-cyano-6-methoxy-7-(3-piperidypropoxy)quinolin-4-yl]piperazinyl}carboxamide as yellow fluffy solid (90 mg, 50%). MS(ES) 554 (M+H).

EXAMPLE 3

Preparation of {4-[3-ethylcarboxylate-6-methoxy-7-(3-piperidylpropoxy)quinolin-4-yl)piperazinyl}-N-[4-(methylethoxy)phenyl]carboxamide

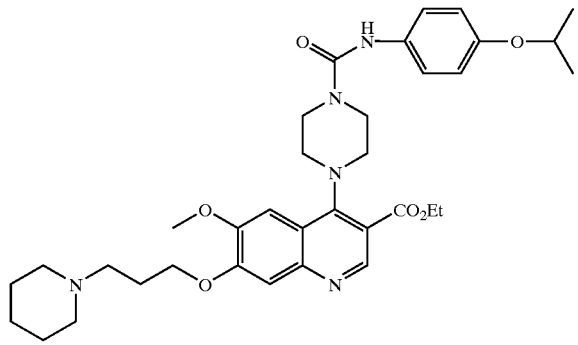

The starting material was prepared as follows:
Step A: Preparation of 4-chloro-6-methoxy-7-(3-piperidylpropoxy)quinoline-3-carboxylic Acid Ethyl Ester

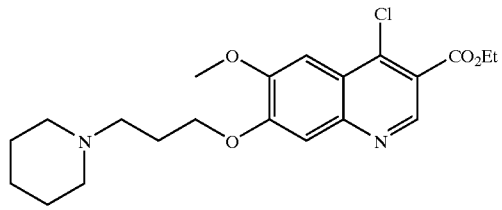

A slurry of 4-hydroxy-6-methoxy-7-(3-piperidylpropoxy)quinoline-3-carbonitrile (0.700 g, 1.45 mmol) was refluxed in 6N HCl for 18 h to afford 4-hydroxy-6-methoxy-7-(3-piperidylpropoxy)quinoline-3-carboxylic acid. This was dissolved in ethanol (5 mL) and to it added thionyl chloride (1 mL) and reaction was heated at 60° C. overnight to 4-hydroxy-6-methoxy-7-(3-piperidin-1-yl-propoxy)-quinoline-3-carboxylic acid ethyl ester as a viscous oil (0.500 g). The above intermediate was suspended in SOCl2 (5 mL) was treated with 0.400 mL of DMF. This mixture was heated at 90° C. for 30 min during that time all the starting material was consumed by HPLC. The solvent was evaporated in vacuo and then azetroped with toluene to remove excess thionyl chloride. The residue was suspended in H2O/CH2Cl2 (1:1) to this added 20% $K_2CO_3$ at −10° C. till pH ~9 and then the organic layer was separated. The organic layer was dried, filtered and evaporated to afford 4-chloro-6-methoxy-7-(3-piperidylpropoxy)quinoline-3-carboxylic acid ethyl ester as a tan solid (0.377 g, 73%). MS(ES) 407 (M+H)

Step B: Preparation of 4-{4-(4-Isopropoxy-phenylcarbamoyl)-piperazin-1-yl]-6-methoxy-7-(3-piperidin-1-yl-propoxy)-quinolin-3-carboxylic Acid Ethyl Ester To the DMF solution (3 mL) of the 4-chloroquinoline (0.175 g, 0.487 mmol) from step A added K2CO3 (0.155 g, 1.10 mmol) followed by N-[4-(methylethoxy)phenyl]piperazinylcarboxamide hydrochloride (0.169 g, 0.535 mmol). The reaction mixture was heated to 40° C. overnight, during that period starting materials were consumed. After cooling diluted with EtOAc/water and the layers were separated. The organic layer was dried, filtered and evaporated to afford desired product as a crude residue. The crude residue was purified by RP-HPLC to afford 4-{4-(4-

Isopropoxy-phenylcarbamoyl)piperazin-1-yl]-6-methoxy-7-(3-piperidin-1-yl-propoxy)-quinolin-3-carboxylic acid ethyl ester (0.170 g, 50%). MS(ES) 634 (M+H)

EXAMPLE 4

Preparation of 4-[3-Fluoro-6-methoxy-7-(3-piperidin-1-yl-propoxy)-quinolin-4-yl]-piperazine-1-carboxylic Acid(4-isopropoxyphenyl)amide

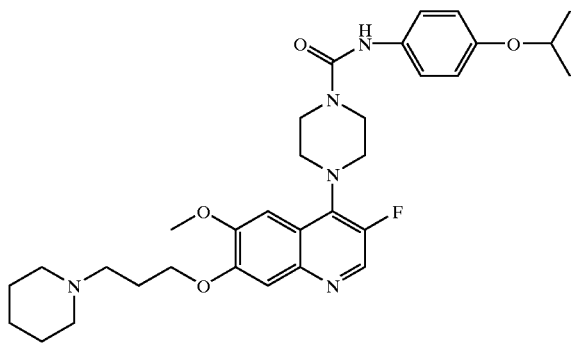

The starting material was prepared as follows:
Step A: Preparation of 4-chloro-3-Fluoro-6-methoxy-7-(3-piperidylpropoxy)quinoline

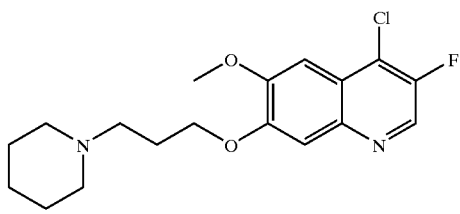

Step 1

4-chloro-6-methoxy-7-(3-piperidylpropoxy)quinoline-3-carboxylic Acid (1 g)was suspended in DMF (10 ml) with stirring under nitrogen atmosphere, tBuOH (4 ml) was added followed by thiethylamine (3.1 ml) and then diphenylphosphorylazide (2.5ml) was added. The reaction was then heated to 100° C. for 8 hrs with stirring under nitrogen atmosphere. The solvent was evaporated and extracted the crude product with dichloromethane. The desired product was isolated after flash chromatography eluting with 2%methanol in dichloromethane to give [4-chloro-6-methoxy-7-(3-piperidin-1-yl-propoxy)-quinolin-3-yl]-carbamic acid tert-butylester (2.1 g, 65%)

Step 2

[4-chloro-6-methoxy-7-(3-piperidin-1-yl-propoxy)-quinolin-3-yl]-carbamic acid tert-butylester (1.8 g) was dissolved in dichloromethane and added trifluoroacetic acid (2 ml) and stirred at room temperature for 2 h. This was carefully basified with ammonium hydroxide solution and extracted the desired amino product with ethyl acetate. The solvent was evaporated to give 4-chloro-6-methoxy-7-(3-piperidin-1-yl-propoxy)-quinolin-3-ylamine (0.500 g). MS(ES) 350 (M+H).

Step 3

4-chloro-6-methoxy-7-(3-piperidin-1-yl-propoxy)-quinolin-3-ylamine (0.300 g) was dissolved in THF (5 ml) with stirring and then cooled in ice-water bath to below 0° C., to this added 48% aqueous fluoboric acid (0.7 ml) and mixture stirred for 10 mins. A solution of sodium nitrite (0.10 sg) in water (1 ml) was added keeping the temperature below 10° C. The reaction mixture was the stirred for 1 hr, during that time yellow solid precipitated. This solid was filtered, dried to give 4-chloro-6-methoxy-7-(3-piperidin-1-yl-propoxy)-quinolin-3-diazonium tetrafluoroborate (0.250 g, 80%)

Step 4

4-chloro-6-methoxy-7-(3-piperidin-1-yl-propoxy)-quinolin-3-diazonium tetrafluoroborate (0.200 g) was carefully heated to 150° C., where decomposition takes place with gas evolution. After gas evolution ceased, the reaction was cooled and the residue purified by flash chromatography eluting with dichloromethane/methanol 98:2 to 4-chloro-3-fluoro-6-methoxy-7-(3-piperidin-1-yl-propoxy)quinoline (0.090 g, 30%). MS(ES) 353 (M+H)

Step B: Preparation of 4-[3-Fluoro-6-methoxy-7-(3-piperidin-1-yl-propoxy)-quinolin-4-yl]-piperazine-1-carboxylic Acid(4-isopropoxyphenyl)amide To the DMF solution (3 mL) of the 4-chloroquinoline (0.070 g, 0.2 mmol) from step 4 added K2CO3 (0.055 g, 0.3 mmol) followed by N-[4-(methylethoxy)phenyl] piperazinylcarboxamide hydrochloride (0.080 g, 0.235 mmol). The reaction mixture was heated to 40° C. overnight, during that period starting materials were consumed. After cooling diluted with EtOAc/water and the layers were separated. The organic layer was dried, filtered and evaporated to afford desired product as a crude residue. The crude residue was purified by RP-HPLC to afford 4-[3-Fluoro-6-methoxy-7-(3-piperidin-1-yl-propoxy)-quinolin-4-yl]-piperazine-1-carboxylic acid(4-isopropoxyphenyl)amide (0.100 g, 79%). MS(ES) 634 (M+H). The solvent was evaporated in vacuo and then azetroped with toluene to remove excess thionyl chloride. The residue was suspended in H2O/CH2Cl2 (1:1) to this added 20% $K_2CO_3$ at −10° C. till pH ~9 and then the organic layer was separated. The organic layer was dried, filtered and evaporated to afford 4-chloro-6-methoxy-7-(3-piperidylpropoxy)quinoline-3-carboxylic acid ethyl ester as a tan solid (0.377 g, 73%). MS(ES) 407 (M+H)

Step B: Preparation of 4-{4-(4-Isopropoxy-phenylcarbamoyl)-piperazin-1-yl]-6-methoxy-7-(3-piperidin-1-yl-propoxy)-quinolin-3-carboxylic Acid Ethyl Ester To the DMF solution (3 mL) of the 4-chloroquinoline (0.175 g, 0.487 mmol) from step A added K2CO3 (0.155 g, 1.10 mmol) followed by N-[4-(methylethoxy)phenyl] piperazinylcarboxamide hydrochloride (0.169 g, 0.535 mmol). The reaction mixture was heated to 40° C. overnight, during that period starting materials were consumed. After cooling diluted with EtOAc/water and the layers were separated. The organic layer was dried, filtered and evaporated to afford desired product as a crude residue. The crude residue was purified by RP-HPLC to afford 4-}4-(4-Isopropoxy-phenylcarbamoyl)piperazin-1-yl]-6-methoxy-7-(3-piperidin-1-yl-propoxy)-quinolin-3-carboxylic acid ethyl ester (0.170 g, 50%). MS(ES) 580 (M+H)

The pharmacological activities of the compounds of the present invention are obtained by following the test example procedures as follows, for example.

Biological Test Assay Type I

Inhibitory Effect on Compounds on Autophosphorylation of Platelet Derived Growth Factor β-PDGF Receptor (1) HR5 Phosphorylation Assay The HR5 cell line is a cell line of CHO cells engineered to overexpress human β-PDGFR, which cell line is available from the ATCC. The expression level of β-PDGFR in HR5 cells is around $5 \times 10^4$ receptor per cell. For the phosphorylation assay according to the invention, HR5 cells were grown to confluency in 96-well microtiter plates under standard tissue culture conditions, followed by serum-starvation for 16 hours. Quiescent cells were incubated at 37° C. without or with increasing concentrations of the test compound (0.01–30 uM) for 30 minutes followed by the addition of 8 nM PDGF BB for 10 minutes. Cells were lysed in 100 mM Tris, pH 7.5, 750 mM NaCl, 0.5% Triton X-100, 10 mM sodium pyrophosphate, 50 mM NaF, 10 ug/ml aprotinin, 10 ug/ml leupeptin, 1 mM phenylmethylsulfonyl fluoride, 1 mM sodium vanadate, and the lysate was cleared by centrifugation at 15,000× g for 5 minutes. Clarified lysates were transferred into a second microtiter plate in which the wells were previously coated with 500 ng/well of 1B5B11 anti-β-PDGFR mAb, and then incubated for two hours at room temperature. After washing three times with binding buffer (0.3% gelatin, 25 mM Hepes pH 7.5, 100 mM NaCl, 0.01% Tween-20), 250 ng/ml of rabbit polyclonal anti-phosphotyrosine antibody (Transduction Laboratory) was added and plates were incubated at 37° C. for 60 minutes. Subsequently, each well was washed three times with binding buffer and incubated with 1 ug/ml of horse radish peroxidase-conjugated anti-rabbit antibody (Boehringer Mannheim) at 37° C. for 60 minutes. Wells were washed prior to adding ABTS (Sigma), and the rate of substrate formation was monitored at 650 nm. The assay results are reported as $IC_{50}$ (expressed as the concentration of a compound according to the invention that inhibits the PDGF receptor phosphorylation by 50%) as compared to control cells that are not exposed to a compound according to the invention.

(2) MG63 Phosphorylation Assay

The MG63 cell line is a human osteosarcoma tumor cell line available from the ATCC. This assay is for measuring endogenous β-PDGFR phosphorylation in MG63 cells. The assay conditions are the same as those described at for HR5 cell, except that PDGF-BB stimulation is provided in the presence or absence of 45% human plasma. The HR5 assay results are reported as an $IC_{50}$ (expressed as the concentration of a compound according to the invention that inhibits the PDGF receptor phosphorylation by 50%) as compared to control cells that are not exposed to a compound according to the invention. Examples of such $IC_{50}$ results in the MG63 assay for compounds according to the invention are set forth below in the Table 1.

TABLE 1

| Example | MG63 w/human plasma $IC_{50}(\mu M)$ | HR5 $IC_{50}(\mu M)$ |
|---|---|---|
| Example 1 | 0.134 | 0.060 |
| Example 2 | 0.103 | 0.085 |

Biological Test Assay Type 2
Growth Inhibition Against Smooth Muscle Cells

Vascular smooth muscle cells are isolated from a pig aorta by explanation and used for the test. The cells are put into wells of a 96-well plate (8000 cells/well) and cultured in Dulbeccois modified Eagle's medium (DMEM; Nissui Pharmaceutical Co., Ltd.) containing 10% fetal bovine serum (FBS; Hyclone) for 4 days. Then, the cells are further cultured in DMEM containing 0.1% FBS for 3 days, and are synchronized at the cell growth stationary phase.

To each well is added DMEM containing 0.1% FBS and a test sample at a varied concentration, and the cell growth is brought about by PDGF-BB (SIGMA, final concentration: 20 ng/ml). After culturing for 3 days, the cell growth is measured using a cell growth assay kit (Boehringer Mannheim) according to the XTT method [J. Immunol. Methods, 142, 257–265 (1991)], and the cell growth score is calculated by the following equation.

Cell growth score=100×{1-(M-PO)/(P100-PO)} wherein P100=absorbance by XTT reagent when stimulated by PDGF-BB; PO=absorbance by XTT reagent when not stimulated by PDGF-BB, and M=absorbance by XTT reagent after addition of a sample when stimulated by PDGF-BB.

The test result is expressed as the concentration of a test compound which inhibits the cell growth by 50% (IC50).

Biological Test Assay Type 3
Inhibitory Effect on Hypertrophy of Vascular Intima Male SD rats (weight: 375–445 g, Charles River, golden standard) are anesthetized with sodium pentobarbital (50 mg/kg, i.p.), and then the neck of each animal is incised by the median incision, followed by retrograde insertion of a balloon catheter (2F, Edwards Laboratories) into the left external carotid. After the above treatment is repeated seven times, the catheter is pulled out, the left external carotid is ligated, and the wound is sutured. A test compound is suspended in a 0.5% solution of Tween 80 in an aqueous solution of sodium chloride to a concentration of 20 mg/ml in the case of intraperitoneal administration and in a 0.5% solution of methyl cellulose 400 to a concentration of 6 mg/ml in the case of oral administration. The suspension is administered once a day in the case of intraperitoneal administration and once or twice a day in the case of oral administration for a period of 15 days starting on the day before the balloon injury. On the 14th day after the balloon injury, the animal is killed and its left carotid is extirpated. The tissues are fixed with formalin, wrapped in paraffin and sliced, followed by Elastica Wangeeson staining. The area of the cross section of the vascular tissues (intima and media) is measured with an image analyzer (Luzex F, NIRECO) and the intima/media area ratio (I/M) is regarded as the degree of hypertrophy of the vascular intima.

From the results obtained, it is apparent when the hypertrophy of vascular intima is significantly inhibited by administration of the compounds of the present invention.

Biological Test Assay Type 4
Evaluation by the Use of a Rat Adjuvant Arthritis Model Dead cells of Mycobacterium bacterium (Difco Laboratories Inc.) are disrupted in agate mortar and suspended in liquid paraffin to the final concentration of 6.6 mg/ml, followed by sterilization with high pressure steam. Then, 100 ml of the suspension is subcutaneously injected into the right hind foot pad of each animal of groups of female 8-weeks-old Lewis rats (Charles River Japan) (6 animals/group) to induce adjuvant arthritis. A test compound is suspended in a 0.5% solution of methyl cellulose to the final concentration of 3 mg/ml, and from just before the induction of arthritis, the suspension is orally administered in an amount of 100 ml/100 g of the body weight once a day, 5 days a week. To a control group is administered a 0.5% solution of methyl cellulose. A normal group is given no adjuvant treatment or test compound administration. The administration of the test compound is continued till the 18th day after the adjuvant treatment. On the 17th day, the number of leukocytes in peripheral blood are counted, and on the 18th day, all the blood is collected, followed by dissection.

The change in body weight with the passage of time, the change of edema in hind foot with the passage of time, the weight of spleen and thymus, the number of leukocytes in peripheral blood, the hydroxyproline content of urine, the glucosaminoglycan content of urine, the SH concentration in serum, the concentration of nitrogen monoxide in serum and the concentration of mucoprotein in serum are measured and evaluated. The volume of each of both hind feet are measured using a rat's hind foot edema measurement device (TK-101, Unicom). The number of leukocytes in peripheral blood are counted using an automatic multichannel blood cell counter (Sysmex K-2000, Toa Iyo Denshi Co., Ltd.). The hydroxyproline content of urine is measured according to the method described in Ikeda, et al., Annual Report of Tokyo Metropolitan Research Laboratories P. H., 36, 277 (1985), and the glucosaminoglycan content is measured according to the method described in Moriyama, et al., Hinyo Kiyo, 40, 565 (1994) and Klompmakers, et al., Analytical Biochemistry, 153, 80 (1986). The SH concentration in serum is measured according to the method described in Miesel, et al., Inflammation, 17, 595 (1993), and the concentration of nitrogen monoxide is measured according to the method of Tracey, et al., Journal of Pharmacology & Experimental Therapeutics, 272, 1011 (1995). The concentration of mucoprotein is measured using Aspro GP Kit (Otsuka Pharmaceutical Co., Ltd.). The percentage inhibition for each indication is calculated according to the following equation.

% Inhibition={(Control group−Compound-administered group)/(Control group−Normal group)}×100.

From the results obtain from such assays, it is apparent when the compound according to the invention inhibits the occurrence of adjuvant arthritis.

Biological Test Assay Type 5

Activity on a Mesangial Proliferative Glomerulonephritis Model

Anti-rat Thy-1.1 monoclonal antibody OX-7 (Sedaren) is administered to male Wister-Kyoto rats (Charles River Japan, 160 g, 6 animals/group) in an amount of 1.0 mg/kg by intravenous administration through the tail vein. A test compound is suspended in a 0.5% solution of methylcellulose and the resulting suspension is administered to each of the rats twice a day for a period of 7 days starting on the day before the administration of OX-7. On the 7th day after the OX-7 administration, when mesangial cell growth and extracellular matrix hypertrophy become prominent, the left kidney of each rat is extirpated, fixed with 20% buffered formalin for 6 hours and wrapped in paraffin, followed by slicing. The obtained pieces are subjected to immune tissue staining using antibody PC10 (DAKO) against an intranuclear antigen of proliferative cells. After comparative staining with Methyl Green staining solution using diaminobenzidine as a color developer, the paraffin pieces are enclosed. Half of the glomeruli in a kidney piece are observed and the number of the cells in one glomerulus which are positive to the intranuclear antigen of proliferative cells are calculated. The test for the significance of difference is carried out by the Wilcoxon test.

From such results, it is apparent when the compounds according to the present invention show alleviating activity on mesangial proliferative glomerulonephritis.

The compounds of formula (I) and formula (Ia) and pharmaceutically acceptable salts thereof can be administered as such, but it is usually preferred to administer them in the form of pharmaceutical compositions, which are used for animals and human beings.

It is preferred to employ the administration route which is the most effective for the treatment. For example, administration is made orally or non-orally by intrarectal, intraoral, subcutaneous, intramuscular or intravenous administration.

Examples of the forms for administration are capsules, tablets, granules, powders, syrups, emulsions, suppositories and injections.

Liquid compositions such as emulsions and syrups which are appropriate for oral administration can be prepared using water, sugars such as sucrose, sorbitol and fructose, glycols such as polyethylene glycol and propylene glycol, oils such as sesame oil, olive oil and soybean oil, preservatives such as benzoates, flavors such as strawberry flavor and peppermint, etc.

Capsules, tablets, powders and granules can be prepared using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, etc.

Compositions suitable for non-oral administration preferably comprise a sterilized aqueous preparation containing an active compound which is isotonic to the recipient's blood. For example, injections are prepared using a carrier which comprises a salt solution, a glucose solution, or a mixture of a salt solution and a glucose solution.

Compositions for topical application are prepared by dissolving or suspending an active compound in one or more kinds of solvents such as mineral oil, petroleum and polyhydric alcohol, or other bases used for topical drugs.

Compositions for intestinal administration are prepared using ordinary carriers such as cacao fat, hydrogenated fat and hydrogenated fat carboxylic acid, and are provided as suppositories.

The compositions for non-oral administration may additionally be formulated to contain one or more kinds of additives selected from glycols, oils, flavors, preservatives (including antioxidants), excipients, disintegrating agents, lubricants, binders, surfactants and plasticizers which are used for the preparation of compositions for oral administration.

The effective dose and the administration schedule for each of the compounds of formula (I) or a pharmaceutically acceptable salt thereof will vary depending on the administration route, the patient's age and body weight, and the type or degree of the diseases to be treated. However, it is generally appropriate to administer a compound of formula (I) or a pharmaceutically acceptable salt thereof in a dose of 0.01–1000 mg/adult/day, preferably 5–500 mg/adult/day, in one to several parts.

All the compounds of the present invention can be immediately applied to the treatment of kinase-dependent diseases of mammals as kinase inhibitors, specifically, those relating to tyrosine kinase. Specifically preferred are the compounds which have $IC_{50}$ within the range of 10 nM–10 $\mu$M. Even more preferred are compounds which have $IC_{50}$ within the range of 10 nM to −1 $\mu$M. Most preferred are compounds which have an $IC_{50}$ value which is less than 1 $\mu$M.

Specific compounds of the present invention which have an activity to specifically inhibit one of the three types of protein kinase (for example, kinase which phosphorylates tyrosine, kinase which phosphorylates tyrosine and threonine, and kinase which phosphorylates threonine) can be selected. Tyrosine kinase-dependent diseases include hyperproliferative malfunction which is caused or maintained by abnormal tyrosine kinase activity. Examples thereof include psoriasis, pulmonary fibrosis, glomerulonephritis, cancer, atherosclerosis and anti-angiopoiesis (for example, tumor growth and diabetic retinopathy). Current knowledge of the relationship between other classes of kinase and specific diseases is insufficient. However, compounds having specific PTK-inhibiting activity have a useful treatment effect. Other classes of kinase have also been recognized in the same manner. Quercetin, genistein and staurosporin, which are all PTK-inhibitors, inhibit many kinds of protein kinase in addition to tyrosine kinase. However, as a result of their lack of the specificity, their cytotoxicity is high. Therefore, a PTK-inhibitor (or an inhibitor of other classes of kinase) which is apt to bring about undesirable side effects because of the lack of selectivity can be identified by the use of an ordinary test to measure cytotoxicity.

The term "effective amount" is an amount necessary for administering the compound in accordance with the present invention to provide the necessary effect such as inhibiting the phosphorylation of kinases or treating disease states in a mammal. In accordance with the present invention, a suitable single dose size is a dose that is capable of preventing or treating an animal with a disease when administered one or more times over a suitable time period. Doses can vary depending upon the disease being treated. For example, in the treatment of hypersensitivity, a suitable single dose can be dependent upon the nature of the immunogen causing the hypersensitivity.

The "effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

Prodrug Derivatives of Compounds

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpytrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

An effective administration protocol (i.e., administering a therapeutic composition in an effective manner) comprises suitable dose parameters and modes of administration that result in prevention or treatment of a disease. Effective dose parameters and modes of administration can be determined using methods standard in the art for a particular disease. Such methods include, for example, determination of survival rates, side effects (i.e., toxicity) and progression or regression of disease. For example, the effectiveness of dose parameters and modes of administration of a therapeutic composition of the present invention can be determined by assessing response rates. Such response rates refer to the percentage of treated patients in a population of patients that respond with either partial or complete remission.

Dosage formulations of the compounds of the invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of the invention typically will be about 3–11, more preferably about 5–9 and most preferably about 7–8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, oral dosage formulations and topical formulations such as ointments, drops and dermal patches. The compounds of the invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of the invention may also be delivered by the use of antibodies, antibody fragments, growth factors, hormones, or other targeting moieties, to which the compound molecules are coupled. The compounds of the invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartamide-phenol, or polyethyleneoxide-polylysine with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds and compositions of the invention can be administered orally or parenterally in an effective amount within the dosage range of about 0.001 to about 1000 mg/kg, preferably about 0.01 to about 100 mg/kg and more preferably about 0.1 to about 20 mg/kg. Advantageously, the compounds and composition of the invention may be administered several times daily. Other dosage regimens may also be useful (e.g. single daily dose and/or continuous infusion).

Typically, about 0.5 to about 500 mg of a compound or mixture of compounds of the invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Acid addition salts include hydrochlorides, hydrobromides, hydrolodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates. Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts. Prodrugs of compounds of formula (1) include those compounds, for example esters, alcohols or aminos, which are convertible in vivo by metabolic means, e.g. by hydrolysis, reduction, oxidation or transesterification, to compounds of formula (1). Particularly useful salts of compounds according to the invention include pharmaceutically acceptable salts, especially acid addition pharmaceutically acceptable salts. Next, the pharmacological activity of the compounds of the present invention are specifically explained by test examples.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. The examples given above are non-limiting in that one of ordinary skill in view of the above will readily envision other permutations and variations on the invention without departing from the principal concepts. Such permutations and variations are also within the scope of the present invention. All the patents, journal articles and other documents discussed or cited above are herein incorporated by reference. The invention is further illustrated with reference to the claims that follow thereto.

What is claimed is:

1. A compound having the following formula:

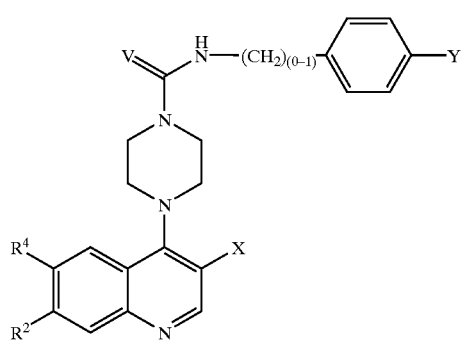

Ia wherein:

V is O or S;

X is —(CH$_2$)$_{1-2}$—OH, —CH$_2$—C(=O)—O(—CH$_2$)$_{0-8}$—CH$_3$, —CH$_2$—C(=O)—H, or (—CH$_2$)$_{0-1}$—CN, F or Cl;

Y is —CN, —Br, —CF$_3$, —O—C$_{1-8}$ alkyl that is independently straight or branched chained, —O-phenyl, —O-naphthyl, —O-indolyl or —O-isoquinolinyl;

R$^2$ and R$^4$ are each independently a member selected from the group consisting of:

—O—CH$_3$, —O(—CH$_2$)—CH$_3$, —O—CH$_2$—CH=CH$_2$, —O—CH$_2$—C≡CH and —O(—CH$_2$)$_{2-3}$—R$^{2a}$;

R$^{2a}$ is a member selected from the group consisting of:

—OH, —O—CH$_3$, —O—CH$_2$—CH$_3$, —NH$_2$, —N(—CH$_3$)$_2$, —NH(—CH$_2$-Phenyl), —NH(-Phenyl), —CN,

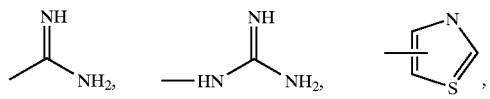

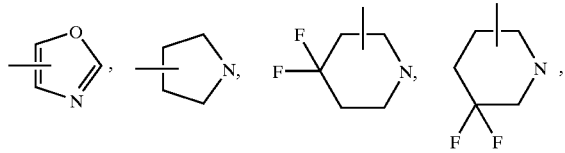

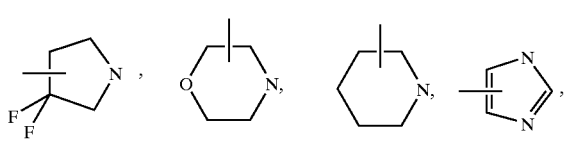

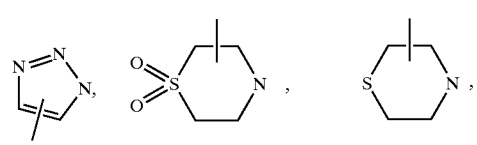

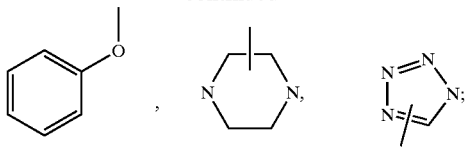

or all pharmaceutically acceptable salts or hydrates thereof.

2. A compound of claim 1 wherein:

V is O or S;

X is CN, F or Cl;

Y is —CN, —O—C$_{1-8}$ alkyl that is independently straight or branched chained, —O-phenyl, —O-naphthyl, —O-indolyl or —O-isoquinolinyl;

R$^2$ and R$^4$ are each different and independently a member selected from the group consisting of:

—O—(CH$_2$—)$_{0-1}$—CH$_3$ and —O(—CH$_2$)$_{2-3}$—R$^{2a}$;

R$^{2a}$ is a member selected from the group consisting of:

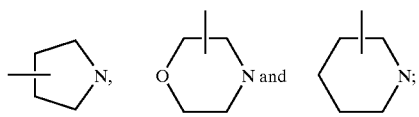

or all pharmaceutically acceptable salts or hydrates thereof.

3. A compound of claim 1 selected from the group consisting of:

N-(4-indol-5-yloxyphenyl){4-[3-cyano-6-methoxy-7-(2-methoxyothoxy)quinolin-4-yl]piperazinyl}carboxamide

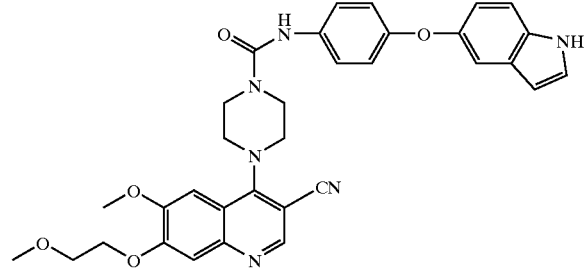

N-(4-indol -4yloxyphenyl){4-[3-cyano-6-methoxy-7-(2-methoxyethoxy)quinolin-4-yl]piperazinyl}carboxamide

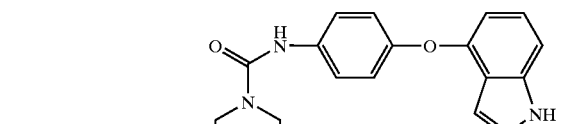

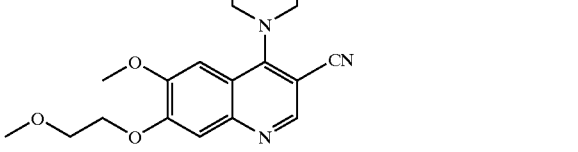

{4-[3-cyano-6-methoxy-7-(2-methoxyethoxy)quinazolin-4-yl]piperazinyl}-N-(4-naphthyloxyphenyl)carboxamide

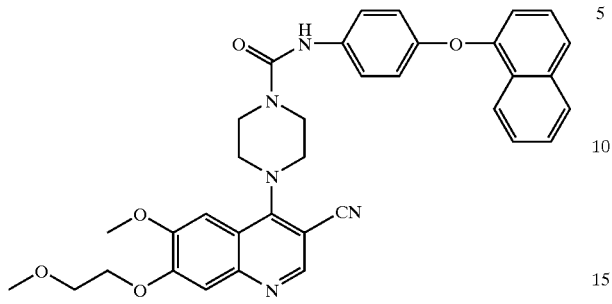

{4-[3-cyano-6-methoxy-7-(2-methoxyethoxy)quinolin-4-yl]piperazinyl}-N-(4-(2-naphthyloxy)phenyl)carboxamide

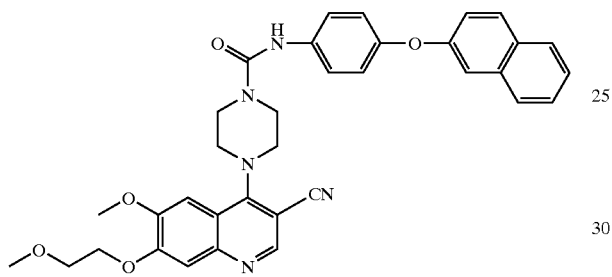

N-(4-(5-isoquinolyloxy)phenyl){4-[3-cyano-6-methoxy-7-(2-methoxyethoxy)quinolin-4-yl]piperazinyl}carboxamide

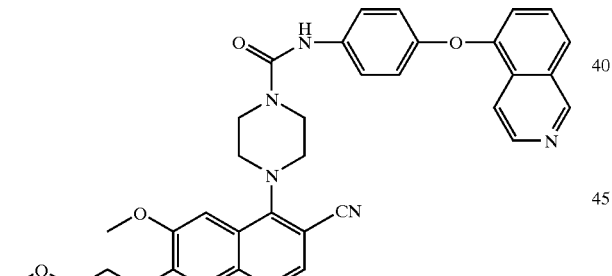

{4-[3-cyano-6-methoxy-7-(2-methoxyethoxy)quinolin-4-yl]piperazinyl}-N-(4-phenoxyphenyl)carboxamide

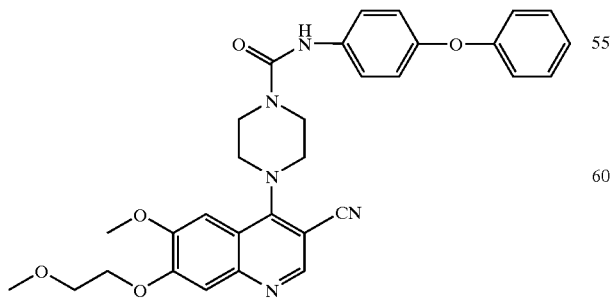

{4-[3-cyano-6-methoxy-7-(2-methoxyethoxy)quinolin-4-yl]piperazinyl}-N-[4-(methylethoxy)phenyl]carboxamide

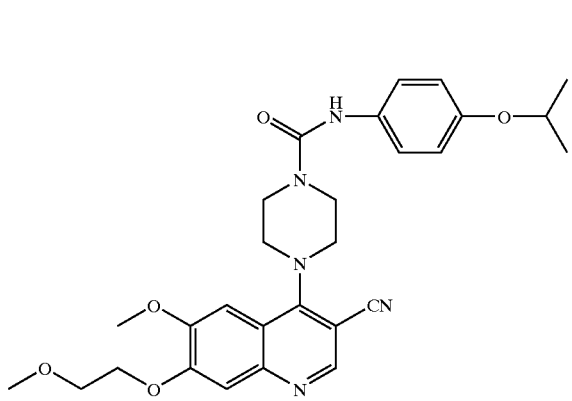

N-(4-cyanophenyl){4-[3-cyano-6-methoxy-7-(2-methoxyethoxy)quinolin-4-yl]piperazinyl}carboxamide

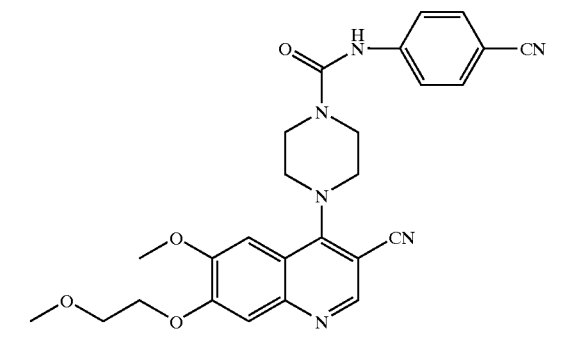

{4-[3-cyano-6-methoxy-7-(2-piperidylethoxy)quinolin-4-yl]piperazinyl}-N-[4-(methylethoxy)phenyl]carboxamide

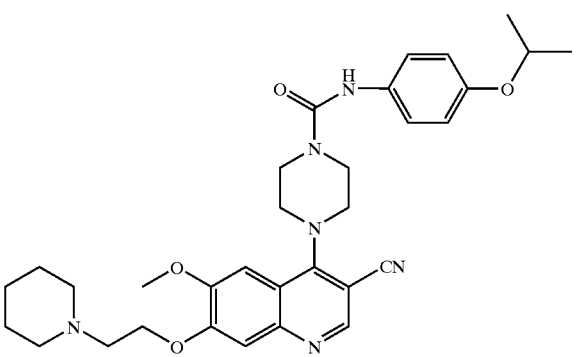

| 83 | 84 |
|---|---|
| N-(4-cyanophenyl){4-[3-cyano-6-methoxy-7-(2-piperidylethoxy)quinolin-4-yl]piperazinyl}carboxamide | N-(4-cyanophenyl){4-[3-cyano-6-methoxy-7-(3-morpholin-4-ylpropoxy)quinolin-4-yl]piperazinyl}carboxamide |

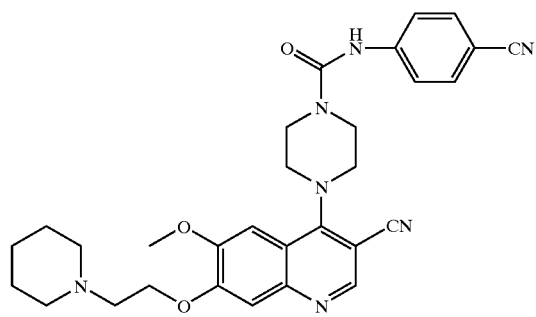

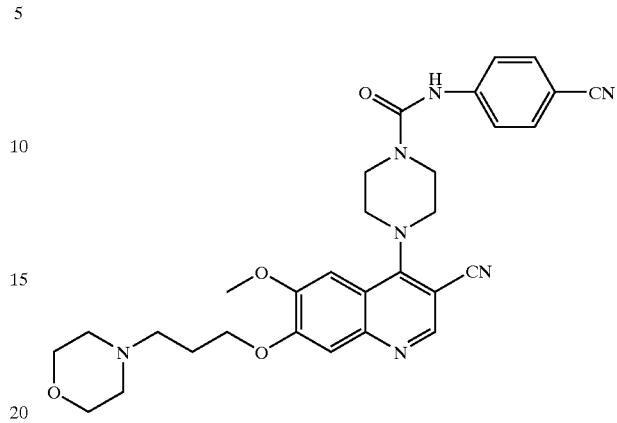

{4-[3-cyano-6-methoxy-7-(3-piperidylpropoxy)quinolin-4-yl]piperazinyl}-N-[4-(methylethoxy)phenyl]carboxamide {4-[3-cyano-6-methoxy-7-(3-pyrrolidinylpropoxy)quinolin-4-yl]piperazinyl}-N-[4-(methylethoxy)phenyl]carboxamide

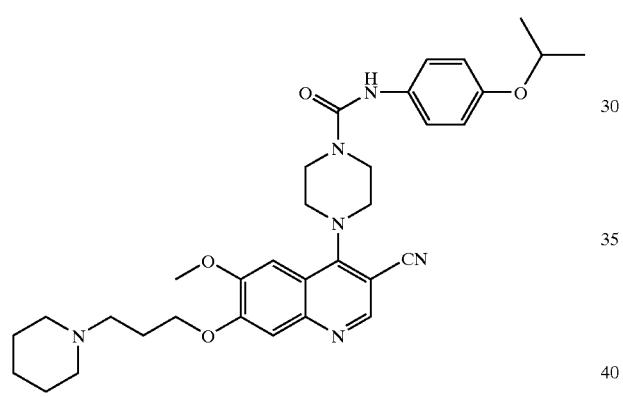

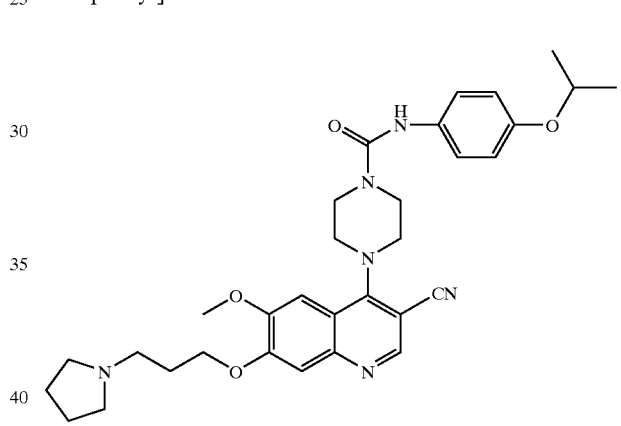

{4-[3-cyano-6-methoxy-7-(3-morpholin-4-ylpropoxy)quinolin-4-yl]piperazinyl}-N-[4-(methylethoxy)phenyl]carboxamide N-(4-cyanophenyl){4-[3-cyano-6-methoxy-7-(2-(1,2,3,4-tetraazol-2-yl)ethoxy)quinolin-4-yl]piperazinyl}carboxamide

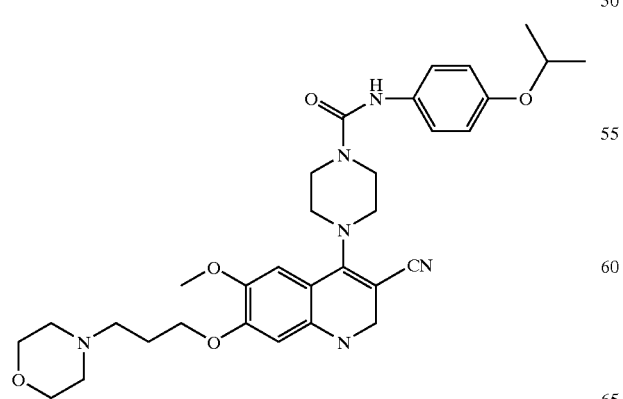

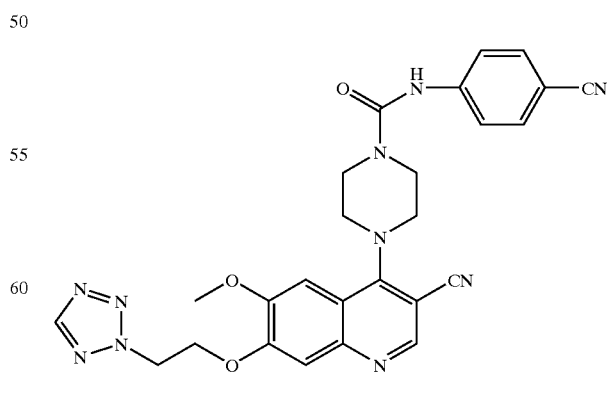

85

N-(4-cyanophenyl){4-[3-cyano-6-methoxy-7-(2-(1,2,3,4-tetraazolyl)ethoxy)quinolin-4-yl]piperazinyl}carboxamide

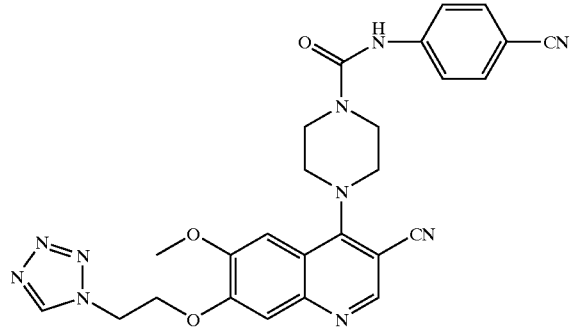

{4-(3-cyano-6-methoxy-7(2-(1,2,3,4-tetraazolyl)ethoxy)quinolin-4-yl]piperazinyl}-N-[4-(methylethoxy)phenyl]carboxamide

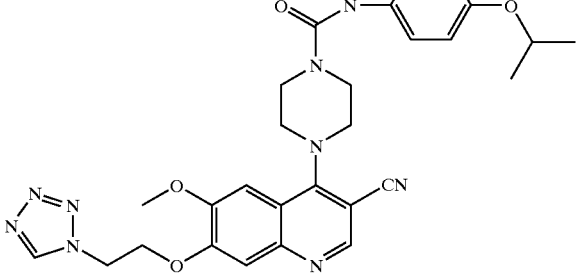

{4-[3-cyano-6-methoxy-7-(2-(1,2,3,4-tetraazol-2-yl)ethoxy)quinolin-4-yl]piperazinyl}-N-[4-(methylethoxy)phenyl]carboxamide

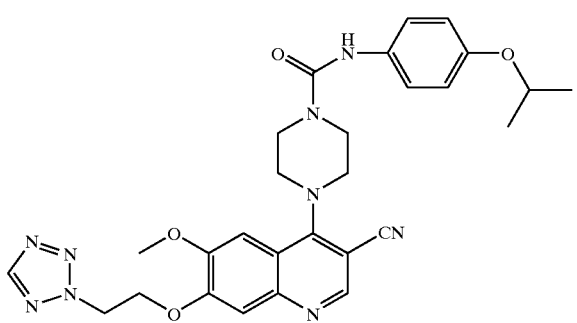

86

(4-{3-cyano-7-(3-(4,4-difluoropiperidyl)propoxy)-6-methoxyquinolin-4-yl}piperazinyl)-N-[4-(methylethoxy)phenyl]carboxamide

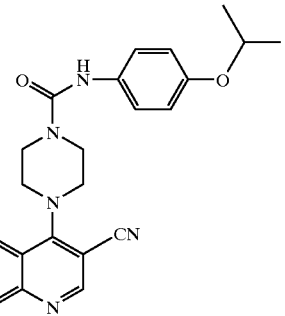

{4-[3-cyano-6-methoxy-7-(3-piperazinylpropoxy)quinolin-4-yl]piperazinyl}-N-[4-(methylethoxy)phenyl]carboxamide N-(4-cyanophenyl)(4-{3-cyano-6-methoxy-7-[3-(4-methylpiperazinyl)propoxy]quinolin-4-yl}piperazinyl)carboxamide N-(4-cyanophenyl){4-[3-cyano-6-methoxy-7-(3-(4-thiazaperhydroin-4-yl)propoxy)quinolin-4-yl]piperazinyl}carboxamide

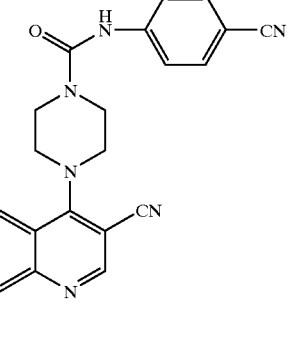

87

(4-{3-cyano-7-[3-(1,1-dioxo(1,4-thiazaperhydroin-4-yl))propoxy]-6-methoxyquinolin-4-yl}piperazinyl)-N-(4-cyanophenyl)carboxamide

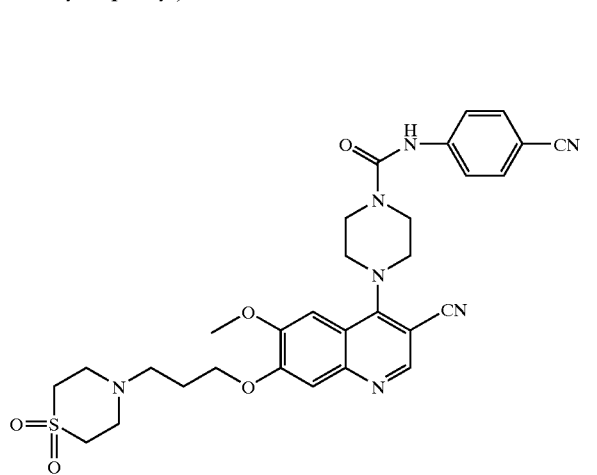

N-(4-cyanophenyl)[4-(3-cyano-7-ethoxy-6-methoxyquinolin-4-yl)piperazinyl]carboxamide

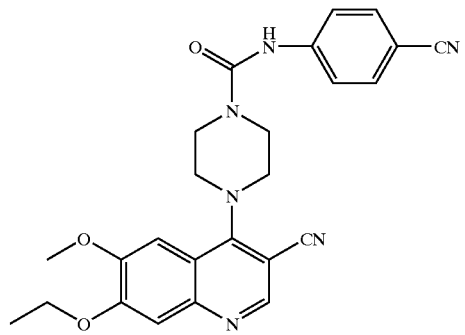

[4-(3-cyano-7-ethoxy-6-methoxyquinolin-4-yl)piperazinyl]-N-[4-(methylethoxy)phenyl]carboxamide

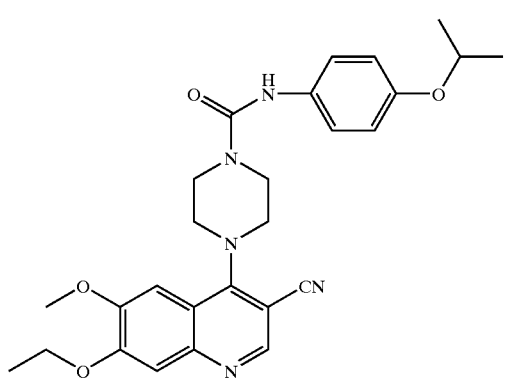

88

[4-(3-cyano-7-ethoxy-6-methoxyquinolin-4-yl)piperazinyl]-N-(4-naphthyloxyphenyl)carboxamide

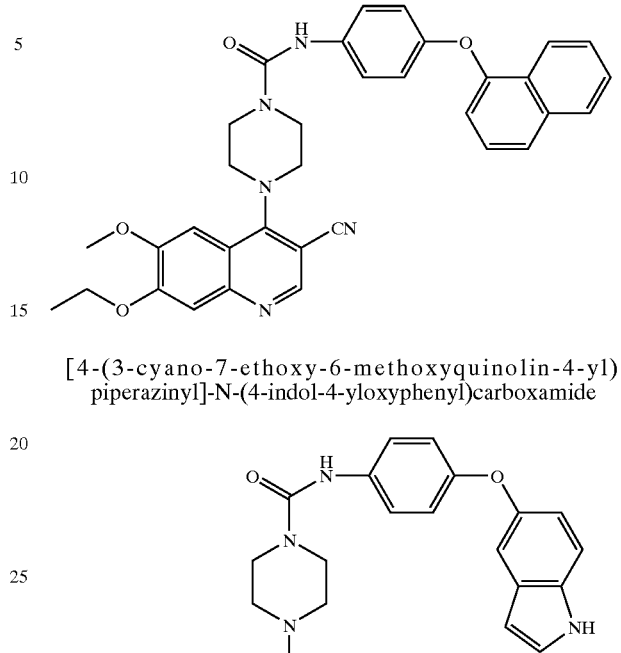

[4-(3-cyano-7-ethoxy-6-methoxyquinolin-4-yl)piperazinyl]-N-(4-indol-4-yloxyphenyl)carboxamide

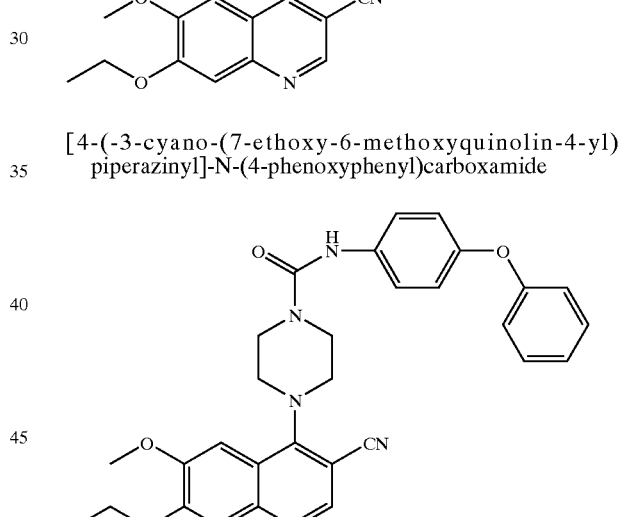

[4-(-3-cyano-(7-ethoxy-6-methoxyquinolin-4-yl)piperazinyl]-N-(4-phenoxyphenyl)carboxamide N-(4-cyanophenyl)[4-(3-cyano-6-methoxy-7-prop-2-enyloxyquinolin-4-yl)piperazinyl]carboxamide

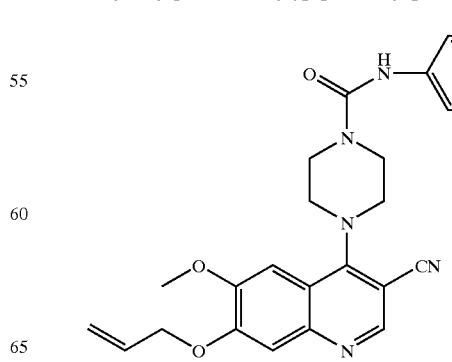

89

[4-(3-cyano-6-methoxy-7-prop-2-enyloxyquinolin-4-yl)piperazinyl]-N-[4-(methylethoxy)phenyl]carboxamide

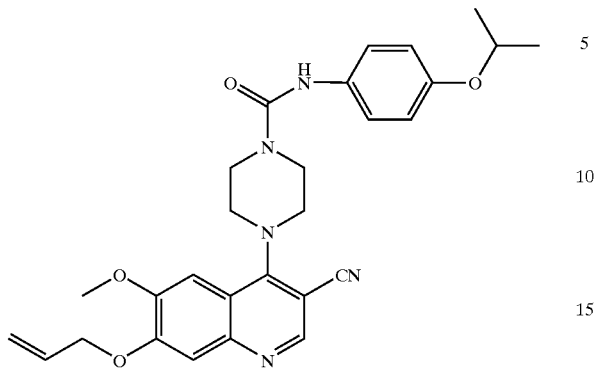

[4-(3-cyano-6-methoxy-7-prop-2-enyloxyquinolin-4-yl)piperazinyl]-N-(4-naphthyloxyphenyl)carboxamide

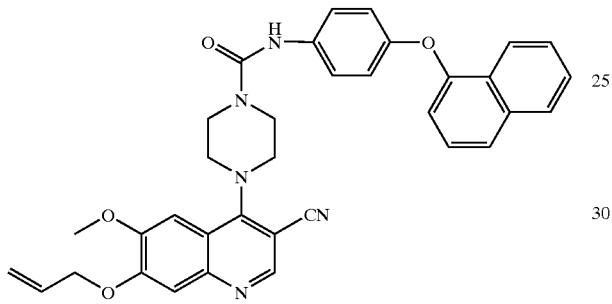

N-(4-indol-4-yloxyphenyl)[4-(3-cyano-6-methoxy-7-prop-2-enyloxyquinolin-4-yl)piperazinyl]carboxamide

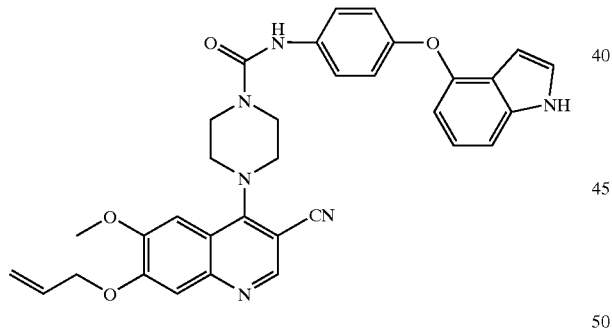

[4-(3-cyano-6-methoxy-7-prop-2-enyloxyquinolin-4-yl)piperazinyl]-N-(4-phenoxyphenyl)carboxamide

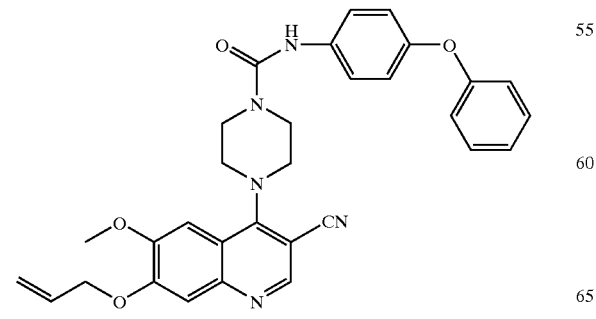

90

N-(4-cyanophenyl)[4-(3-cyano-6-methoxy-7-prop-2-ynyloxyquinolin-4-yl)piperazinyl]carboxamide

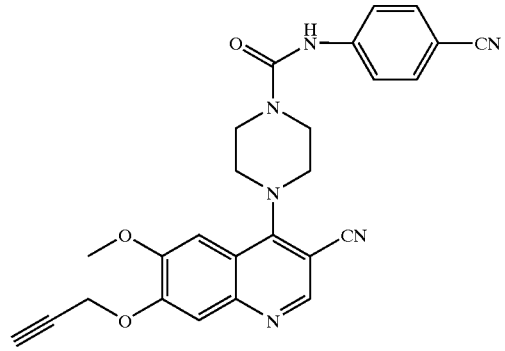

[4-(3-cyano-6-methoxy-7-prop-2-ynyloxyquinolin-4-yl)piperazinyl]-N-[4-(methylethoxy)phenyl]carboxamide

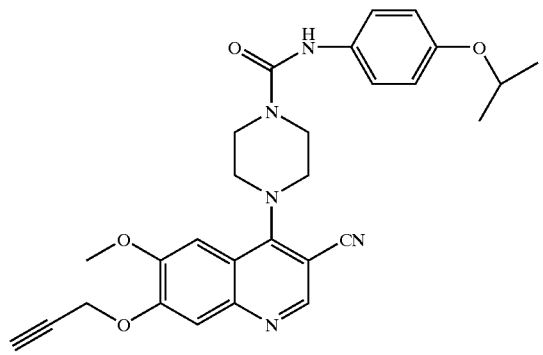

[4-(3-cyano-6-methoxy-7-prop-2-ynyloxyquinolin-4-yl)piperazinyl]-N-(4-naphthyloxyphenyl)carboxamide

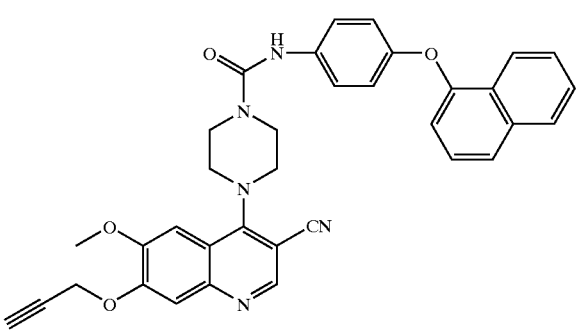

N-(4-indol-4-yloxyphenyl)[4-(3-cyano-6-methoxy-7-prop-2-ynyloxyquinolin-4-yl)piperazinyl]carboxamide

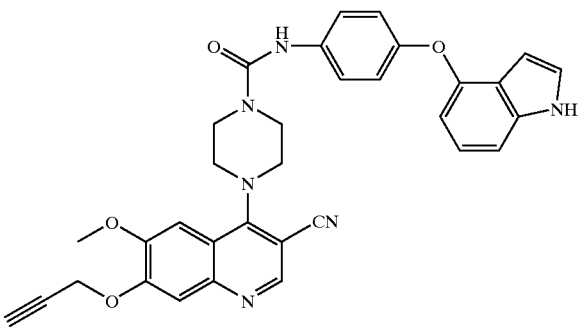

91

[4-(3-cyano-6-methoxy-7-prop-2-ynyloxyquinolin-4-yl)
piperazinyl]-N-(4-phenoxyphenyl)carboxamide

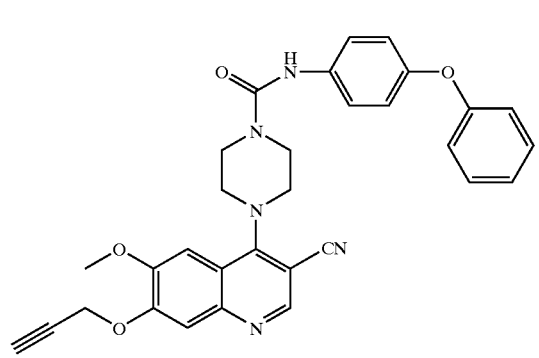

ethyl-6-methoxy-4-(4-{N-[4-(methylethoxy)phenyl]
carbamoyl}piperazinyl)-7-(3-piperidylpropoxy)
quinoline-3-carboxylate

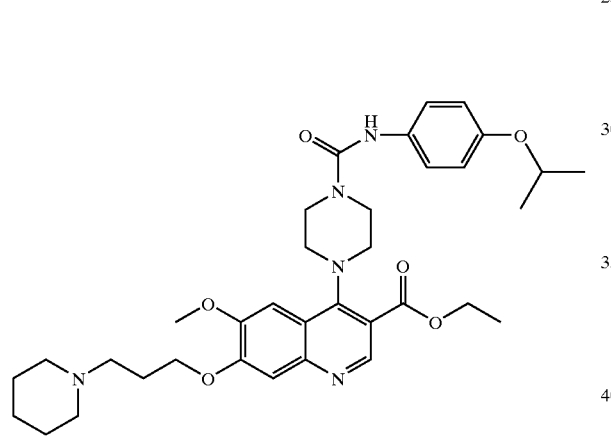

ethyl-6-methoxy-4-(4-{N-[4-(methylethoxy)phenyl]
carbamoyl}piperazinyl)-7-(3-morpholin-4-ylpropoxy)
quinoline-3-carboxylate

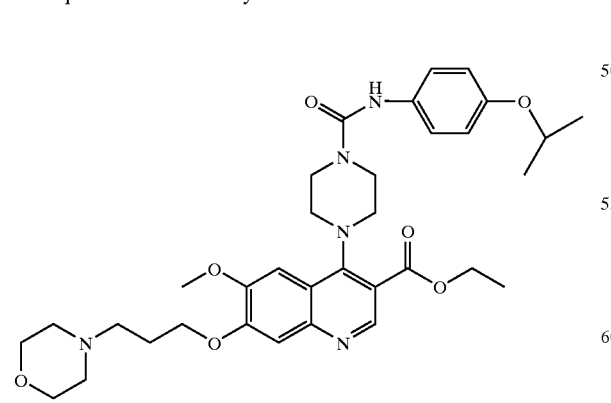

92 ethyl-6-methoxy-4-(4-{N-[4-(methylethoxy)phenyl]
carbamoyl}piperazinyl)-7-(3-(1,2,3-triazolyl)propoxy)
quinoline-3-carboxylate

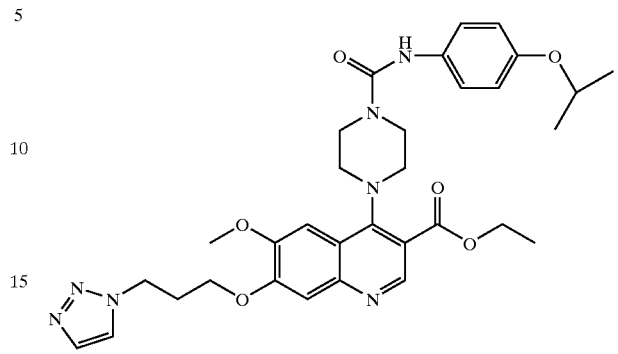

6-methoxy-4-(4-{N-[4-(methylethoxy)phenyl]
carbamoyl}piperazinyl)-7-(3-(1,2,3-triazol-2-yl)
propoxy)quinoline-3-carboxylic

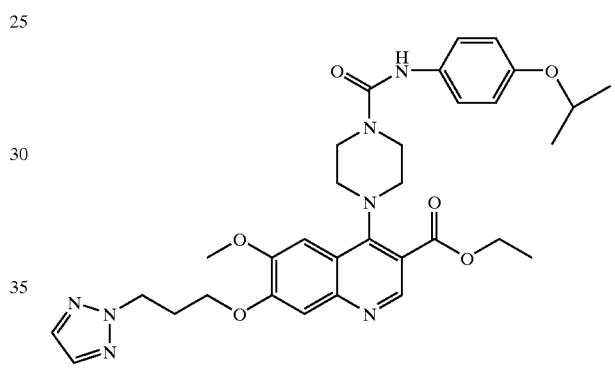

ethyl-4-{4-[N-(4-cyanophenyl)carbamoyl]piperazinyl}-
6-methoxy-7-(3-piperidylpropoxy)quinoline-3-
carboxylate

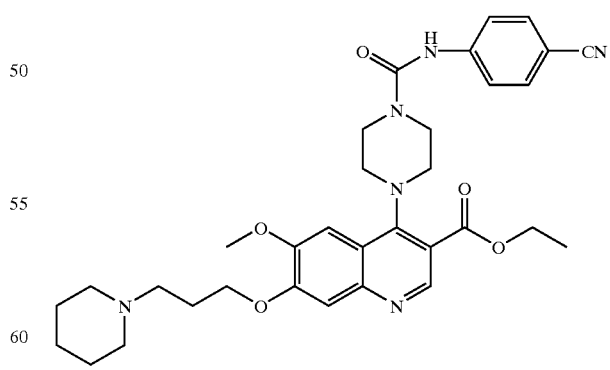

93 ethyl-4-{4-[N-(4-cyanophenyl)carbamoyl]piperazinyl}-6-methoxy-7-(3-morpholin-4-ylpropoxy)quinoline-3-carboxylate

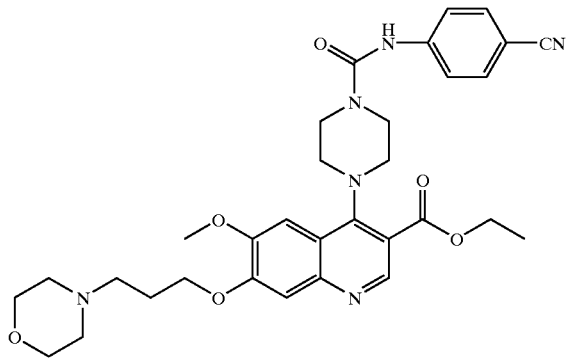

ethyl-4-{4-[N-(4-cyanophenyl)carbamoyl]piperazinyl}-6-methoxy-7-(3-pyrrolidinylpropoxy)quinoline-3-carboxylate

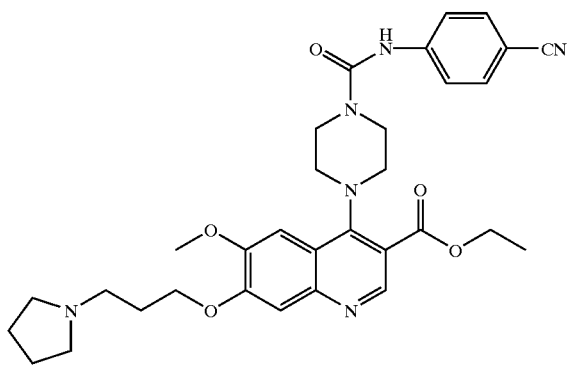

ethyl-4-{4-[N-(4-cyanophenyl)carbamoyl]piperazinyl}-6-methoxy-7-(3-(1,2,3-triazolyl)propoxy)quinoline-3-carboxylate

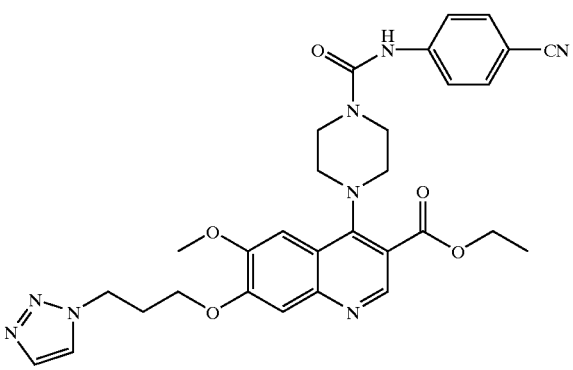

94 ethyl-4-{4-[N-(4-cyanophenyl)carbamoyl]piperazinyl}-6-methoxy-7-(3-(1,2,3-triazol-2-yl)propoxy)quinoline-3-carboxylate

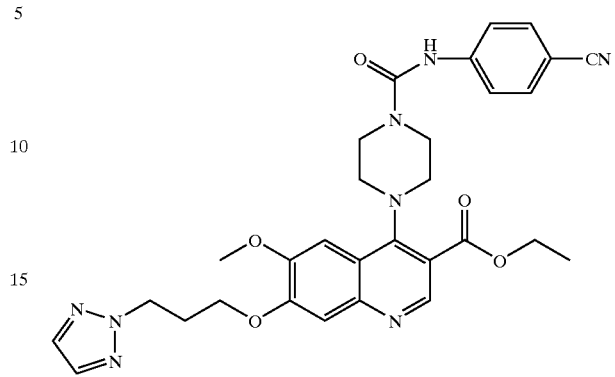

ethyl-4-{4-[N-(4-cyanophenyl)carbamoyl]piperazinyl}-6-methoxy-7-(3-(1,2,3,4-tetraazol-2-yl)propoxy)quinoline-3-carboxylate

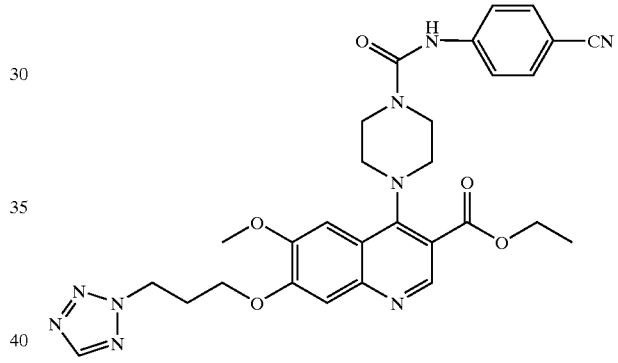

ethyl-4-{4-[N-(4-cyanophenyl)carbamoyl]piperazinyl}-6-methoxy-7-(3-(1,2,3,4-tetraazolyl)propoxy)quinoline-3-carboxylate

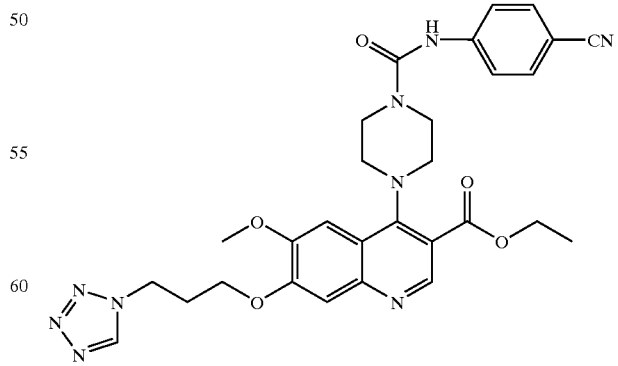

| 95 | 96 |
|---|---|
| ethyl-7-[3-(1,1-dioxo(1,4-thiazaperhydroin-4-yl)) propoxy]-4-{4-[N-(4-cyano-phenyl)carbomoyl] piperazinyl}-6-methoxyquinoline-3-carboxylate | ethyl-4-{4-[N-(4-cyanophenyl)carbamoyl]piperazinyl}- 6-methoxy-7-[3-(4-methylpiperazinyl)propoxy] quinoline-3-carboxylate |

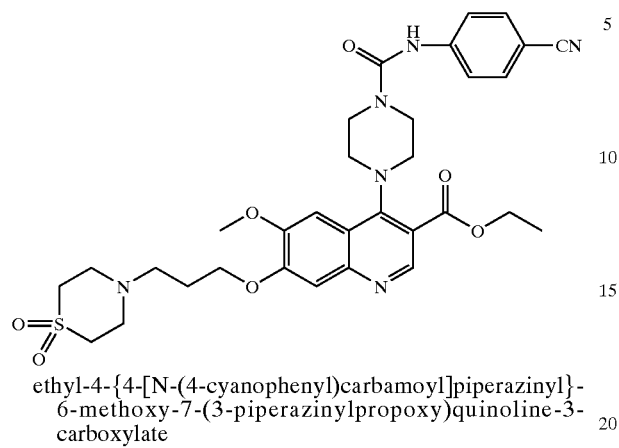

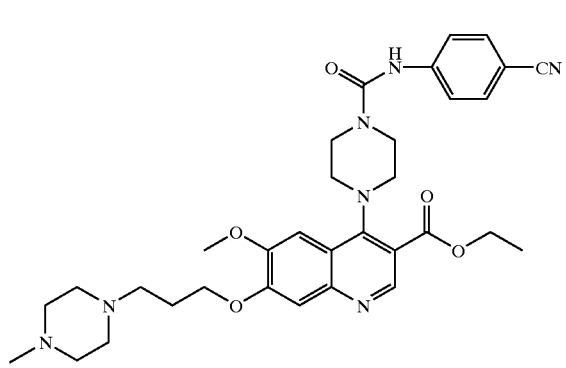

ethyl-4-{4-[N-(4-cyanophenyl)carbamoyl]piperazinyl}-
6-methoxy-7-(3-piperazinylpropoxy)quinoline-3-
carboxylate {4-[3-carbonyl-6-methoxy-7-(3-piperidylpropoxy)(4-
quinolyl)]piperazinyl}-N-[4-(methylethoxy)phenyl]
carboxamide

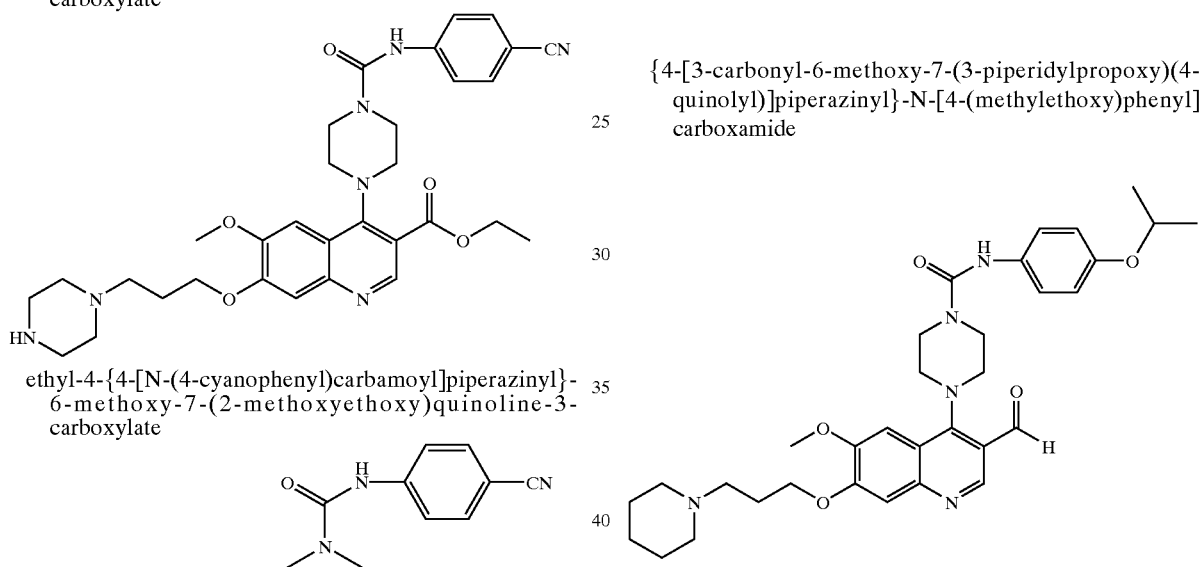

ethyl-4-{4-[N-(4-cyanophenyl)carbamoyl]piperazinyl}-
6-methoxy-7-(2-methoxyethoxy)quinoline-3-
carboxylate {4-[3-carbonyl-6-methoxy-7-(3-morpholin-4-ylpropoxy)
(4-quinolyl)]piperazinyl}-N-[4-(methylethoxy)phenyl]
carboxamide

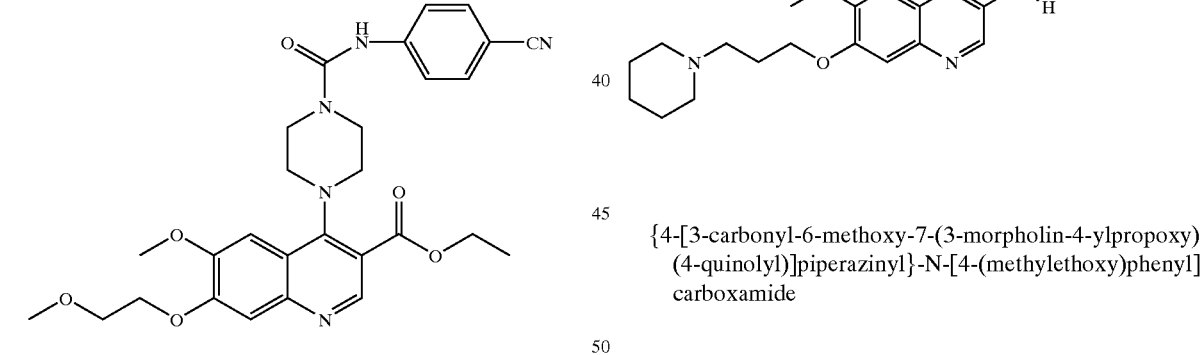

ethyl 6-methoxy-7-(2-methoxyethoxy)-4-(4-{N-[4-
(methylethoxy)phenyl]-carbamoyl}piperazinyl)
quinoline-3-carboxylate

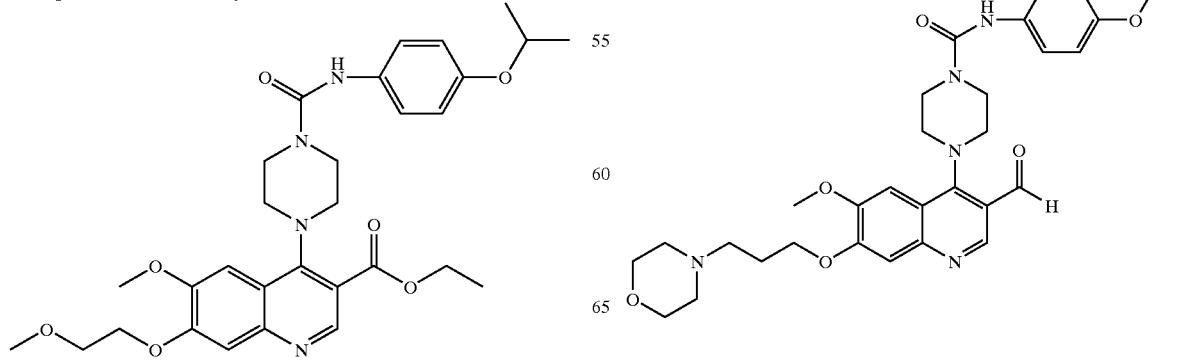

(4-{7-[3-(1,1-dioxo(1,4-thiazaperhydroin-4-yl))
propoxy]-3-carbonyl-6-methoxy(4-quinolyl)
}piperazinyl)-N-[4-(methylethoxy)phenyl]
carboxamide

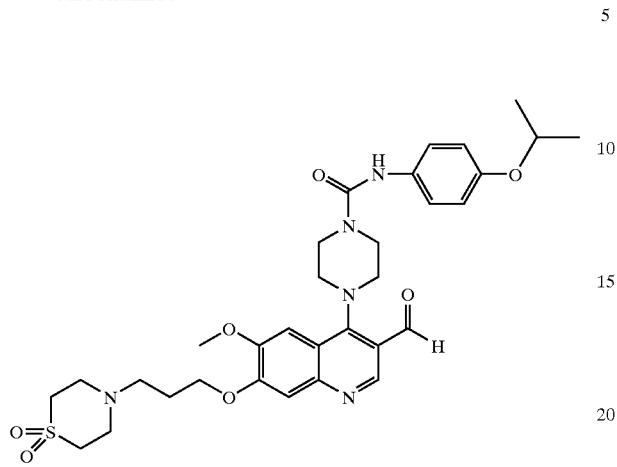

{4-[3-carbonyl-6-methoxy-7-(3-pyrrolidinylpropoxy)(4-
quinolyl)]piperazinyl}-N-[4-(methylethoxy)phenyl]
carboxamide

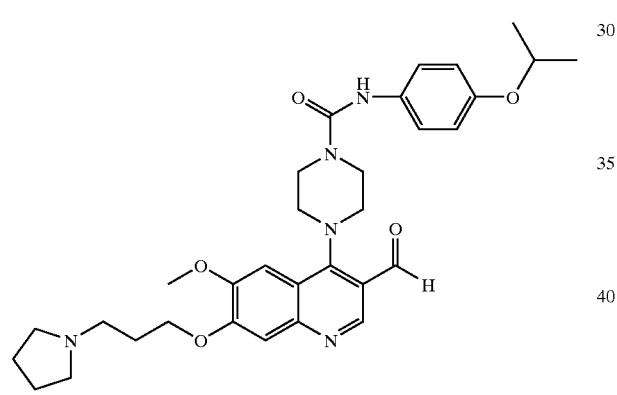

{4-[3-carbonyl-6-methoxy-7-(3-piperidylpropoxy)(4-
quinolyl)]piperazinyl}-N-(4-cyanophenyl)
carboxamide

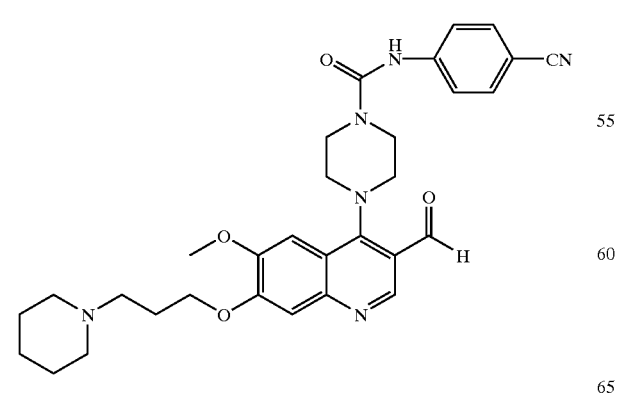

{4-[3-carbonyl-6-methoxy-7-(3-morpholin-4-ylpropoxy)
(4-quinolyl)]piperazinyl}-N-(4-cyanophenyl)
carboxamide

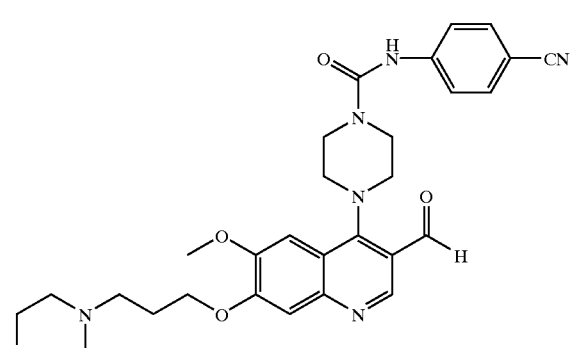

{4-[3carbonyl-6-methoxy-7-(3-pyrrolidinylpropoxy)(4-
quinolyl)]piperazinyl}-N-(4-cyanophenyl)
carboxamide

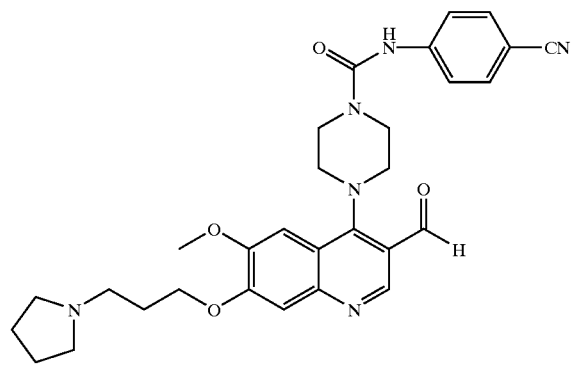

{4-[3-carbonyl-6-methoxy-7-(3-(1,2,3-triazolyl)propoxy)
(4-quinolyl)]piperazinyl}-N-(4-cyanophenyl)
carboxamide

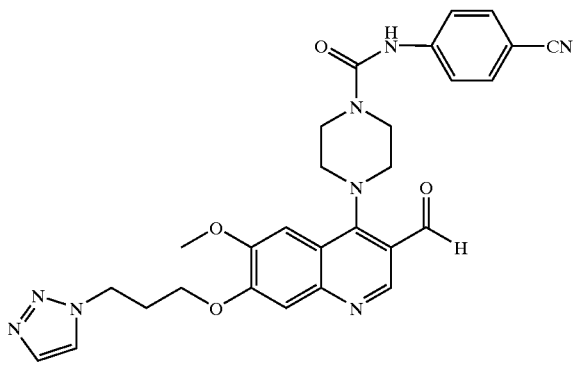

| 99 | 100 |
|---|---|
| {4-[3-carbonyl-6-methoxy-7-(3-(1,2,3-triazol-2-yl)propoxy)(4-quinolyl)]piperazinyl}-N-(4-cyanophenyl)carboxamide | {4-[3-(hydroxymethyl)-6-methoxy-7-(3-piperidylpropoxy)(4-quinolyl)]piperazinyl}-N-[4-(methylethoxy)phenyl]carboxamide |

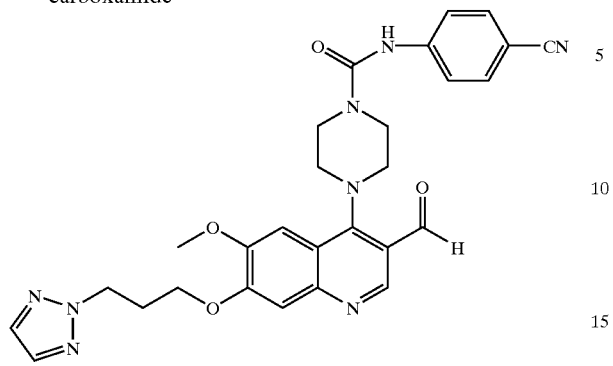

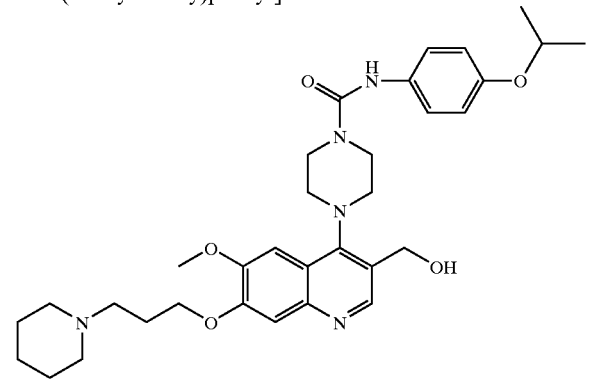

N-(4-cyanophenyl){4-[3-(hydroxymethyl)-6-methoxy-7-(3-piperidylpropoxy)(4-quinolyl)]piperazinyl}carboxamide {4-[3-(hydroxymethyl)-6-methoxy-7-(3-morpholin-4-ylpropoxy)(4-quinolyl)]piperazinyl}-N-4-(methylethoxy)phenyl]carboxamide

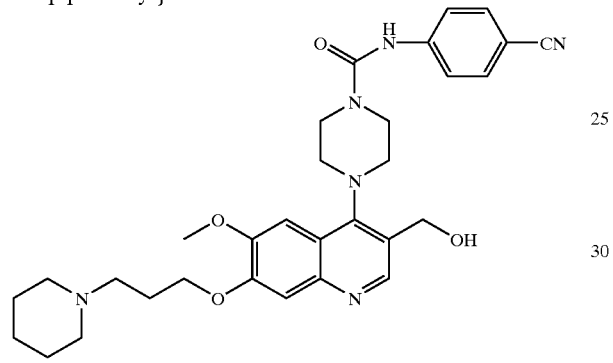

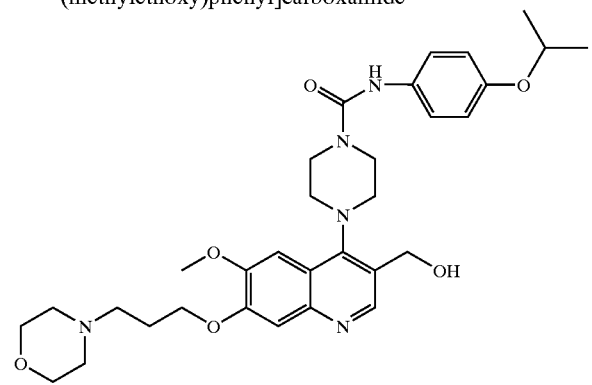

N-(4cyanophenyl){4-[3-(hydroxymethyl)-6-methoxy-7-(3-morpholin-4ylpropoxy)(4-quinolyl)]piperazinyl}carboxamide (4-{7-[3-(1,1-dioxo(1,4-thiazaperhydroin-4-yl))propoxy]-3-(hydroxymethyl)-6-methoxy(4-quinolyl)}piperazinyl)-N-[4-(methylethoxy)phenyl]carboxamide

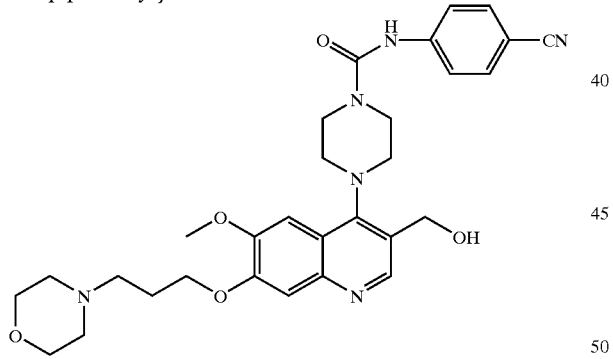

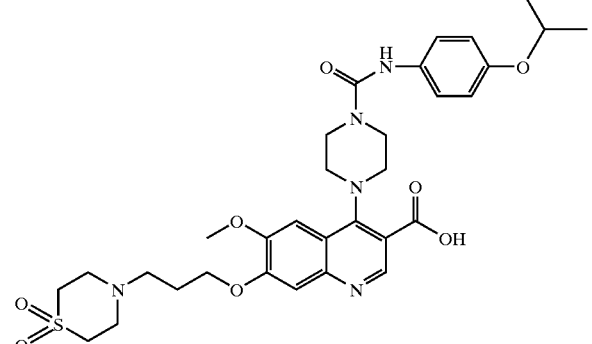

N-(4-cyanophenyl){4-[3-(hydroxymethyl)-6-methoxy-7-(3-pyrrolidinylpropoxy)(4-quinolyl)]piperazinyl}carboxamide {4-[3-(hydroxymethyl)-6-methoxy-7-(3-pyrrolidinylpropoxy)(4-quinolyl)]piperazinyl}-N-[4-(methylethoxy)phenyl]carboxamide

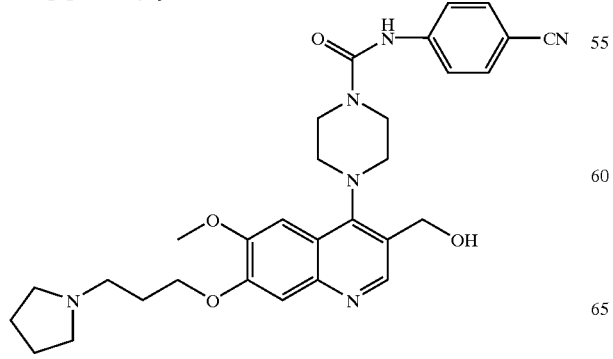

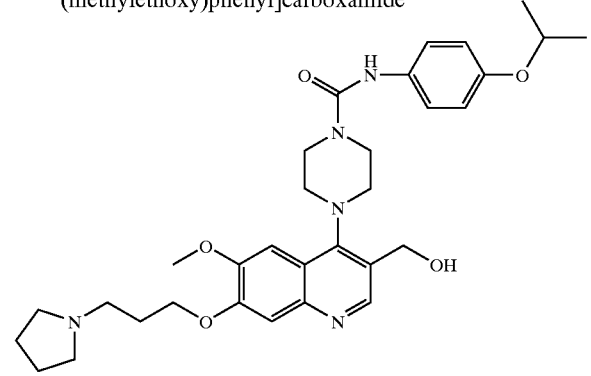

101

4-[3-Aminomethyl-6-methoxy-7-(3-piperidin-1-yl-propoxy)-quinolin-4-yl]-piperazine-1-carboxylic acid (4-cyano-phenyl)-amide

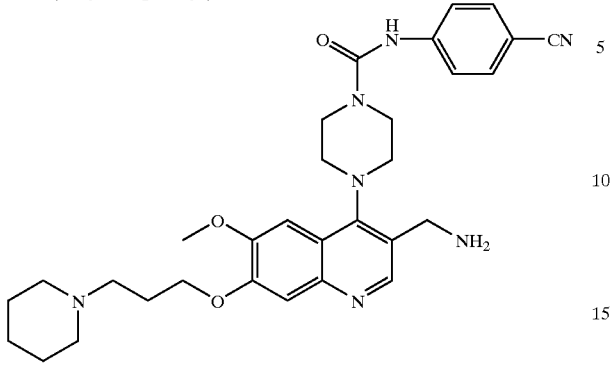

4-[3-Aminomethyl-6-methoxy-7-(3-piperidin-1-yl-propoxy)-quinolin-4-yl]-piperazine-1-carboxylic acid (4-isopropoxy-phenyl)-amide

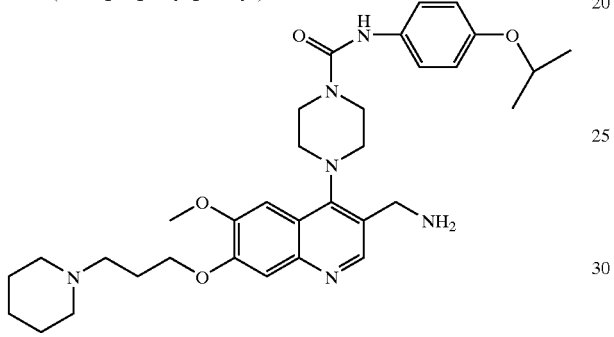

4-[3-Aminomethyl-6-methoxy-7-(3-morpholin-4-yl-propoxy)-quinolin-4-yl]-piperazine-1-carboxylic acid (4-cyano-phenyl)-amide

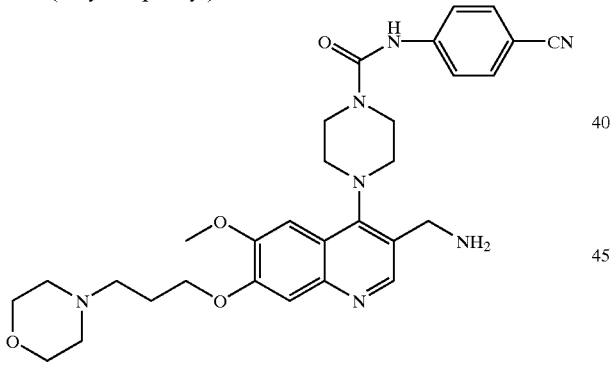

4-[3-Aminomethyl-6-methoxy-7-(3-morpholin-4-yl-propoxy)-quinolin-4-yl]-piperazine-1-carboxylic acid (4-isopropoxy-phenyl)-amide

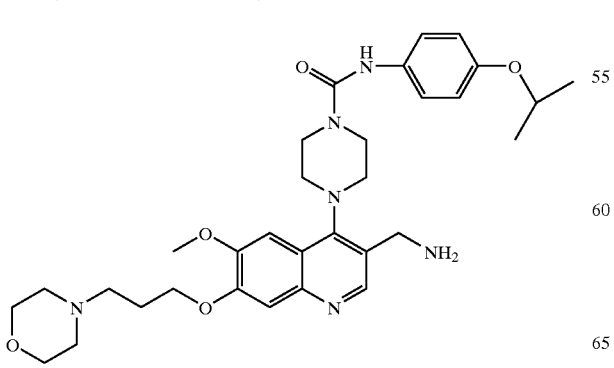

102

4-[3-Cyano-6-methoxy-7-(3-pyrrolidin-1-yl-propoxy)-quinolin-4-yl]-piperazine-1-carboxylic acid (4-cyano-phenyl)-amide

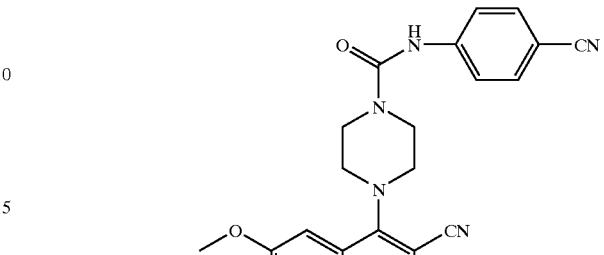
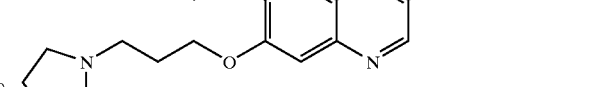

4-[3-Cyano-6-methoxy-7-(3-pyrrolidin-1-yl-propoxy)-quinolin-4-yl]-piperazine-1-carboxylic acid (4-bromo-phenyl)-amide

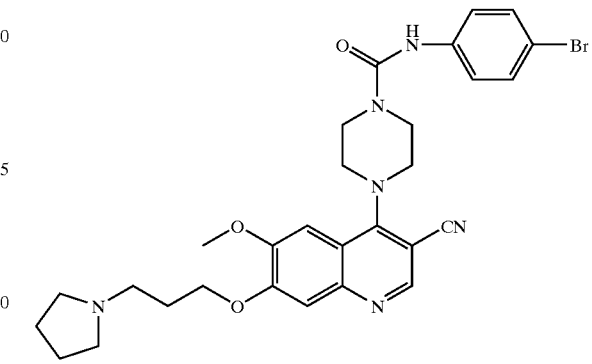

4-[3-Cyano-6-methoxy-7-(3-pyrrolidin-1-yl-propoxy)-quinolin-4-yl]-piperazine-1-carboxylic acid (4-isopropoxy-phenyl)-amide

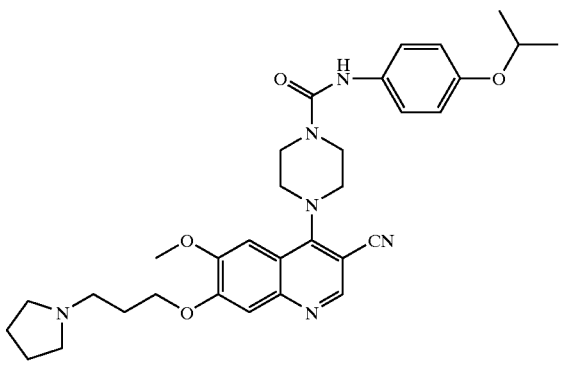

4-({4-[3-Cyano-6-methoxy-7-(3-pyrrolidin-1-yl-propoxy)-quinolin-4-yl]-piperazine-1-carbonyl}-amino)-benzoic acid methyl ester

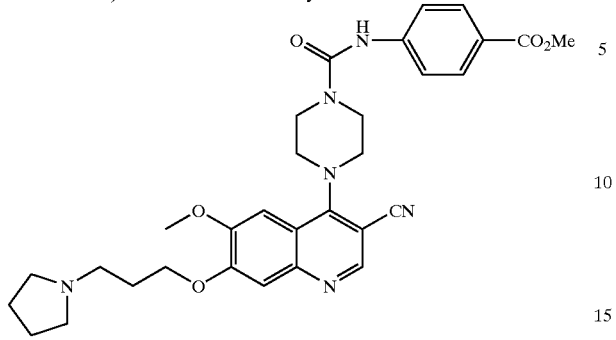

4-({4-[3-Cyano-6-methoxy-7-(3-piperidin-1-yl-propoxy)-quinolin-4-yl]-piperazine-1-carbonyl}-amino)-benzoic acid methyl ester

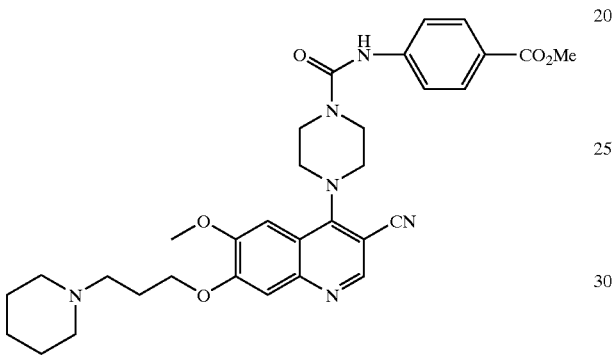

4-[3-Cyano-6-methoxy-7-(3-piperidin-1-yl-propoxy)-quinolin-4-yl]-piperazine-1-carboxylic acid (4-bromo-phenyl)-amide

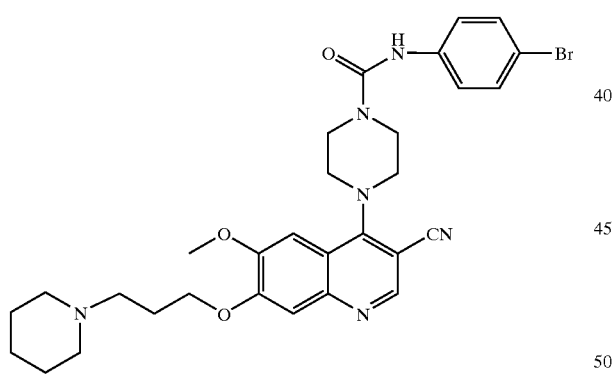

4-[3-Cyano-6-methoxy-7-(3-piperidin-1-yl-propoxy)-quinolin-4-yl]-piperazine-1-carboxylic acid (4-trifluoromethyl-phenyl)-amide

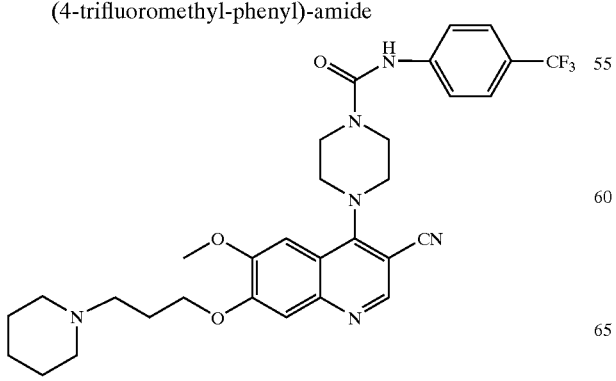

4-[3-Cyano-6-methoxy-7-(3-piperidin-1-yl-propoxy)-quinolin-4-yl]-piperazine-1-carboxylic acid (4-fluoro-phenyl)-amide

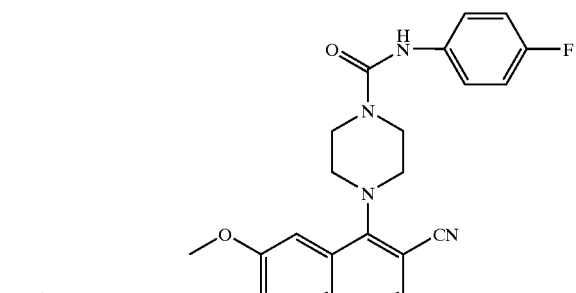

4-[3-Fluoro-6-methoxy-7-(3-piperidin-1-yl-propoxy)-quinolin-4-yl]-piperazine-1-carboxylic acid (4-cyano-phenyl)-amide

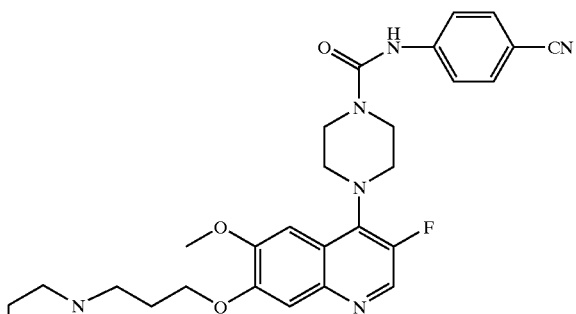

4-[3-Fluoro-6-methoxy-7-(3-piperidin-1-yl-propoxy)-quinolin-4-yl]-piperazine-1-carboxylic acid (4-isopropoxy-phenyl)-amide

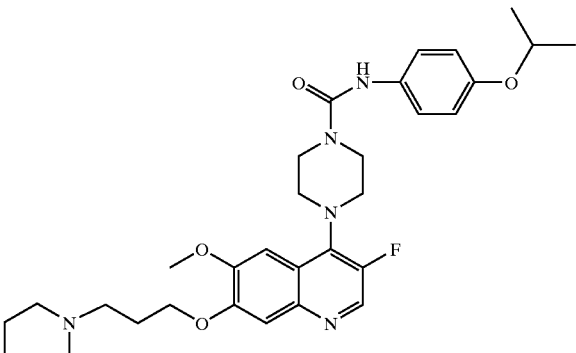

4-[3-Fluoro-6-methoxy-7-(3-morpholin-4-yl-propoxy)-
quinolin-4-yl]-piperazine-1-carboxylic acid (4-cyano-
phenyl)-amide

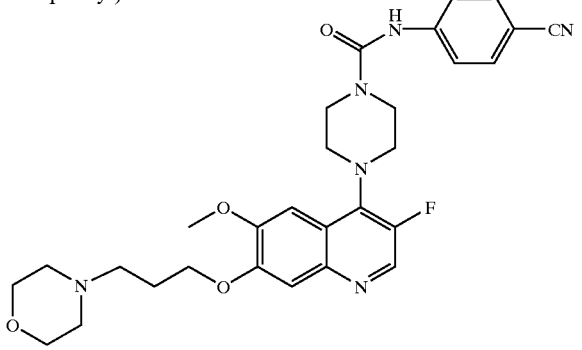

4-[3-Fluoro-6-methoxy-7-(3-morpholin-4-yl-propoxy)-
quinolin-4-yl]-piperazine-1-carboxylic acid
(4-isopropoxy-phenyl)-amide

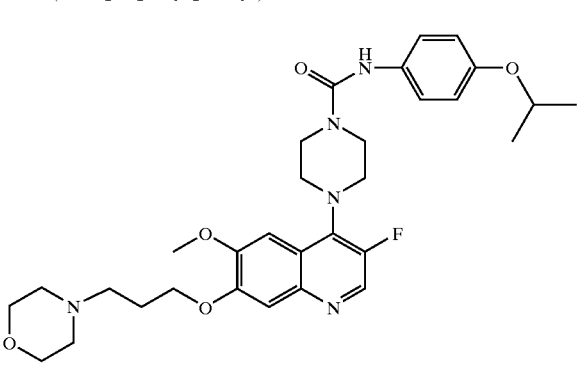

4-[3-Fluoro-6-methoxy-7-(3-pyrrolidin-1-yl-propoxy)-
quinolin-4-yl]-piperazine-1-carboxylic acid (4-cyano-
phenyl)-amide

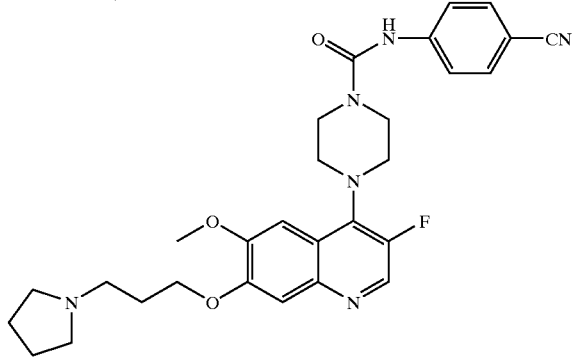

4-[3-Fluoro-6-methoxy-7-(3-pyrrolidin-1-yl-propoxy)-
quinolin-4-yl]-piperazine-1-carboxylic acid (4-bromo-
phenyl)-amide

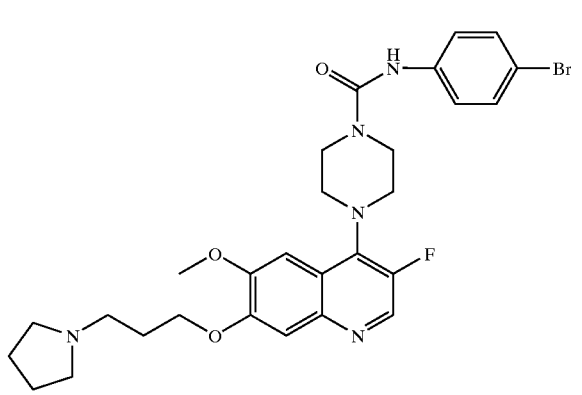

4-[3-Fluoro-6-methoxy-7-(3-pyrrolidin-1-yl-propoxy)-
quinolin-4-yl]-piperazine-1-carboxylic acid
(4-isopropoxy-phenyl)-amide

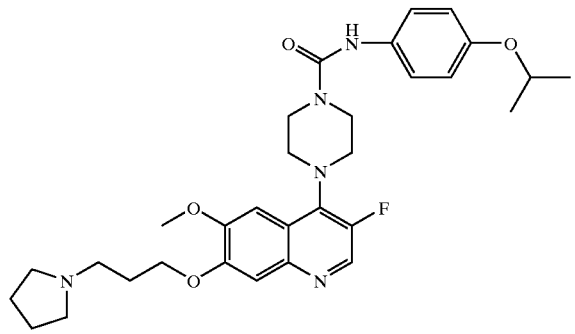

4-({4-[3-Fluoro-6-methoxy-7-(3-pyrrolidin-1-yl-
propoxy)-quinolin-4-yl]-piperazine-1-carbonyl}-
amino)-benzoic acid methyl ester

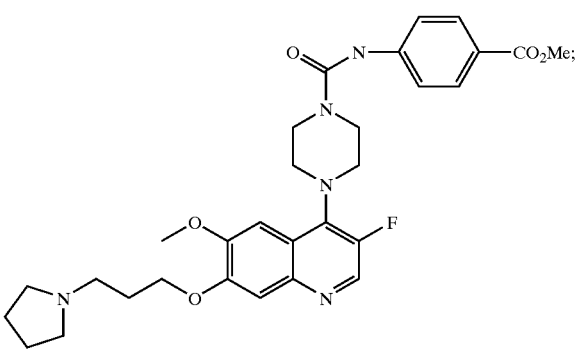

or all pharmaceutically acceptable salts or hydrates thereof.

4. A pharmaceutical composition comprising and effective amount of a compound according to claim 1, or a pharmaceutically acceptable salt thereof, and a pharmaceutically acceptable diluent or carrier.

5. A method of treating a cell-proliferative disease in a patient in need thereof, said method comprising administering to the patient a composition according to claim 4 wherein the cell-proliferative disease is selected from the group consisting of bone cancer, arteriosclerosis, vascular reobstruction, articular rheumatism, psoriasis, diabetic retinopathy, glomerulonephritis and glomerulosclerosis.

* * * * *

UNITED STATES PATENT AND TRADEMARK OFFICE
CERTIFICATE OF CORRECTION

PATENT NO.        : 6,960,580 B2
APPLICATION NO. : 10/094191
DATED             : November 1, 2005
INVENTOR(S)       : Scarborough et al.

It is certified that error appears in the above-identified patent and that said Letters Patent is hereby corrected as shown below:

In claim 1, column 79, line 40, please correct the chemical drawings to read:

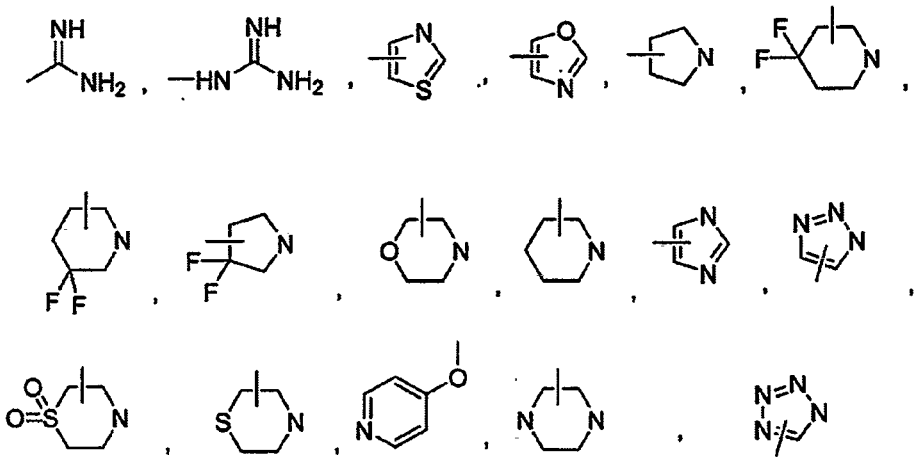

In claim 3, column 99 at line 36, delete "-4 ylpropoxy)" and insert -- -4-ylpropoxy) --.

In claim 3, column 100 at line 19, delete "–N–4-" and insert -- –N–[4– --.

In claim 3, column 100, line 40, please correct the chemical drawings to read:
{4-[3-(hydroxymethyl)-6-methoxy-7-(3-piperidylpropoxy)(4-quinolyl)]piperazinyl}-N-[4-(methylethoxy)phenyl]carboxamide

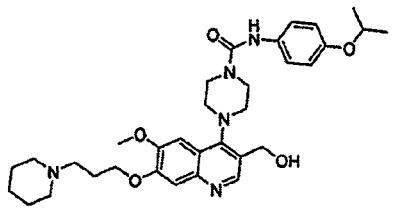

{4-[3-(hydroxymethyl)-6-methoxy-7-(3-morpholin-4-yipropoxy)-(4-quinolyl)]piperazinyl}-N-[4-(methylethoxy)phenyl]carboxamide

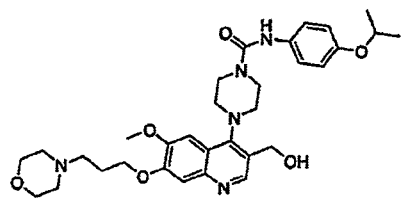

UNITED STATES PATENT AND TRADEMARK OFFICE
CERTIFICATE OF CORRECTION

PATENT NO. : 6,960,580 B2
APPLICATION NO. : 10/094191
DATED : November 1, 2005
INVENTOR(S) : Scarborough et al.

It is certified that error appears in the above-identified patent and that said Letters Patent is hereby corrected as shown below:

(4-{7-[3-(1,1-dioxo(1,4-thiazaperhydroin-4-yl))propoxy]-3-(hydroxymethyl)-6-methoxy(4-quinolyl)}piperazinyl)-N-[4-(methylethoxy)phenyl]carboxamide

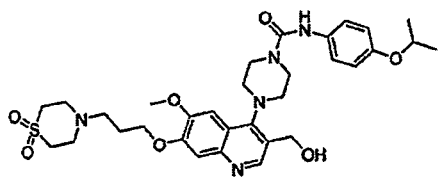

{4-[3-(hydroxymethyl)-6-methoxy-7-(3-pyrrolidinylpropoxy)(4-quinolyl)]piperazinyl}-N-[4-(methylethoxy)phenyl]carboxamide

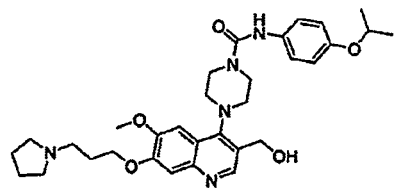

Signed and Sealed this

Fourteenth Day of November, 2006

JON W. DUDAS
*Director of the United States Patent and Trademark Office*